(12) United States Patent
Mink et al.

(10) Patent No.: US 7,402,575 B2
(45) Date of Patent: Jul. 22, 2008

(54) METHODS OF TREATING INFLAMMATION

(76) Inventors: Steven N. Mink, 1106-7 Evergreen Place, Winnipeg, Manitoba (CA) R3E 0Z3; Hans Jacobs, Thomas Mann Str. 5, Roesrath (DE) D-51503; Deepak Bose, 46 Lancaster Boulevard, Winnipeg, Manitoba (CA) R3P 0E4; Krika Duke, 244 Elmhurst Road, Winnipeg, Manitoba (CA) R3R 0T4; R. Bruce Light, 50 McNulty Crescent, Winnipeg, Manitoba (CA) R2M 5H4

( * ) Notice: Subject to any disclaimer, the term of this patent is extended or adjusted under 35 U.S.C. 154(b) by 498 days.

(21) Appl. No.: 10/762,581

(22) Filed: Jan. 23, 2004

(65) Prior Publication Data
US 2004/0214792 A1 Oct. 28, 2004

Related U.S. Application Data

(60) Provisional application No. 60/442,060, filed on Jan. 24, 2003.

(51) Int. Cl.
*A61K 31/722* (2006.01)
*C08B 37/08* (2006.01)

(52) U.S. Cl. .......................... 514/53; 514/55; 514/61; 536/20; 536/123.1

(58) Field of Classification Search .................. 514/313, 514/443, 530, 25, 28, 277, 288, 315; 530/350; 536/23.1, 23.5, 24.31; 435/320.1, 69.1, 252.3, 435/71.1, 6; 424/208, 94.61
See application file for complete search history.

(56) References Cited

U.S. PATENT DOCUMENTS 5,639,734 A * 6/1997 Esko et al. ..................... 514/25
6,653,294 B2 * 11/2003 Hwang et al. ................. 514/55

OTHER PUBLICATIONS

Valisena et al. "Lysozyme inhibitors enhance immune response in mice." Microbiologica, 19, pp. 25-30, 1996.*
Rand-Meir et al. "Use of synthetic substrates to study binding and catalysis by lysozyme." Biochemistry, vol. 8, No. 10, 4206-4214,1969.*
Rubio et al. "Early interactions between inhibitors and antibodies to lysozyme." Immunochemistry, vol. 10, 361-364, 1973.*
2006 CHemical Abstracts Catalog, published 2006 by Chemical Abstracts Service, p. 52.*
Parker JL et al., *Am J Physiol.*, Jun. 1985;248(6 Pt 2):H818-26.
Parker MM et al., *Annals of Internal Medicine*, 1984, 100:483-490.
Lefer AM and Rovetto MJ, *Proc Soc Exp Biol Med.* May 1970;134(1):269-73.
Lefer AM et al., *Am J Physiol.* Aug. 1967;213(2);492-8.
Parillo JE et al., *J Clin Invest.* Oct. 1985;76(4):1539-53.
Gomez A et al., *Anesthesiology*, 1990, 73:671-685.
Jha P et al., *Am J Physiol.* May 1993;264(5 Pt 2):H1402-10.
Eng JK et al., *J Am Soc Mass Spectrom*, 1994, 5:976-989.
Chittum HS et al., *Biochemistry*, 1998, 37:10866-10870.
http://www.nap.edu/readingroom/books/labrats/ *Guide for the care and use of laboratory animals*, © 1996, National Academy of Sciences.
Edman, P, *Mol. Biol. Biochem. Biophysics*, 1970, 8:211-255.
Rademacher TW et al., *Ann. Rev. Biochem.* 1988, 57:785-838.
Boyum A, *Nature*, Nov. 1964;204(4096):793-794.
Grobler JA et al., *Archives of Biochemistry and Biophysics*, Sep. 1994;313(2):360-366.
Shugar D, *Biochimica et Biophysica Acta*, 1952, 8:302-309.
Chipman DM and Sharon N, *Science*, 1969, 165:454-465.
Rand-Meir T et al., *Biochemistry*, 1969, 8(10):4206-4214.
Li X et al., *J Appl Physiol*, 1998, 85(5):1693-1701.
Eichenholz PW et al., *Am J Physiol.* Sep. 1992;263(3 Pt 2):H668-75.
Finkel MS et al., *Science*, Jul. 1992, 257:387-389.
Burgess P et al., *Surgery*, 1994, 115(1):16-21.
McDonald TE et al., *Am J Physiol Heart Circ Physiol*, 2000, 279:H2053-H2061.
Gu M et al., *Can J Anaesth*, 1998, 45(4):352-359.
Fleming, A., *Proceedings of the Royal Society of London (Biology)*, 1922, 93:306-317.
Briggs RS et al., *The Journal of Histochemistry and Cytochemistry*, 1966, 14(2):167-170.
Hansen NE and Andersen V, *British Journal of Haematology*, 1973, 24:613-622.
Hansen NE et al., *The Journal of Clinical Investigation*, 1972, 51:1146-1155.
Henning U et al., *Molecular and Cellular Biochemistry*, 1996, 160/161:41-46.
Ufret-Vincenty CA et al., *Am J Physiol Cell Physiol*, 2001, 281:C464-C474.
Bennet ES, *Biophysical Journal*, 1999, 77:2999-3009.
Lollike K et al., *Leukemia*, 1995, 9:206-209.
Granton JT et al., *Am J Respir Crit Care Med*, 1997, 155:1977-1983.
Flecknell P, *Laboratory Animal Anaesthesia: A pratical introduction for research workers and technicians*, 2nd ed., London: Academic Press, 1996.
Crusch C et al., *Am J Respir Crit Care Med*, 2000, 161:517-526.
Mink SN et al., *Intensive Care Med*, 1999, 25:733-743.
Maley F et al., *Analytical Biochemistry*, 1989, 180:195-204.
Nachbar MS et al., *The Journal of Biological Chemistry*, 1980, 255(5):2056-2061.
Crowley JF et al., *Archives of Biochemistry and Biophysics*, 1984, 231(2):524-533.
Nagata Y and Burger MM, *The Journal of Biological Chemistry*, 1974, 249(10):3116-3122.
Gilboa-Garber N and Mizrahi L, *Can J Biochem*, 1981, 59:315-320.
Hammarstrom S et al., *Scand J Immunol*, 1972, 1:295-309.
Varki A et al. Eds., *Essentials of Glycobiology*, Cold Spring Harbor Laboratory Press, Cold Spring Harbor, NY: 1999.

* cited by examiner

Primary Examiner—Shaojia Anna Jiang
Assistant Examiner—Eric S Olson
(74) *Attorney, Agent, or Firm*—Michael R. Williams; Adrian D. Battison; Ryan W. Dupuis

(57) ABSTRACT

Methods and compositions for treating myocardial dysfunction or inflammation are described. The methods of the invention involve administering an agent that can inhibit lysozyme to an animal in need thereof. Preferred lysozyme inhibitors include TAC and chitobiose.

10 Claims, 39 Drawing Sheets

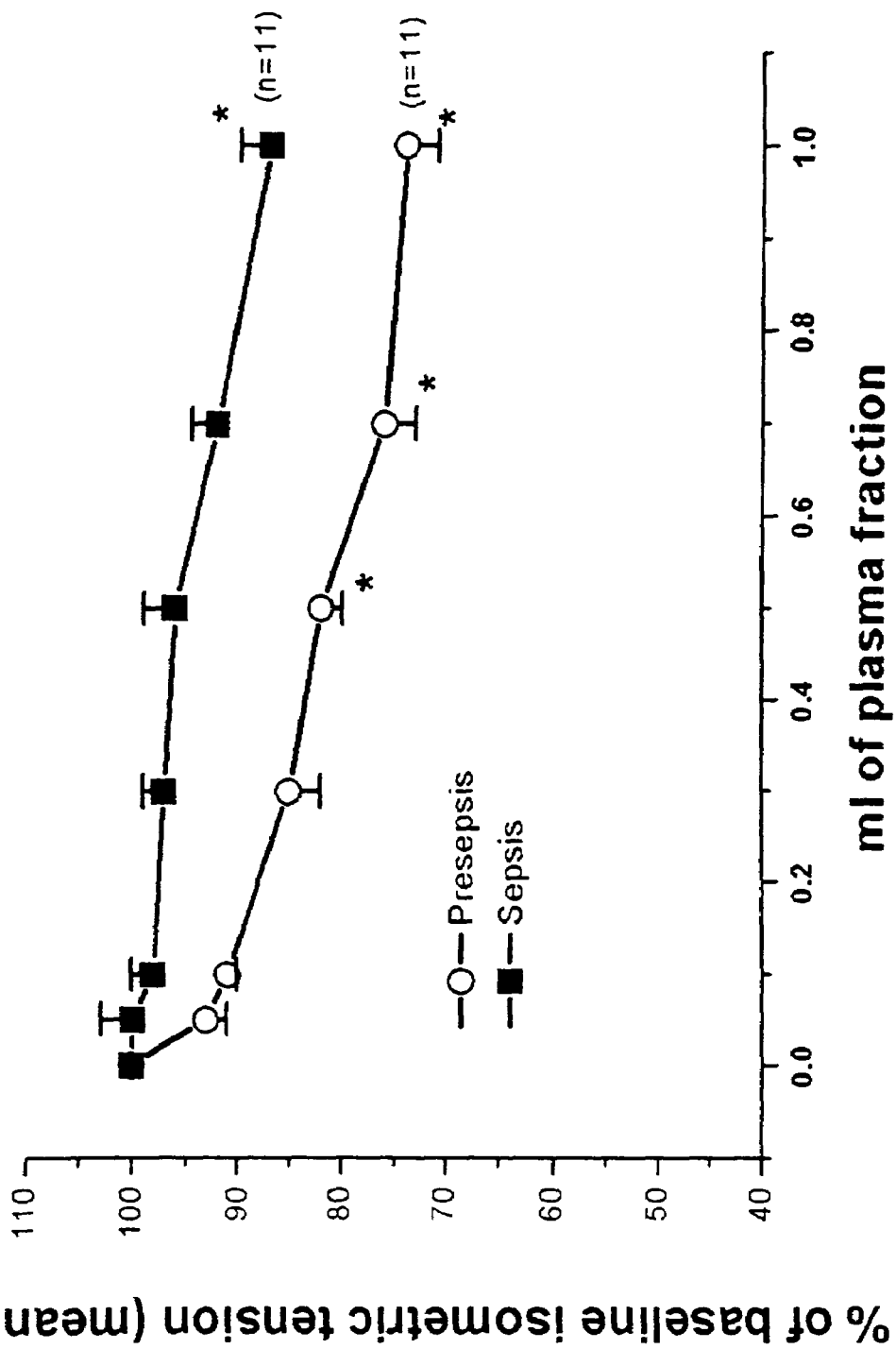

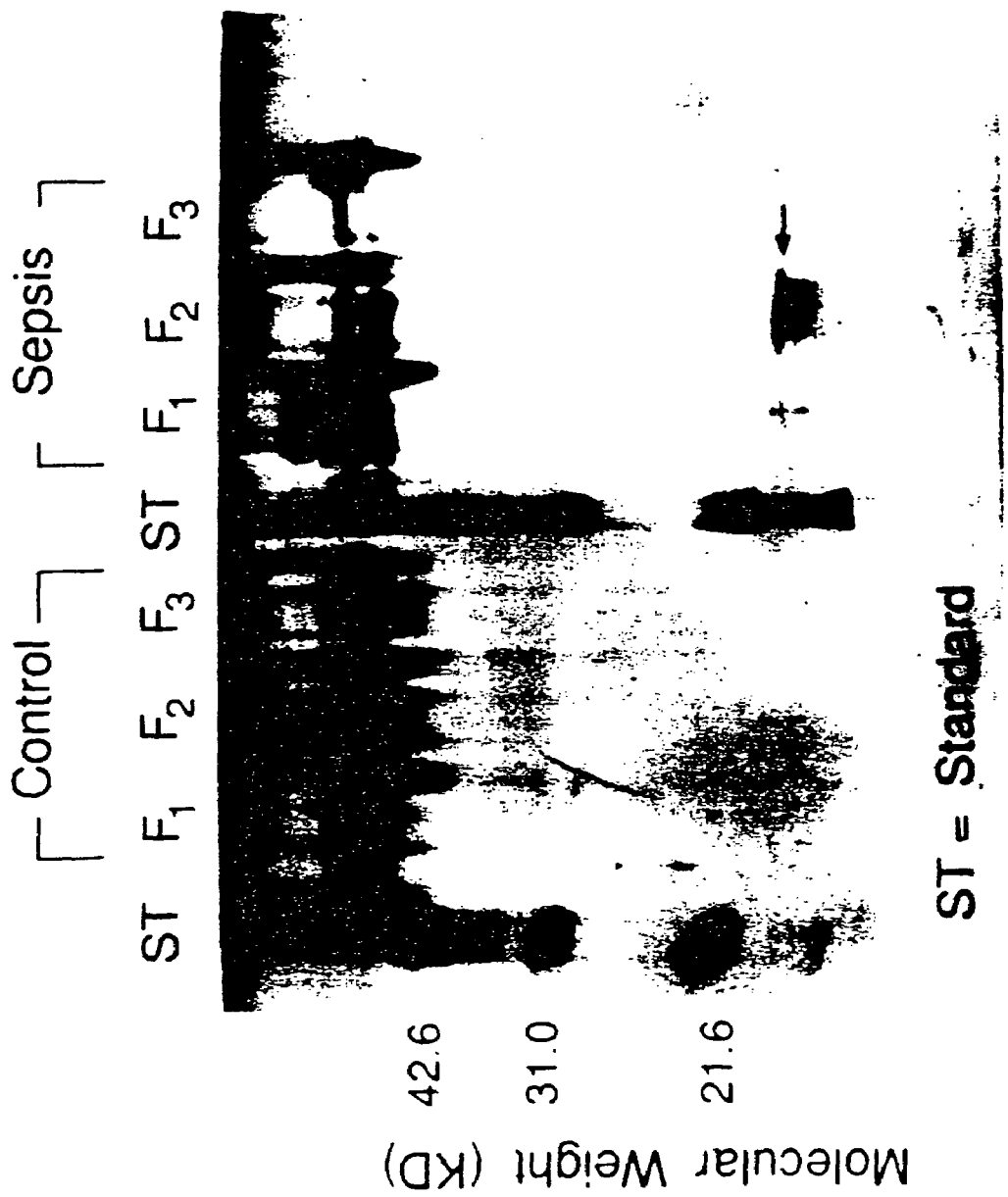

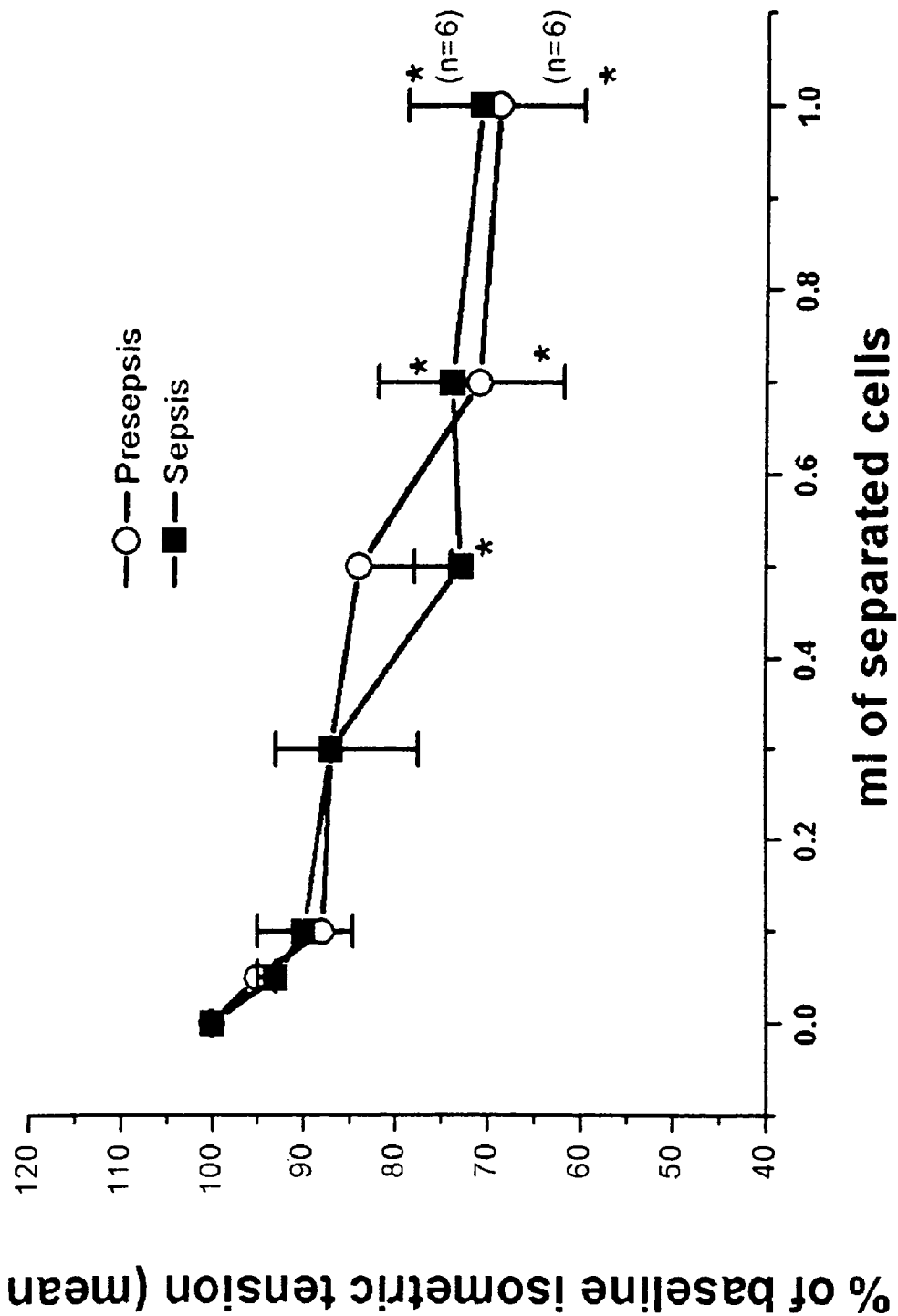

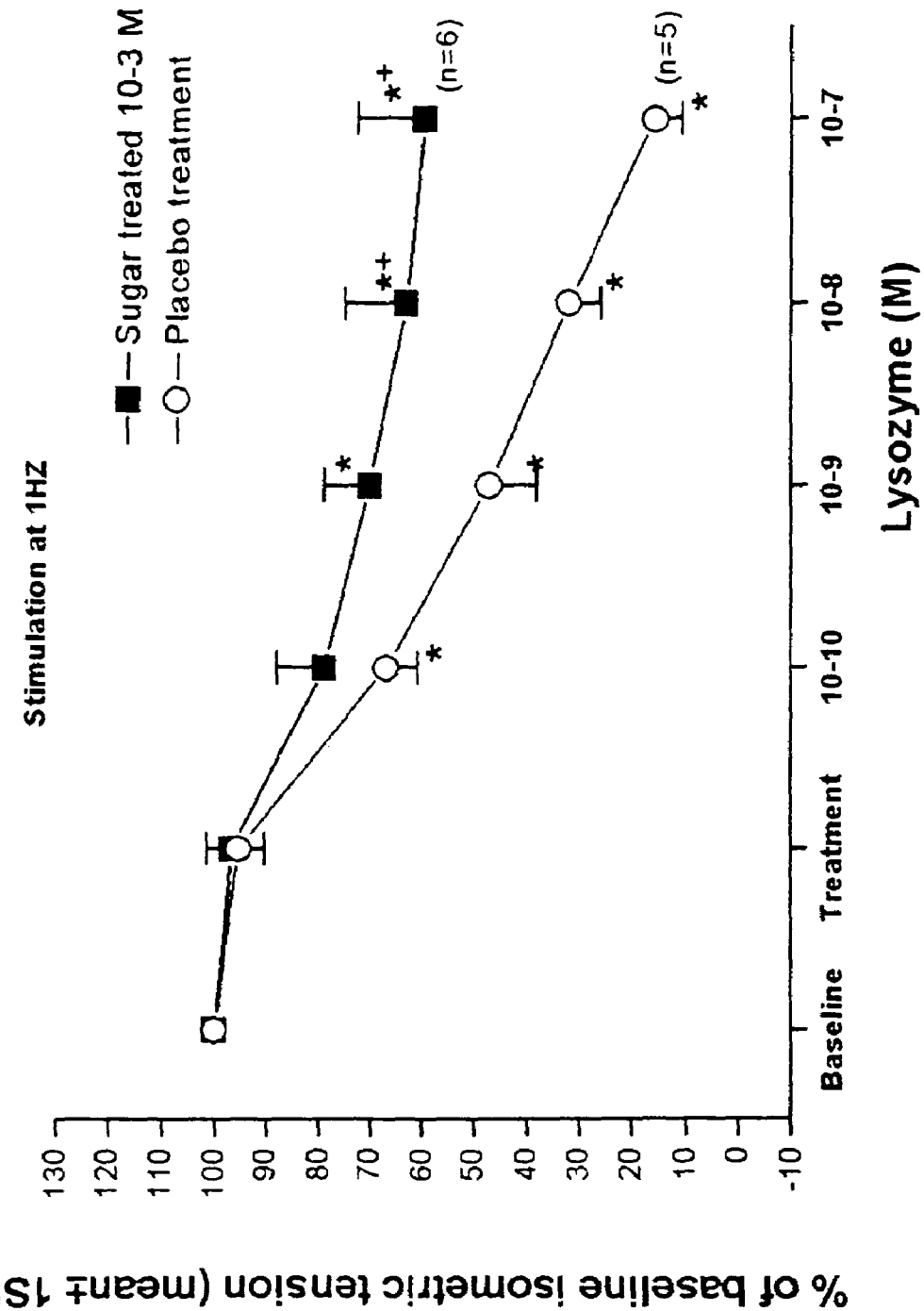

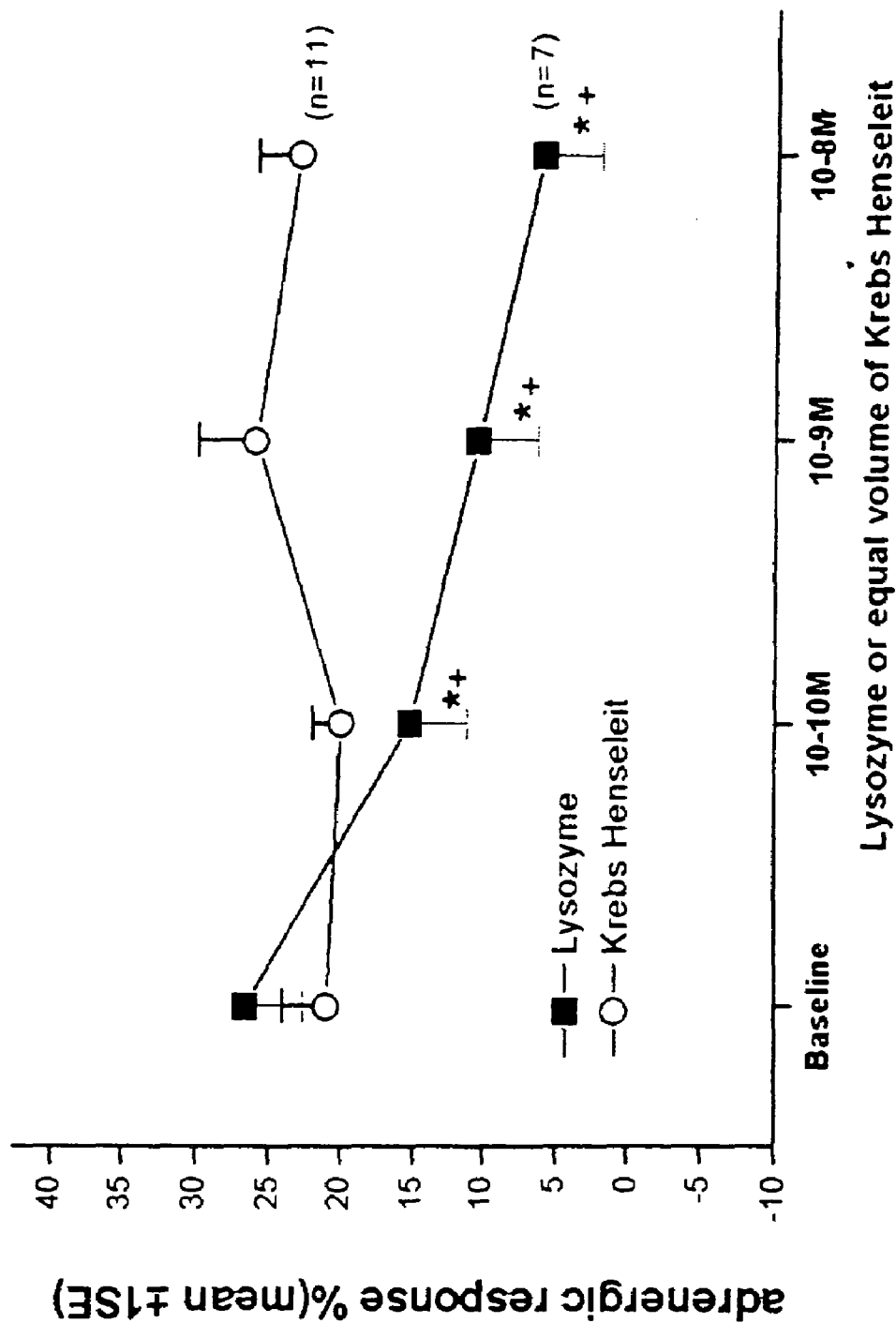

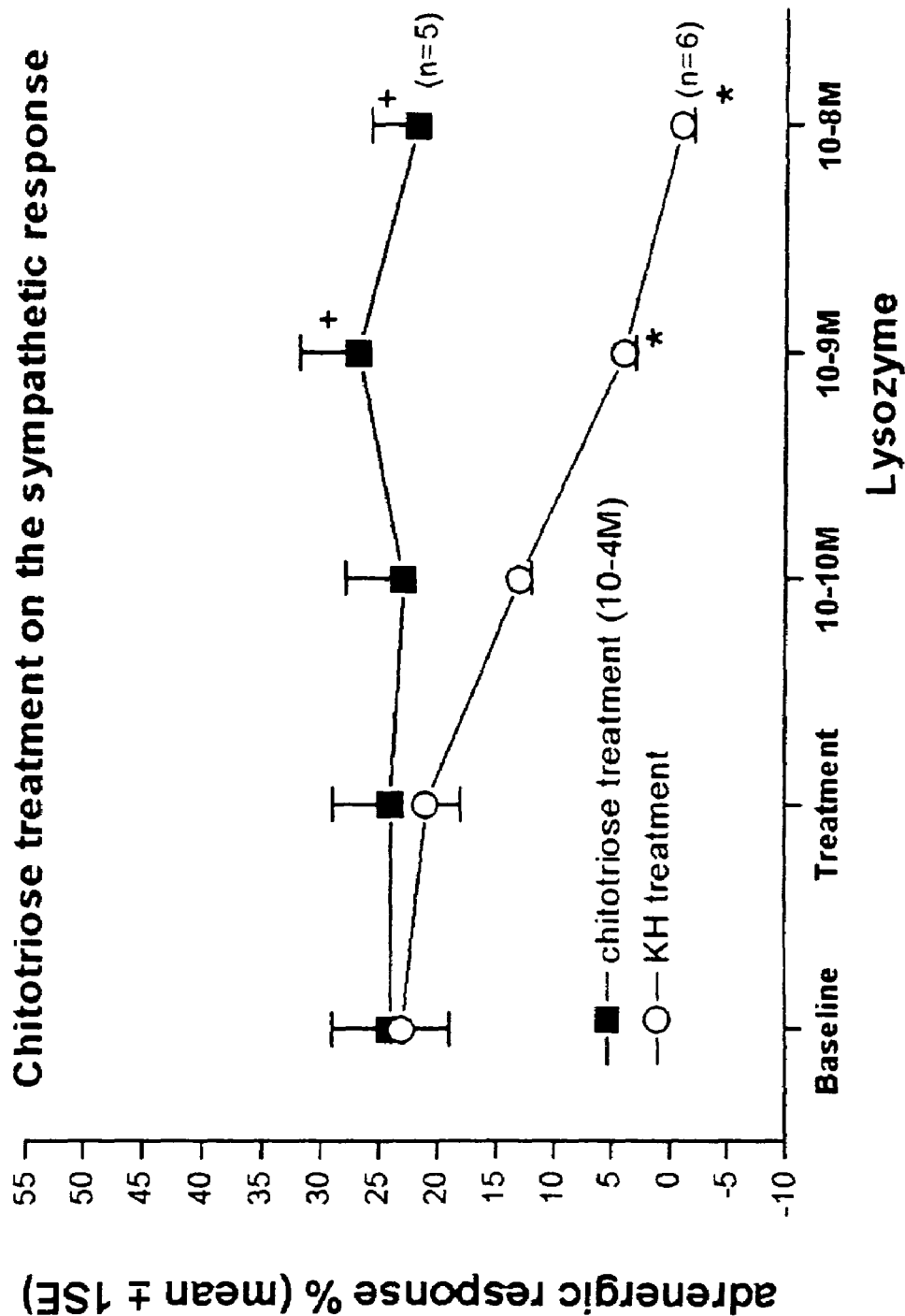

Pretreatment Study
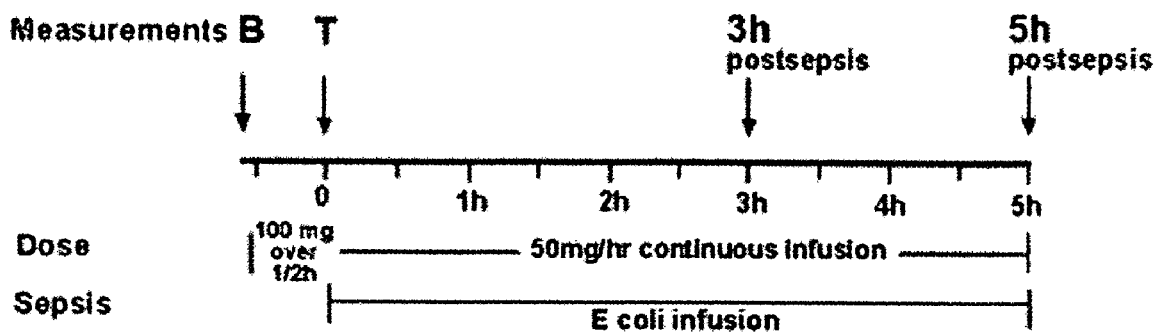
Late Treatment Study
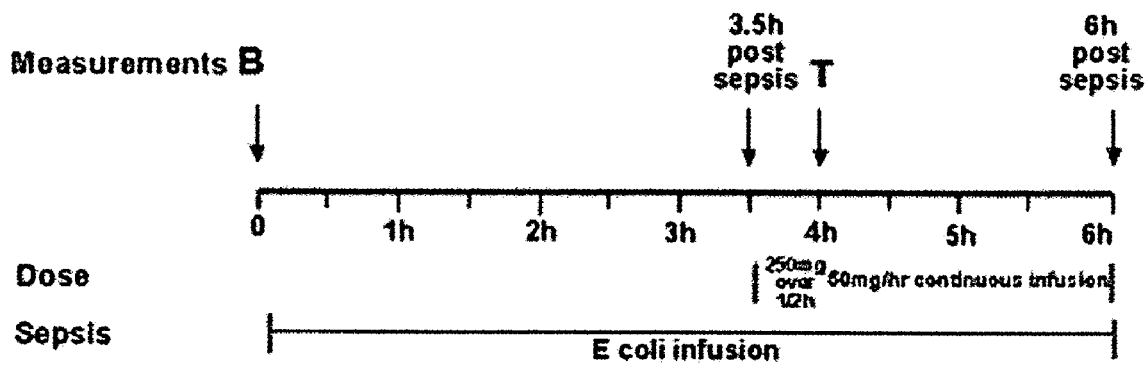
Early Treatment Study
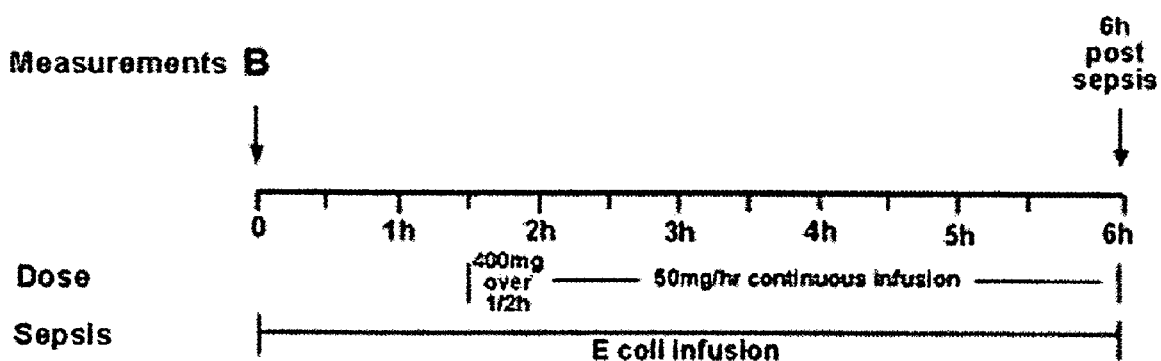
Figure 8

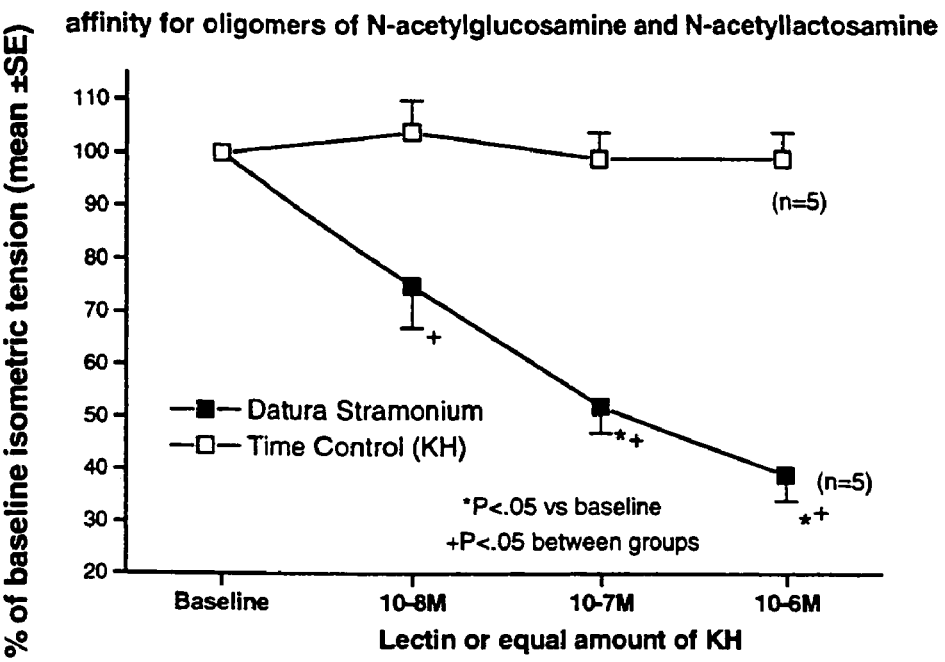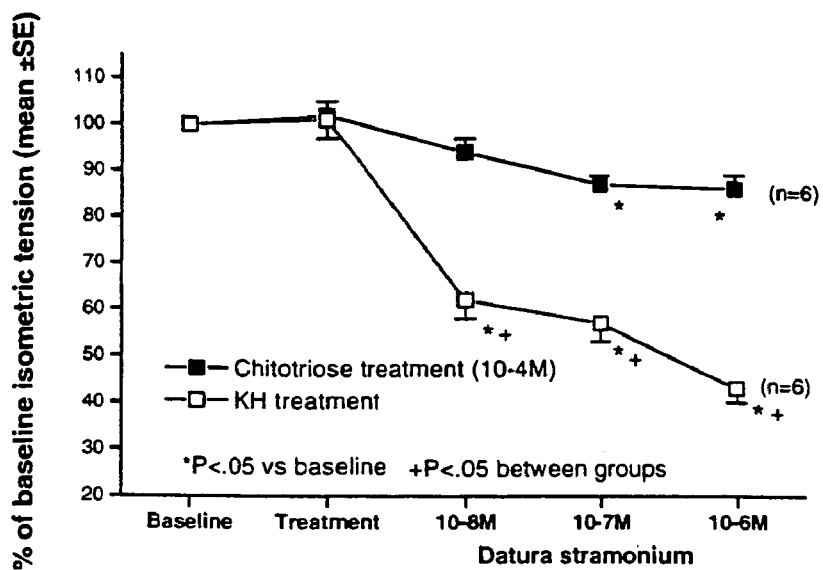
Figure 13

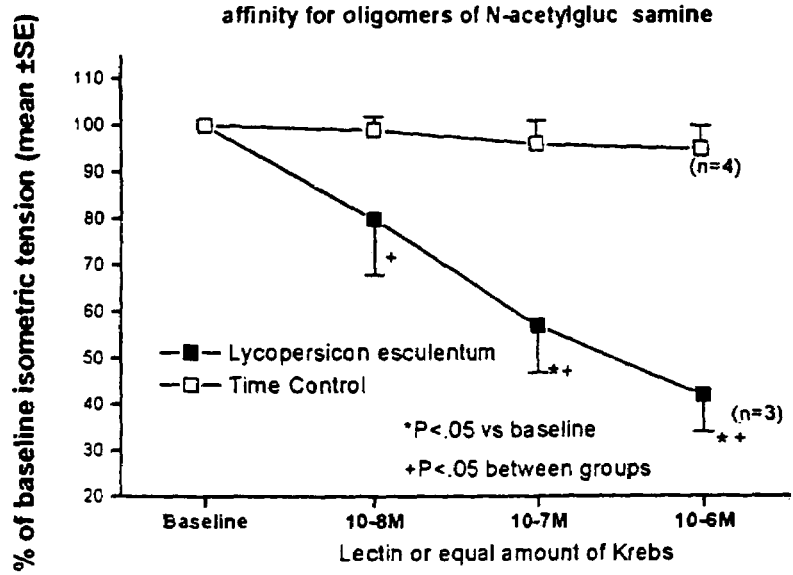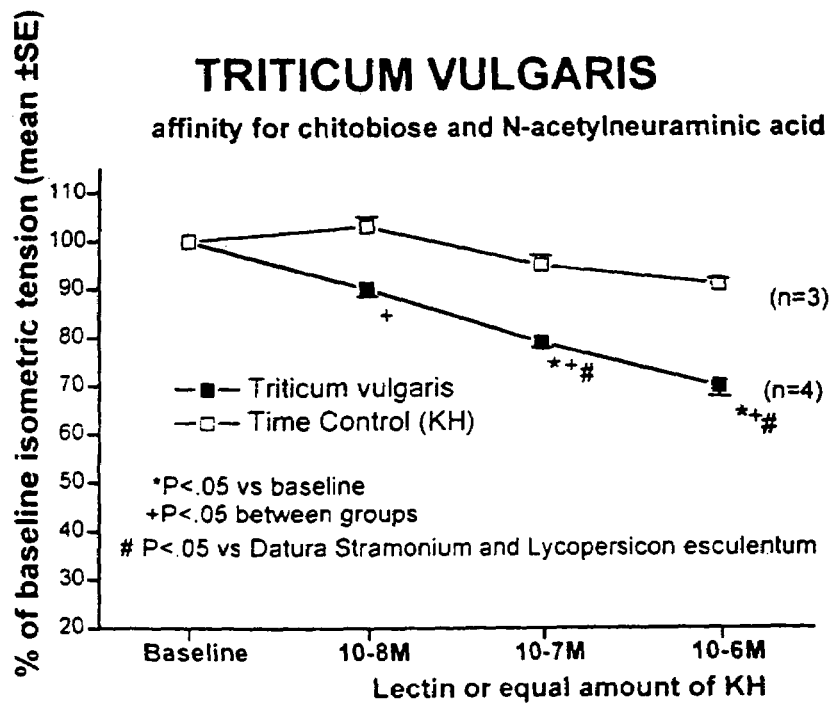
Figure 14

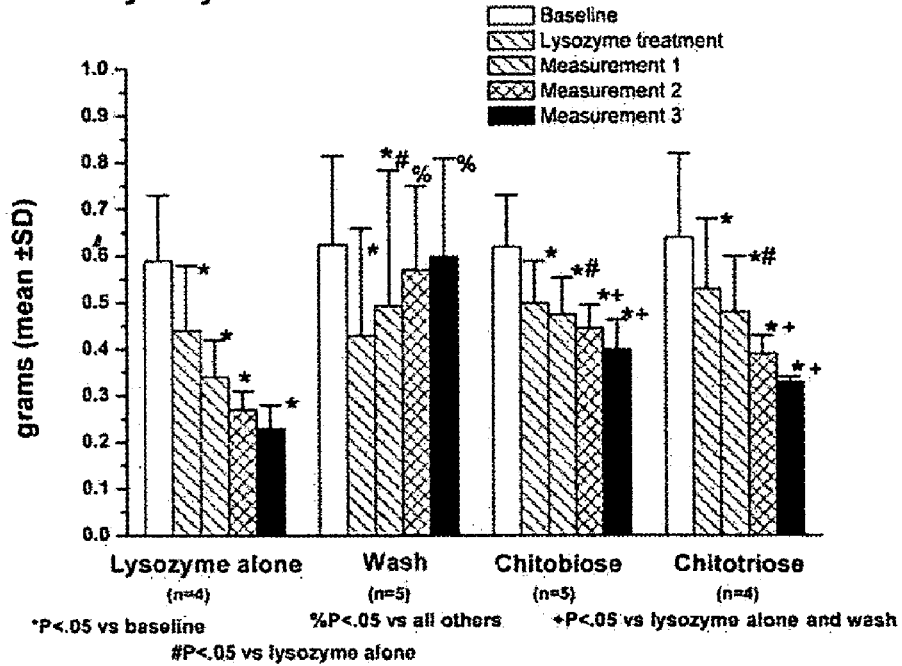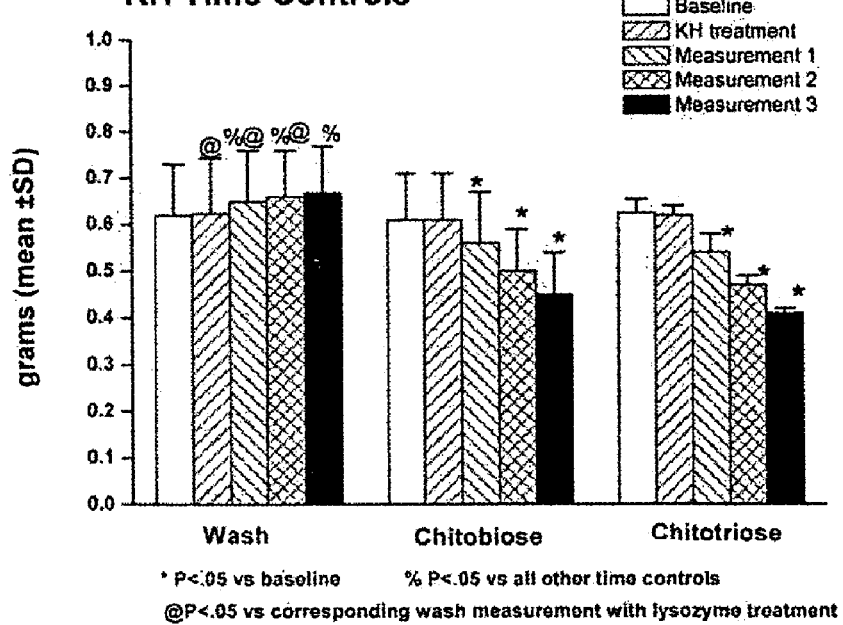
Figure 17

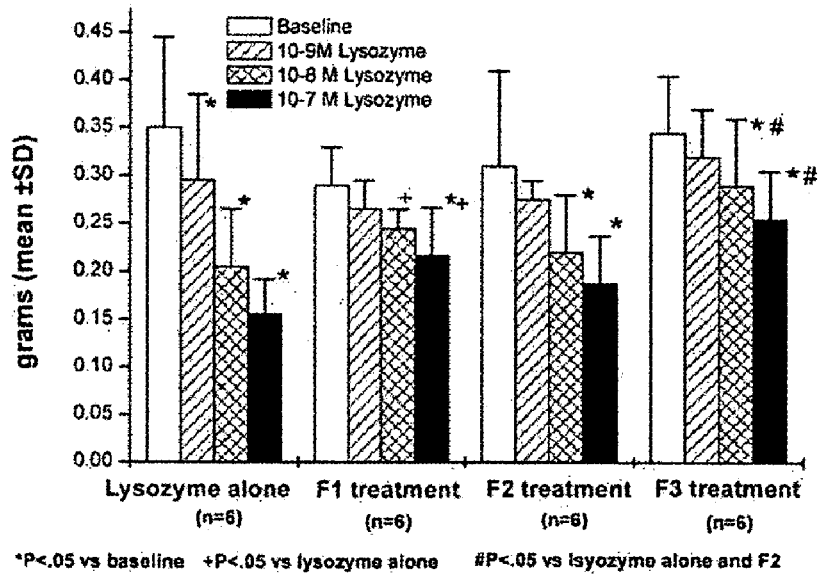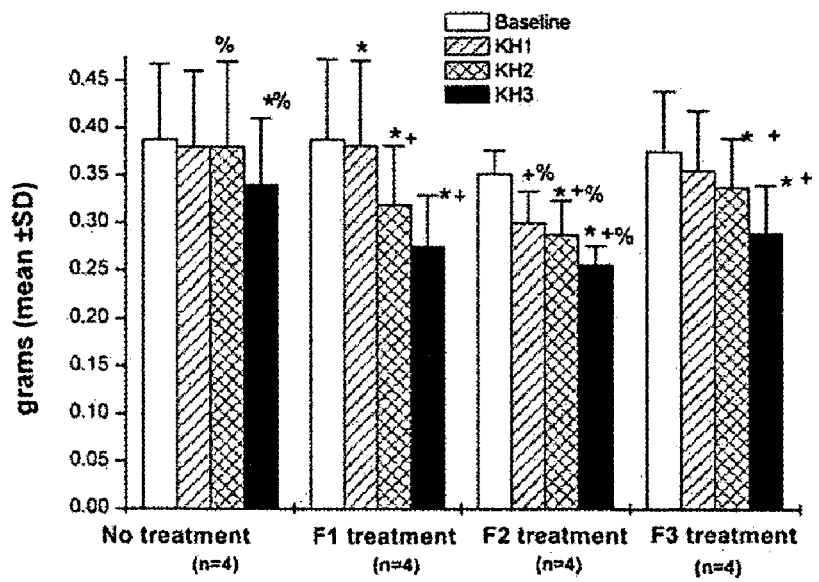
Figure 19

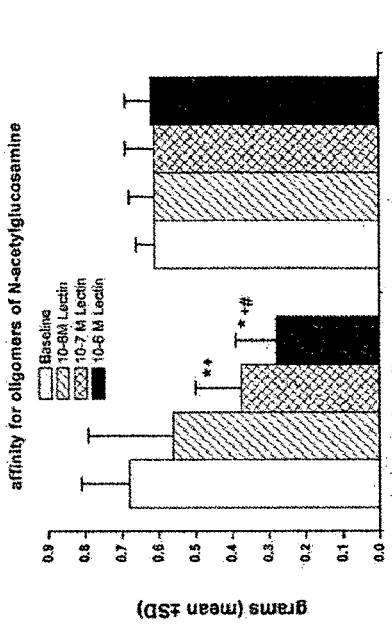
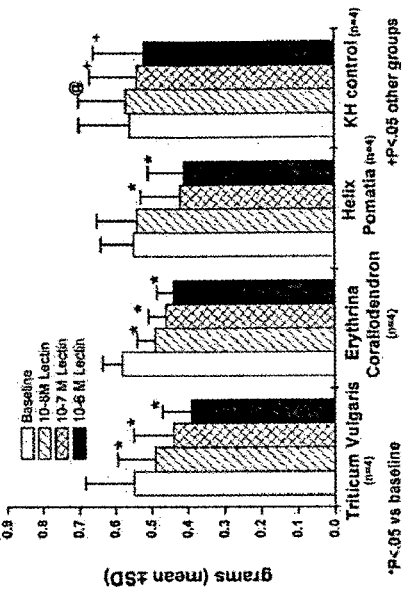
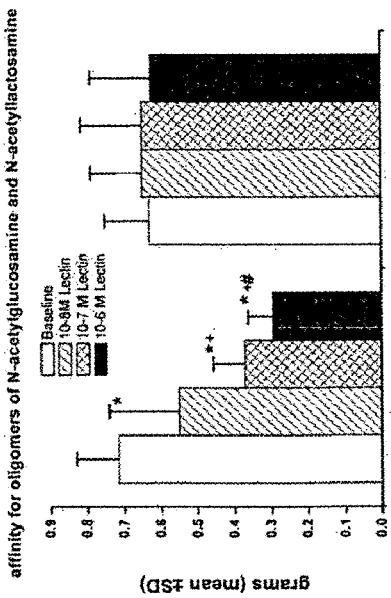
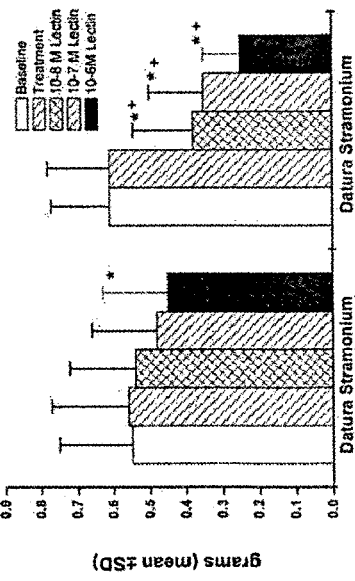
Figure 20

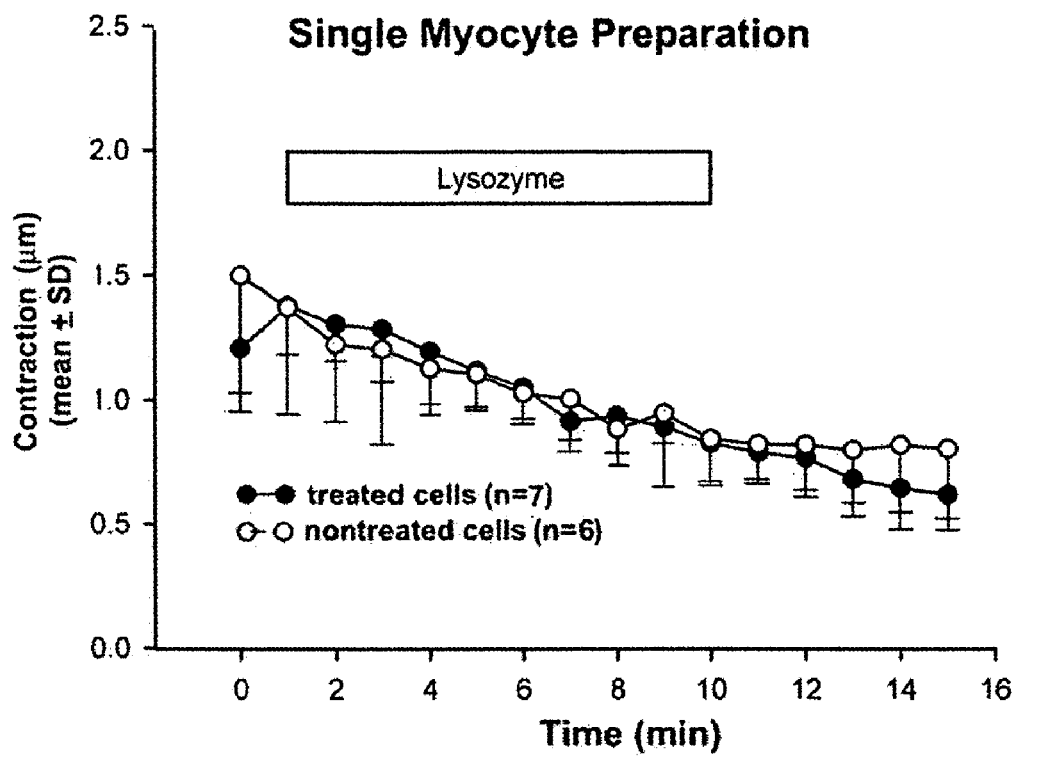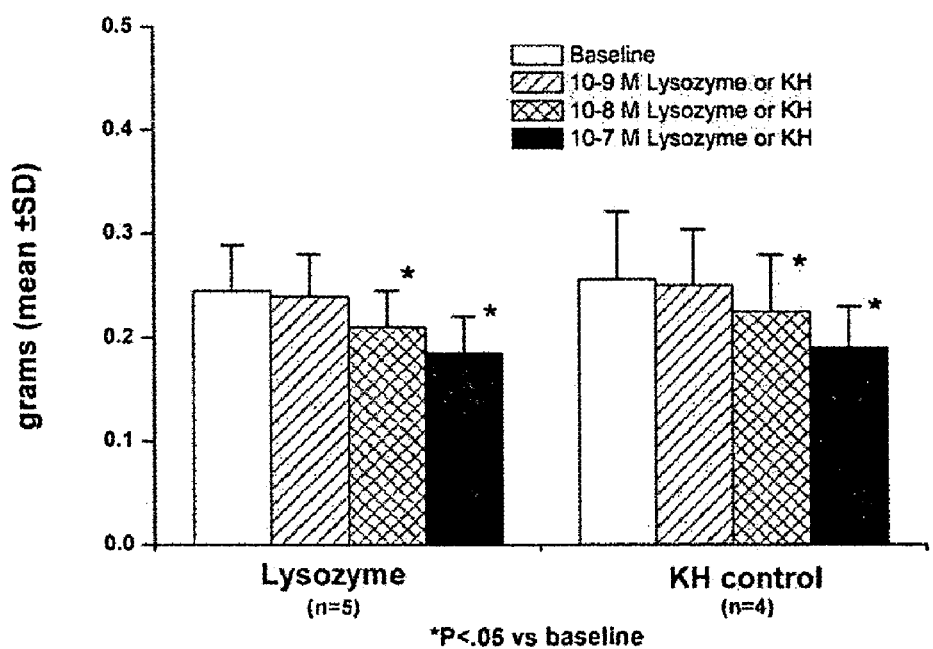
Figure 21

METHODS OF TREATING INFLAMMATION

This application claims the benefit under 35 USC §119(e) from U.S. Provisional patent application Ser. No. 60/442,060, filed Jan. 24, 2003, which is incorporated herein by reference in its entirety.

FIELD OF THE INVENTION

The invention relates to methods and compositions for treating myocardial dysfunction or inflammation by inhibiting lysozyme, an enzyme released during inflammatory response.

BACKGROUND OF THE INVENTION

Sepsis is a clinical syndrome that results from an activated systemic host inflammatory response to infection. In its more severe form, sepsis affects almost 800,000 North Americans each year, and results in the deaths of approximately 30% of these. It is the leading cause of morbidity for patients admitted to a contemporary intensive care unit (ICU), through the development of a syndrome of disseminated organ injury, known as the multiple organ dysfunction syndrome. Sepsis is characterized by an overwhelming systemic response to infection and may lead to septic shock. Septic shock is a life threatening immunological reaction to a severe infection. Septic shock is caused by the presence of large numbers of bacteria in the blood stream; symptoms include a fall in blood pressure, impaired ability of the blood to clot and damage to major organs including kidneys, liver and lungs.

Septic shock is becoming increasingly common in the North American population because of an increasing population at risk: a larger proportion of elderly individuals including many with chronic debilitating disease, and increasing numbers of people with impaired immunity due to disease such as cancer and AIDS. About 400,000 cases of sepsis, 200,000 cases of septic shock and 100,000 deaths from both occur each year in the U.S.

Researchers continue to experiment with medication to fight the infection and control the inflammatory response associated with sepsis and septic shock. However, the 50% mortality rate associated with septic shock has improved little in the last 30 years despite innovations in antibiotic therapy and life support modalities. To combat the condition, hospitals currently administer drugs and fluids to patients maintain blood pressure and use antibiotics to fight the infection.

Epidemiologic surveys have demonstrated that tissue injury secondary to activation of the inflammatory system may also complicate noninfectious disorders (e.g. acute pancreatitis and ischemia-reperfusion). The term systemic inflammatory response syndrome (SIRS) is used in this setting to refer to the consequences of a dysregulated host inflammatory response when infection is not present. SIRS is a widespread inflammatory response to a variety of severe clinical results.

It is important to distinguish between an underlying disease (infection or pancreatitis) and the host's response (sepsis or SIRS). This distinction is important clinically since it is the latter, not the primary disease, that is responsible for the multiple organ dysfunction syndrome (MODS). MODS is the usual explanation for the high mortality rates associated with these syndromes.

Several investigators have shown that a depression in cardiac contractility is an important component of hemodynamic collapse in sepsis (1,2). Some have attributed this cardiac dysfunction to a low molecular weight substance that is present in septic plasma (3-4). Lefer and coworkers suggested, on the basis of a large body of work, primarily in animal models of hemorrhagic shock, that myocardial depressant factor was a small molecular weight peptide originating from the pancreas (3,4). Others suggested that this substance was a cytokine released into the circulation as part of the inflammatory reaction induced by the infecting organism (5). However, there is no clear consensus about the origin or biochemical nature of myocardial depressant substance(s) in sepsis. Indeed, the very existence of such a factor has remained controversial.

The inventors previously provided additional evidence for the existence of a myocardial depressant factor in sepsis (6). In an *Escherichia coli* model of induced sepsis in dogs, Gomez et al (6) showed that myocardial depression developed after 4 h of bacteremia and that this depression could be reversed by removal of a circulating substance of <30,000 molecular weight from the plasma by continuous arteriovenous hemofiltration. Myocardial depressant activity in plasma [filterable cardiodepressant substance (FCS)] was detected by a bioassay that included a right ventricular trabecular preparation. FCS activity was detected in the plasma as early as 1 h after sepsis and increased further at the 4 h interval. Hemofiltration returned FCS activity to preseptic levels.

In a subsequent study, the inventors further characterized the nature of FCS (7). By pore filtration techniques, the inventors found that FCS was contained in the 10-30 kilodalton (KD) fraction of plasma, was found in the acetone-insoluble portion of plasma, and that its activity could be diminished by the proteolytic enzyme proteinase-K. This suggested that FCS was likely to be a protein.

SUMMARY OF THE INVENTION

The present inventors have purified the filterable cardiodepressant substance (FCS) and determined its identity using microcapillary reverse phase high pressure liquid chromatography (HPLC), tandem mass spectrometry (MS/MS) and protein sequencing techniques. The results indicated that this protein is lysozyme c (Lzm-S). The inventors further determined that lysozyme c decreased myocardial contraction and the adrenergic response to neural stimulation and the β-agonist isoproterenol in respective right ventricular trabecular preparations. The inventors also showed that these effects could be blocked by a competitive inhibitor of lysozyme, the results providing further evidence that lysozyme may be important in the pathophysiology of myocardial dysfunction in sepsis.

Accordingly, the present invention provides a method of preventing or inhibiting myocardial dysfunction comprising administering an effective amount of an agent that can inhibit lysozyme to an animal in need thereof. The animal is preferably one with sepsis.

The present invention also provides a method of treating an inflammatory condition comprising administering an effective amount of an agent that can inhibit lysozyme to an animal in need thereof.

In a specific embodiment, the agent that can inhibit lysozyme is a competitive inhibitor such as N,N',N" triacetylglucosamine (TAC, also referred to as chitotriose) or N,N' diacetylglucosamine (chitobiose).

The present invention also provides a method of reversing myocardial depression in an animal with sepsis comprising administering an effective amount of an agent that can inhibit lysozyme to the animal.

In a specific embodiment, the agent that can inhibit lysozyme is a competitive inhibitor such as chitobiose (N, N' diacetylglucosamine).

The present invention also includes pharmaceutical compositions for use in treating an inflammatory condition or in preventing or inhibiting myocardial dysfunction comprising an effective amount of an agent that can inhibit lysozyme in admixture with a suitable diluent or carrier.

In a further embodiment, the present invention also includes a method of identifying substances which can bind to lysozyme comprising the steps of:

(a) reacting lysozyme and a test substance, under conditions which allow for formation of a complex between the lysozyme and the test substance, and (b) assaying for complexes of lysozyme and the test substance, for free substance or for non complexed lysozyme, wherein the presence of complexes indicates that the test substance is capable of binding lysozyme.

Other features and advantages of the present invention will become apparent from the following detailed description. It should be understood, however, that the detailed description and the specific examples while indicating preferred embodiments of the invention are given by way of illustration only, since various changes and modifications within the spirit and scope of the invention will become apparent to those skilled in the art from this detailed description.

BRIEF DESCRIPTION OF THE DRAWINGS

The invention will now be described in relation to the drawings in which:

FIGS. 1A, 1B and 1C are graphs showing plasma fractions were divided into three components by SEC-HPLC techniques. Aliquots of the presepsis and septic plasma fractions were placed into the right ventricular trabecular preparation and the decrease in isometric tension (mean±SE) as compared with baseline was measured. There was a significant increase in depressant activity in the F2 septic fraction as compared with the nonseptic plasma fraction, while the other fractions showed no increase in activity after sepsis. Note that even in the preseptic sample, there is some background depressant activity (BDA) that is found in all samples, but BDA appears to be of lipid moiety with different physical properties as compared with FCS (7). For this reason, it has been our approach in defining the nature of FCS to compare pre and septic plasma fractions taken from the same dog. An increase in depressant activity found in a sepsis fraction relative to that found in the presepsis fraction is indicative of the formation of FCS. By two way ANOVA and SNK, *$P<0.05$ vs baseline; +$P<0.05$ septic vs presepsis fraction.

FIG. 2 shows a one dimensional-gel electrophoresis. The control (i.e. presepsis) F1, F2, and F3 plasma fractions are shown in the left lanes, while the septic fractions are shown in the right lanes. A broad band is observed in the F2 septic plasma fraction at approximately 15 KD that was not observed in the presepsis plasma fraction. ST is standard.

FIGS. 3A, 3B and 3C are graphs showing that FCS activity was measured in the spleen, the proposed source of FCS, as well as the heart, the proposed target organ of FCS (see Example 1). In addition, FCS activity was measured in lymphocytes, a cell type that would not be associated with production of this protein and would therefore serve as a negative control. Neutrophils, another source of FCS were not measured, since these cells would be found in the spleen. Mean (±1SE) myocardial depressant activity measured in the in vitro preparation was increased in hearts and spleens taken from septic animals as compared with nonseptic animals, while there was no change of activity in lymphocytes. By two way ANOVA and SNK, *$P<0.05$ vs baseline; +$P<0.05$ sepsis vs presepsis.

FIGS. 5A, 5B and 5C are graphs showing the effect of TAC (chitotriose) on lysozyme activity. The effect of TAC on attenuating lysozyme induced depressant activity was examined at 0.5 Hz (FIG. 5A) and 1 Hz (FIG. 5B). Either TAC or KH placebo was placed into the bath before the addition of lysozyme in respective groups. The TAC treated group showed less depression than the nontreated group. In FIG. 5C, TAC was placed into the in vitro preparation after the addition of lysozyme. TAC treatment attenuated the decline in tension as compared with the nontreated (KH) group. By two way ANOVA and SNK, *$P<0.05$ vs baseline; +$P<0.05$ treated vs nontreated groups.

FIGS. 7A, 7B and 7C are graphs showing the mean (±1SE) values obtained for the adrenergic response. In FIG. 7A, lysozyme decreased the adrenergic response as compared with the time control group. In FIG. 7B, TAC treatment prevented the decrease in adrenergic response observed with lysozyme. In FIG. 7C, lysozyme also decreased the response to the β-agonist isoproterenol in the right ventricular trabecular preparation. *$P<0.05$ vs baseline; +$P<0.05$ between groups.

FIG. 8 shows the protocols of the different studies in which the measurement intervals, dose of N,N',N" triacetylchitotriose (TAC), and time of sepsis are indicated. In the Pretreatment Study, measurements were obtained at baseline (B), after treatment (T), and after 3 h and 5 h of sepsis. In the Late Treatment Study, measurements were obtained at B, after 3.5 h sepsis, after T, and after 2 h of continuous treatment (i.e. 6 h post-sepsis). In the Early Treatment Protocol, measurements were obtained at B and after 6 h of sepsis. In the Early Treatment Study, we did not make measurements immediately after treatment was given (i.e. the 2 post sepsis period). The rationale for not making measurements at the 2 h period was that myocardial depression would not yet have developed at this interval, so that no effect of TAC would have been apparent.

Figure 9:
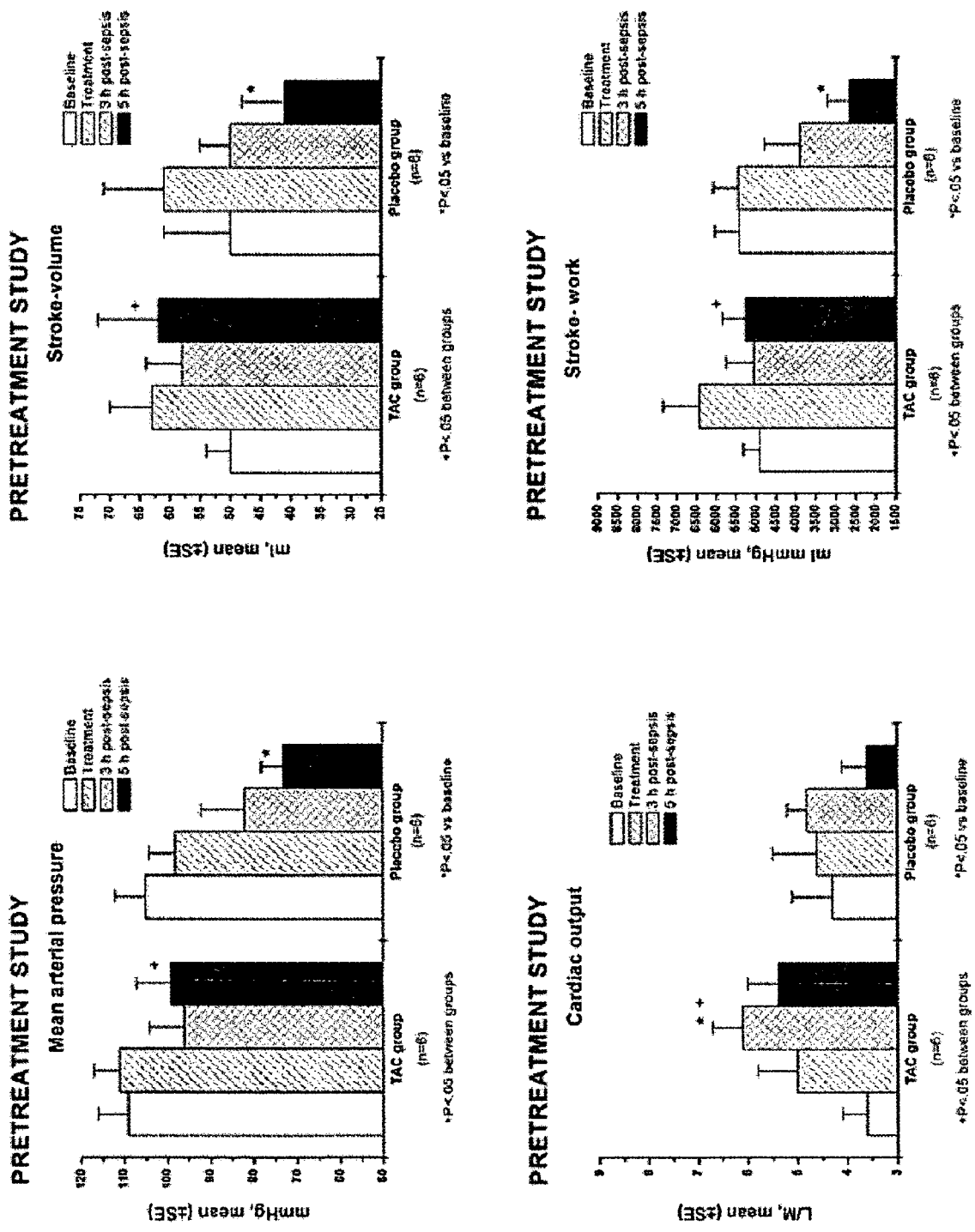

FIG. 9 is a series of graphs showing hemodynamics for the treated and nontreated groups at the different measurement intervals in the Pretreatment Study. At the 5 h interval, pretreatment with N,N',N" triacetylchitotriose (TAC) resulted in significant increases in mean arterial pressure, stroke-volume, and stroke-work as compared with the nontreated group. *P<0.05 vs baseline within a group by one way ANOVA and SNK; +P<0.05 treated vs nontreated groups, in which the change from baseline was compared between the two groups by two way repeated measures ANOVA and SNK.

Figure 10:
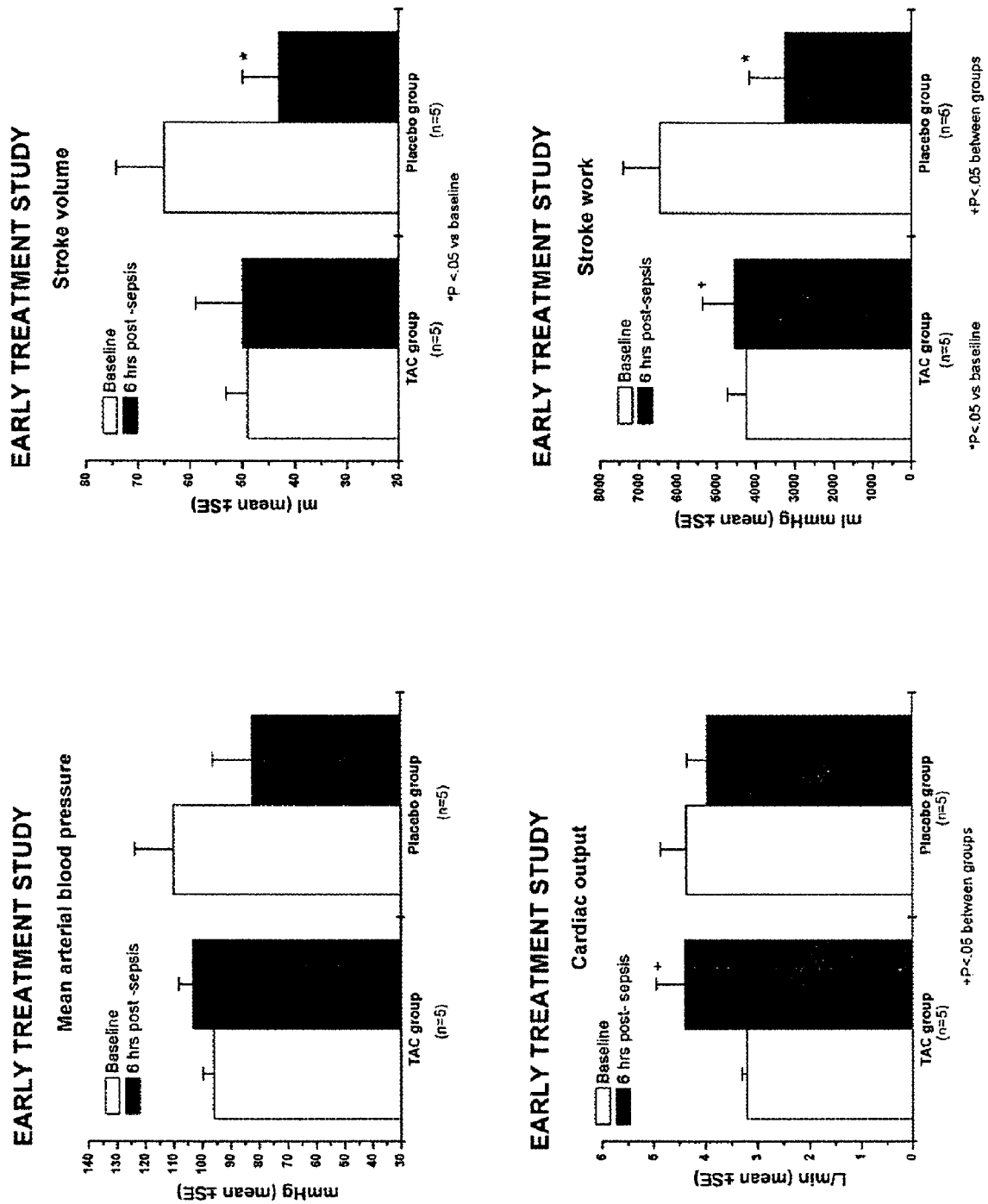

FIG. 10 is a series of graphs showing hemodynamics for the treated and nontreated groups at the different measurement intervals in the Early Treatment Study. At the 6 h interval, treatment with N,N',N" triacetylchitotriose (TAC) resulted in significant increases in cardiac output and stroke-work as compared with the nontreated group. *P<0.05 vs baseline within a group by one way ANOVA; +P<0.05 between groups by two way ANOVA in which the response to sepsis (A×B interaction) was significantly different between the two groups (factor A) over the 6 h period (factor B).

Figure 11:
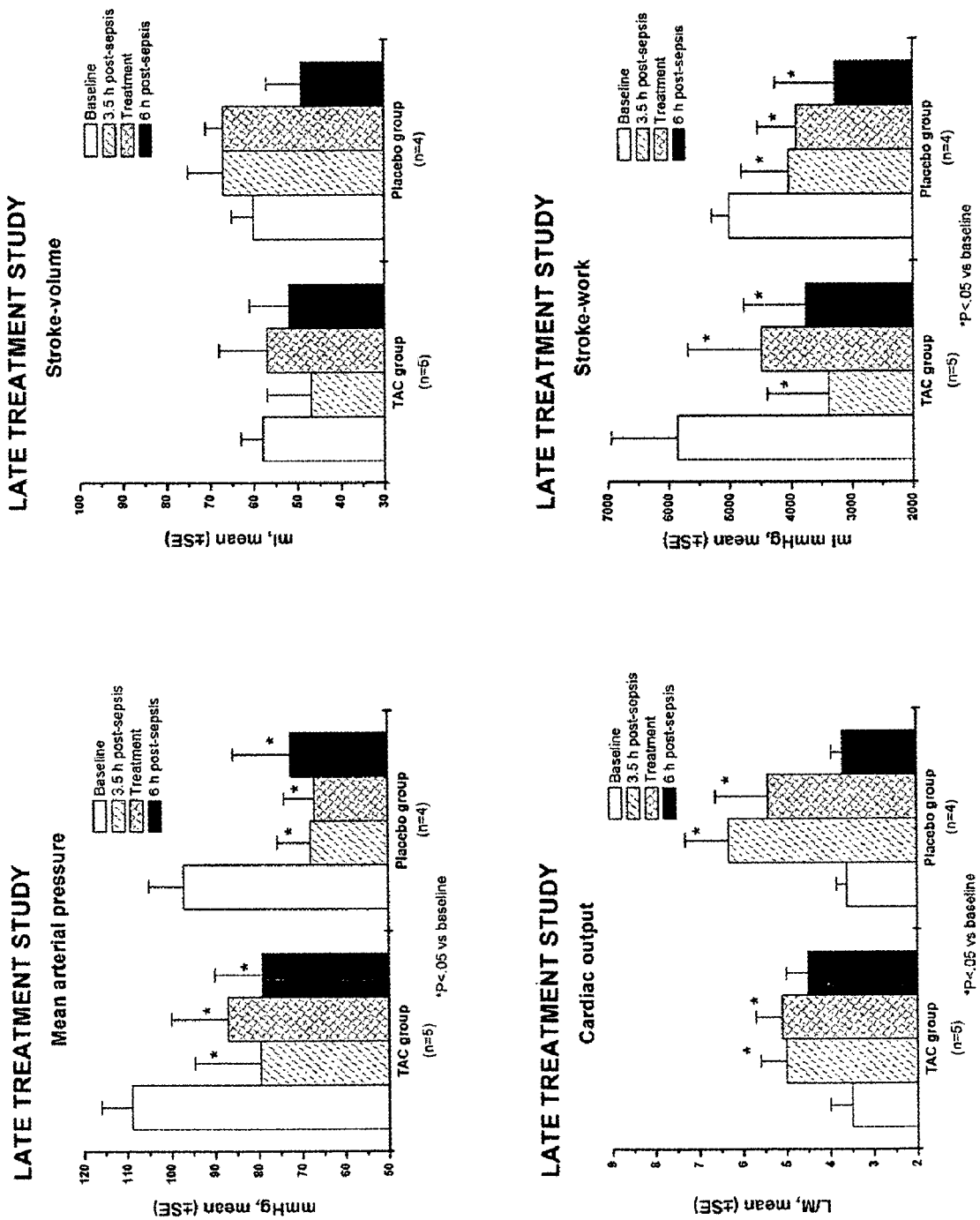

FIG. 11 is a series of graphs showing hemodynamics for the treated and nontreated groups at the different measurement intervals in the Late Treatment Study. There was no effect of N,N',N" triacetylchitotriose (TAC) on hemodynamics in this study. *P<0.05 vs baseline within a group by one way ANOVA and SNK.

Figure 12:
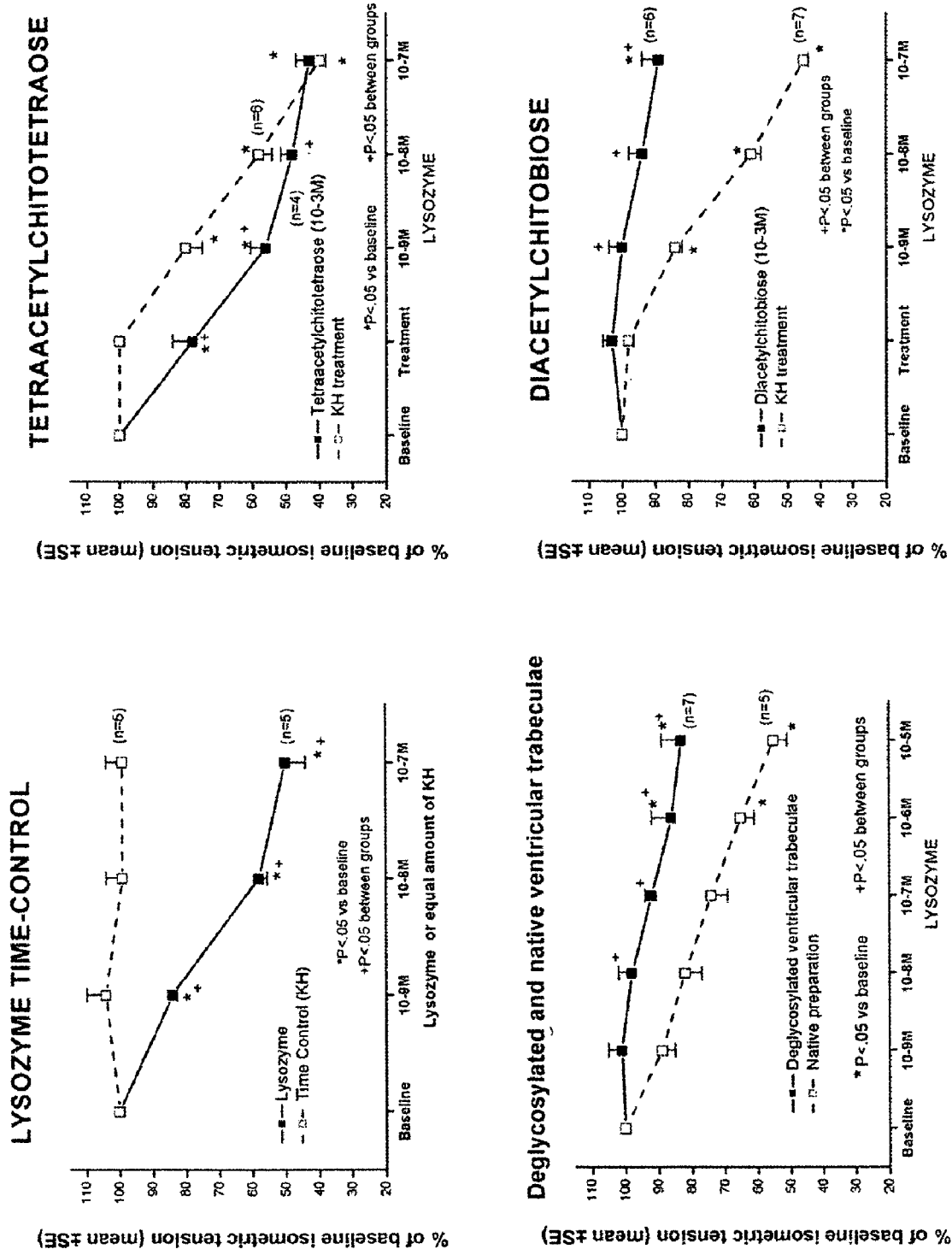

FIG. 12 is a series of graphs. In the left upper panel, the effects of various concentrations of lysozyme on isometric tension are shown in the in vitro preparation. As compared to a time control group in which an equal volume of Krebs Henseleit (KH) solution was added to the preparation, lysozyme caused a marked reduction in isometric tension at the concentrations tested. In the left lower panel, the effect of lysozyme on isometric tension in deglycosylated and native ventricular trabeculae is shown. In the native muscle, lysozyme produced a marked decline in isometric tension, while in the deglycosylated muscle the reduction in isometric tension was attenuated as compared with the native muscle. When N,N',N",N''' tetraacetylchitotetraose (right upper panel) was added to the preparation, there was no inhibitory effect on lysozyme's depressant activity; in fact the depressant effect of lysozyme was greater than that found without treatment. However, N,N' diacetylchitobiose (right lower panel) completely blocked lysozyme's depressant activity. *P<0.05 vs baseline by one way ANOVA and SNK; +P<0.05 between groups by two way ANOVA and SNK.

FIG. 13 consists of two graphs. In the upper panel, percent isometric tension is plotted on the ordinate against *Datura stramonium* lectin concentration or equal volume of Krebs Henseleit solution (KH) on the abscissa. *Datura stramonium* lectin caused a marked decrease in isometric tension as compared with the time control group. In the lower panel, pretreatment of the preparation with TAC (chitotriose) blocked the isometric depression as compared with the nontreated preparation. *P<0.05 vs baseline; +P<0.05 between groups by two way ANOVA and SNK.

FIG. 14 consists of two graphs. In the upper panel, percent isometric tension is plotted on the ordinate against *Lycopersicon esculentum* lectin or equal volume of Krebs Henseleit solution (KH) on the abscissa. *Lycopersicon esculentum* caused a marked decrease in isometric tension as compared with the time control group. In the lower panel, *Triticum vulgaris* lectin produced a lesser degree of depression than that found with *Datura Stramonium* lectin and *Lycopersicon esculentum* lectin. *P<0.05 vs baseline; +P<0.05 between groups by two way ANOVA and SNK. #P<0.05 vs *Datura Stramonium* lectin and *Lycopersicon esculentum* lectin in which the change in tension from baseline was compared among the three groups by two way ANOVA and SNK.

Figure 15:
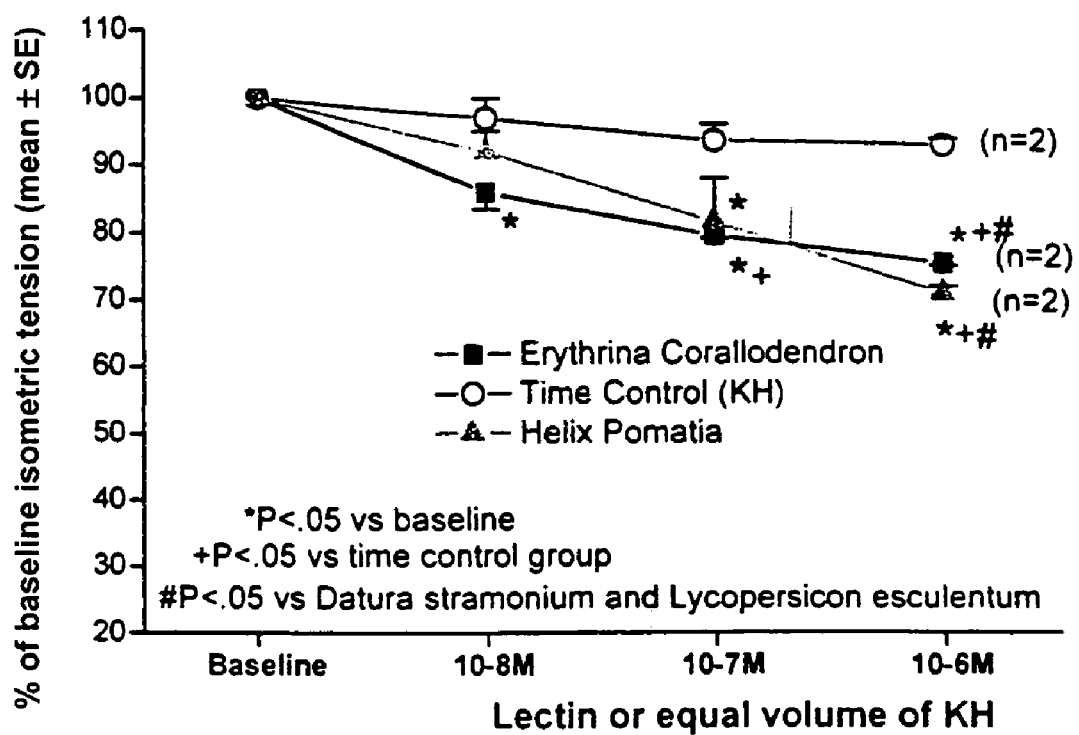

FIG. 15 is a graph. Percent isometric tension is plotted on the ordinate against *Erythrina corallodendron* lectin, *Helix pomatia* lectin, or Krebs Henseleit solution on the abscissa. Both *Erythrina corallodendron* lectin and *Helix pomatia* lectin produced a lesser degree of depression than that found with *Datura stramonium* lectin and *Lycopersicon esculentum* lectin. *P<0.05 vs baseline; +P<0.05 between groups by two way ANOVA and SNK. #P<0.05 vs *Datura stramonium* lectin and *Lycopersicon esculentum* lectin in which the change in tension from baseline was compared among the three groups by two way ANOVA and SNK.

Figure 16:
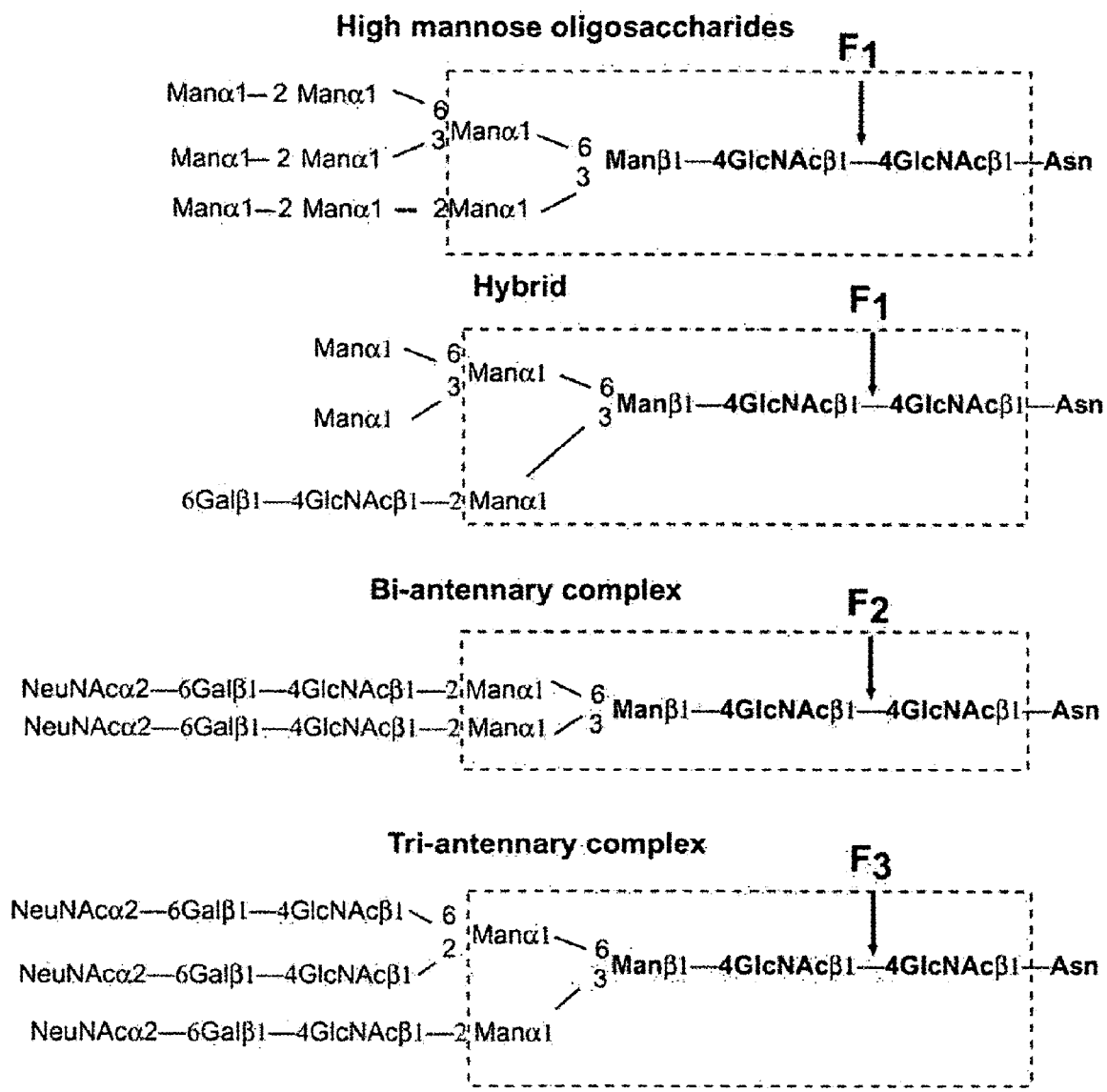

FIG. 16 shows various carbohydrates. Carbohydrates may be classified into high-mannose oligosaccharides, hybrid, and complex types. Of the complex types described, bi-antennary and tri-antennary structures are shown in the figure. The dotted box shows the tri-mannosyl core. Man is mannose; GlcNAc is N-acetylglucosamine; NeuNAc is N-acetylneuramic acid; Gal is galactose, and Asn is asparagine. GlcNAcβ1-4GlcNAc is the chitobiose residue in the core. Results suggest that lysozyme binds to the Manβ1-4GlcNAcβ1-4GlcNAc moiety in the core structure (see bolded residues in figure; see Example 4 for discussion).

The three endo-β-N-acetylglucosaminidases, endo-$F_1$, endo-$F_2$, and endo-$F_3$ have specificities for distinct oligosaccharide structures and cleave the chitobiose structure (see arrows). The results indicate that Lzm-S binds to the high mannose/hybrid and tri-antennary carbohydrate structures (see text).

FIG. 17 consists of 2 graphs showing the results of reversibility experiments, wherein isometric tension obtained in the right ventricular trabecular preparation is plotted on the ordinate against measurement interval for lysozyme treated (upper panel) and Krebs-Henseleit (KH) treated groups. In the lysozyme treatment alone group (upper panel), no intervention was performed and isometric tension fell over the three measurement intervals performed fifteen minutes apart. In the lysozyme group in which repeated washes with KH were performed, isometric tension was restored to baseline levels. In the chitobiose and TAC (chitotriose) groups, $10^{-3}$M of the respective inhibitors were instilled at each measurement interval, and the fall in isometric tension was attenuated as compared to the lysozyme treatment alone group. In the lower panel, repeated washes had no effect on isometric tension in the KH treated group. TAC (chitotriose) and chitobiose resulted in a modest decrease in isometric tension by themselves that may have contributed to the lack of complete reversal of depression by these inhibitors shown in the upper panel.

Figure 18:
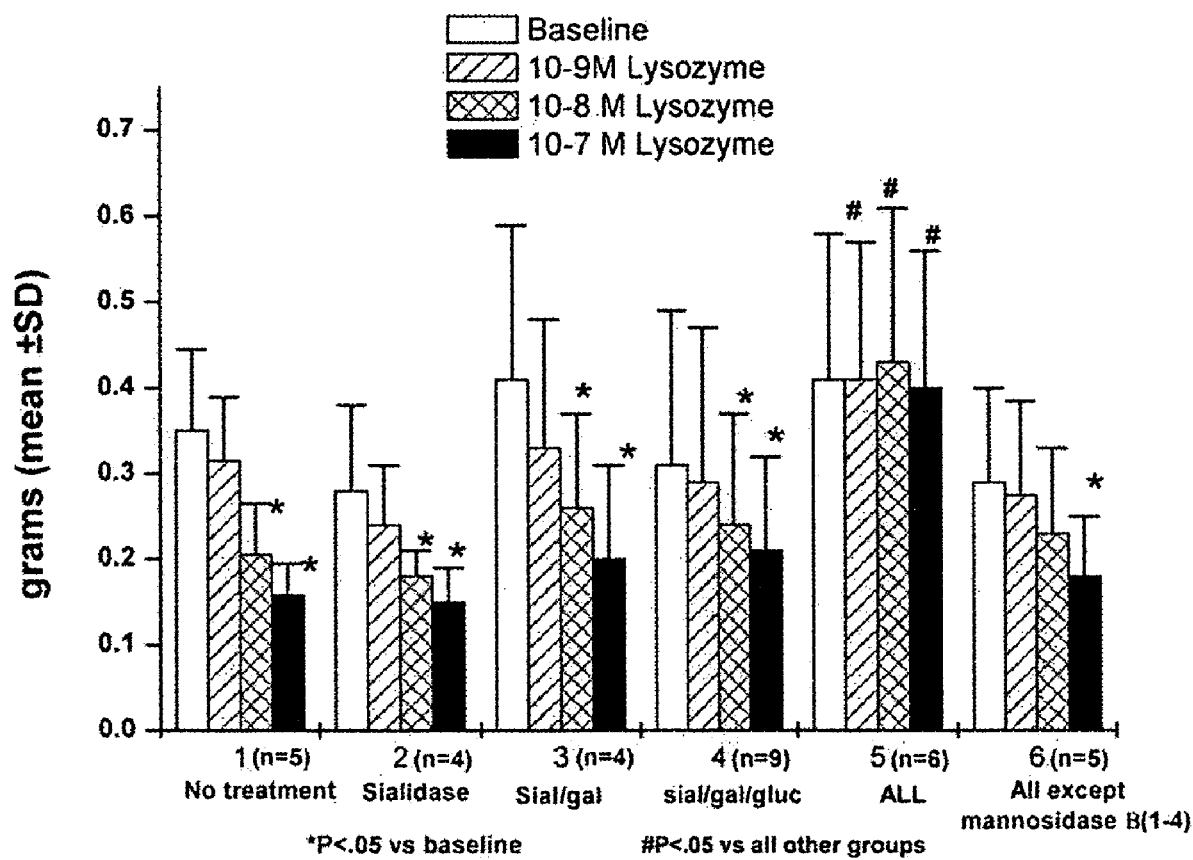

FIG. 18 is a graph showing the results of exoglycosidase experiments, wherein isometric tension measured in the right ventricular trabecular preparation is plotted on the ordinate. In group 1, no enzymes were added, and lysozyme was instilled at $10^{-9}$M, $10^{-8}$M, and $10^{-7}$M at five minute intervals. In group 2, a sialidase was added to remove any N-acetylneuramic acids present and no difference in isometric tension was noted as compared to group 1; in group 3, both sialidase and galactosidase were added to remove any N-acetylneuramic and galactose residues and no change was noted as compared with group 1; in group 4, the enzymes administered consisted of a sialidase, galactosidase, and a glucosaminidase, and no significant effect was observed as compared to the preceding groups; in group 5, in addition to the latter enzymes, α and β(1-4) mannosidases and fucosidases were added, and lysozyme's depressant activity was completely eliminated; in group 6, the β1-4 mannosidase was omitted from the enzyme mixture used in group 5, and the depressant activity increased to that found in groups 1-4.

FIG. 19 consists of 2 graphs. The effect of lysozyme (upper panel) on isometric tension is shown for the respective groups of ventricular trabeculae bathed with the three endo-β-N-acetylglucosaminidases. Endo-$F_1$ and endo-$F_3$ attenuated isometric tension to the greatest extent, while endo-$F_2$ had no significant effect. In the lower panel, when Krebs Henseleit solution (KH) rather than lysozyme was added to the preparation, there was a modest depressant effect of the enzymes by themselves that may have contributed to the lack of a complete reversal of depressant effects of endo-$F_1$ and endo-$F_3$ observed in the upper panel.

FIG. 20 is a series of graphs showing that lectins with a specificity of binding similar to that described for lysozyme (i.e. *Datura stramonium* lectin and *Lycopersicon esculentum* lectin) decreased isometric tension that could be inhibited by TAC (chitotriose). On the other hand, lectins whose specificities were different from that of lysozyme (*Triticum vulgaris* lectin, *Erythrina corrallodendron* lectin, and *Helix pomatia* lectin) had a minimal effect on decreasing isometric tension.

FIG. 21 consists of 2 graphs. In the upper panel, lysozyme ($10^{-7}$M) caused no decrease in contraction as compared to time controls in guinea pig myocytes. In the lower panel, treatment of the ventricular trabeculae with protease type XIV and collagenase A eliminated the effect of lysozyme. The ventricular trabeculae were obtained from different animals within a treatment group.

Figure 22:
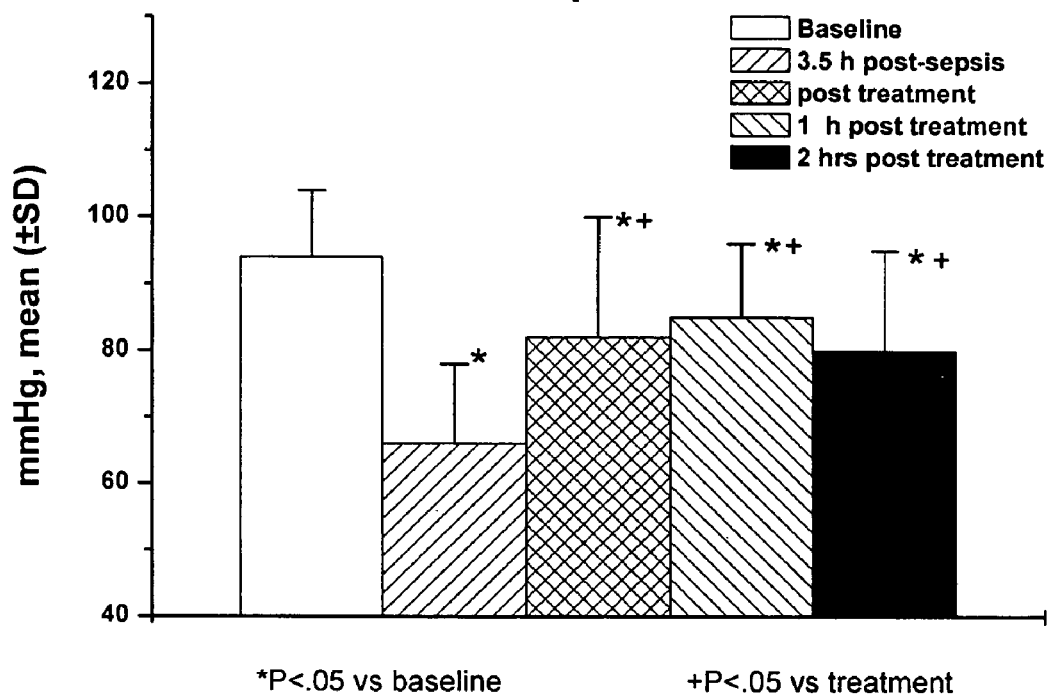

FIG. 22 is a graph showing that mean arterial pressure fell after 3.5 hrs of sepsis and increased after treatment with chitobiose.

Figure 23:
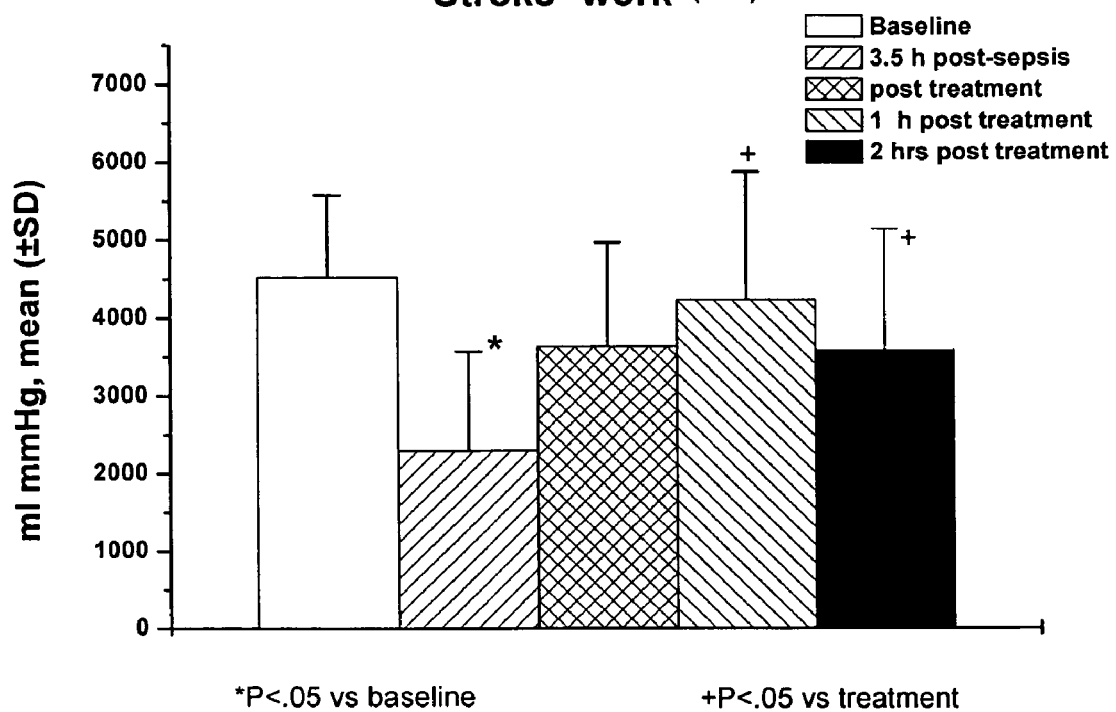

FIG. 23 is a graph showing that stroke work, the primary measurement of contractility used in this study, decreased significantly after 3.5 hrs of sepsis and increased after chitobiose treatment.

Figure 24:
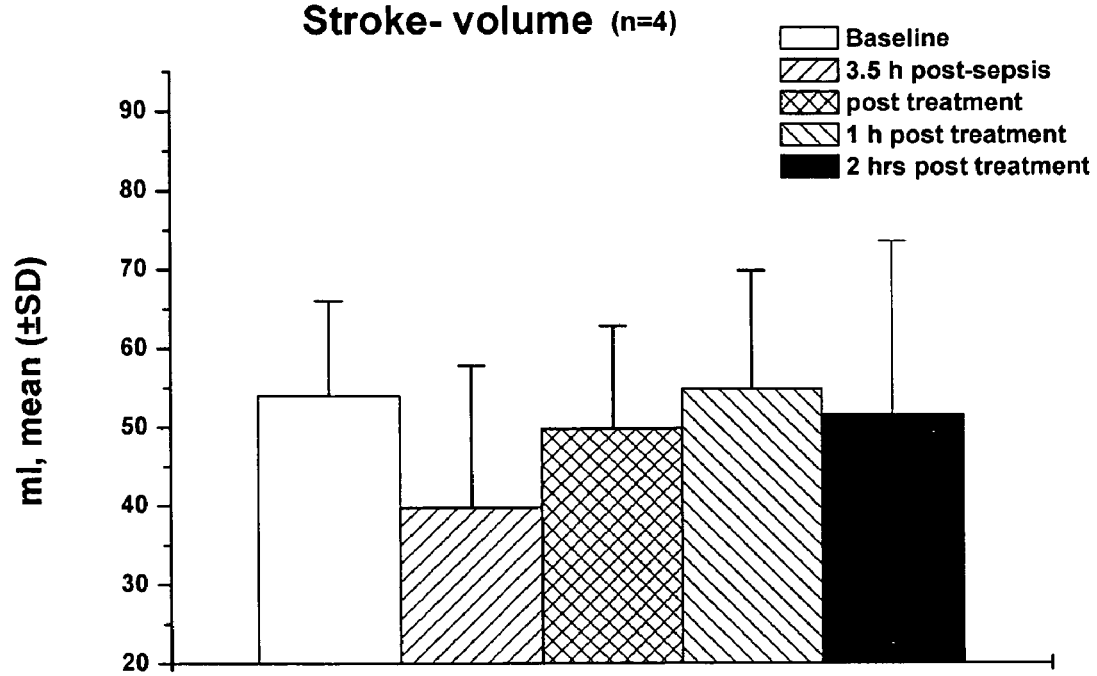

FIG. 24 is a graph showing that changes in stroke volume followed those in stroke-work, but no significant differences were observed among the conditions.

Figure 25:
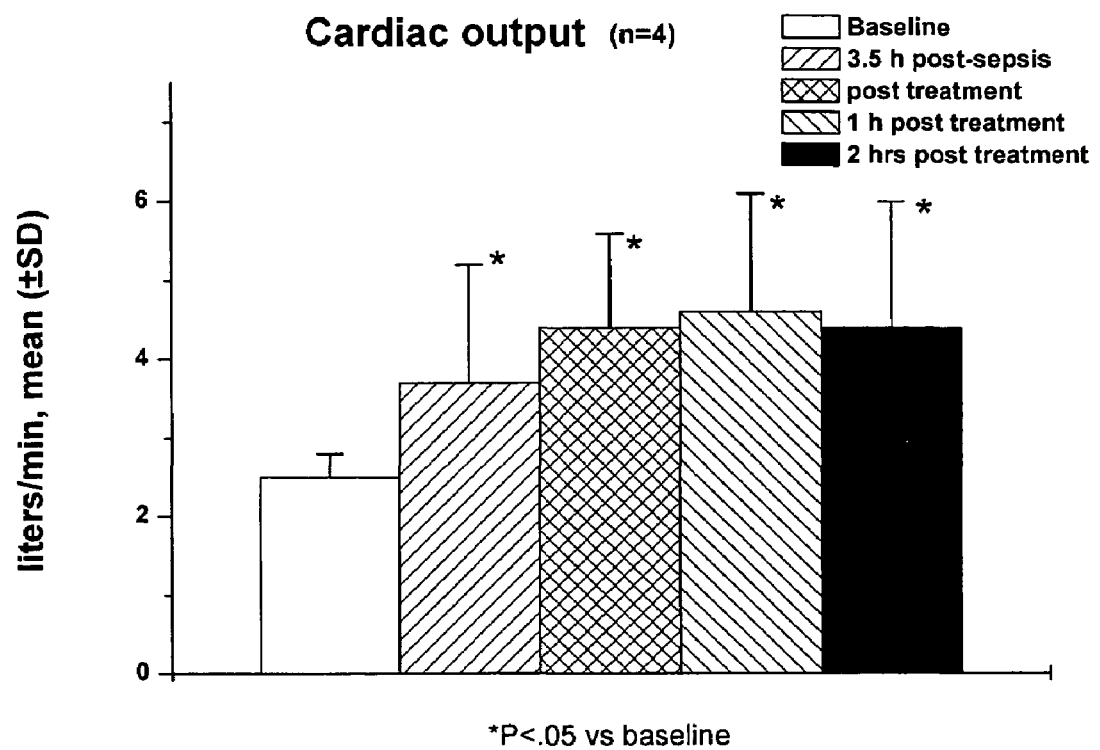

FIG. 25 is a graph showing that cardiac output increased after sepsis and remained elevated throughout the study.

Figure 26:
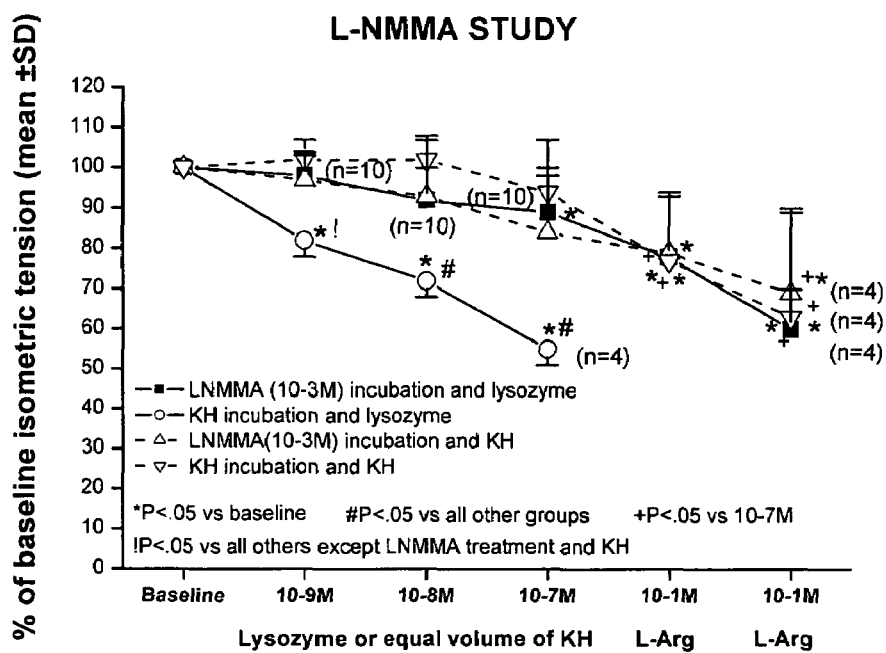

FIG. 26 is a graph showing that LNMMA significantly reduced lysozyme's myocardial depressant effect.

Figure 27:
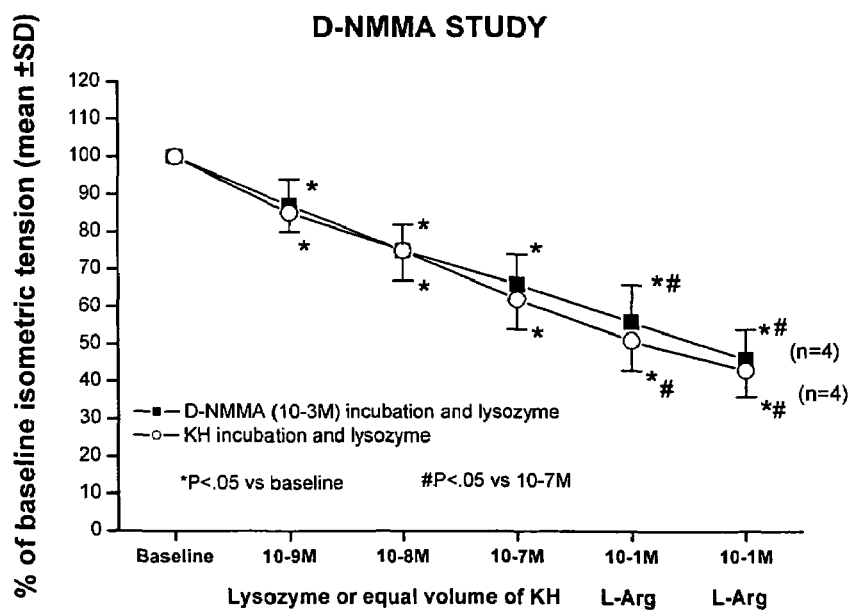

FIG. 27 is a graph showing that D-NMMA did not reduce lysozyme's myocardial depressant effect.

Figure 28:
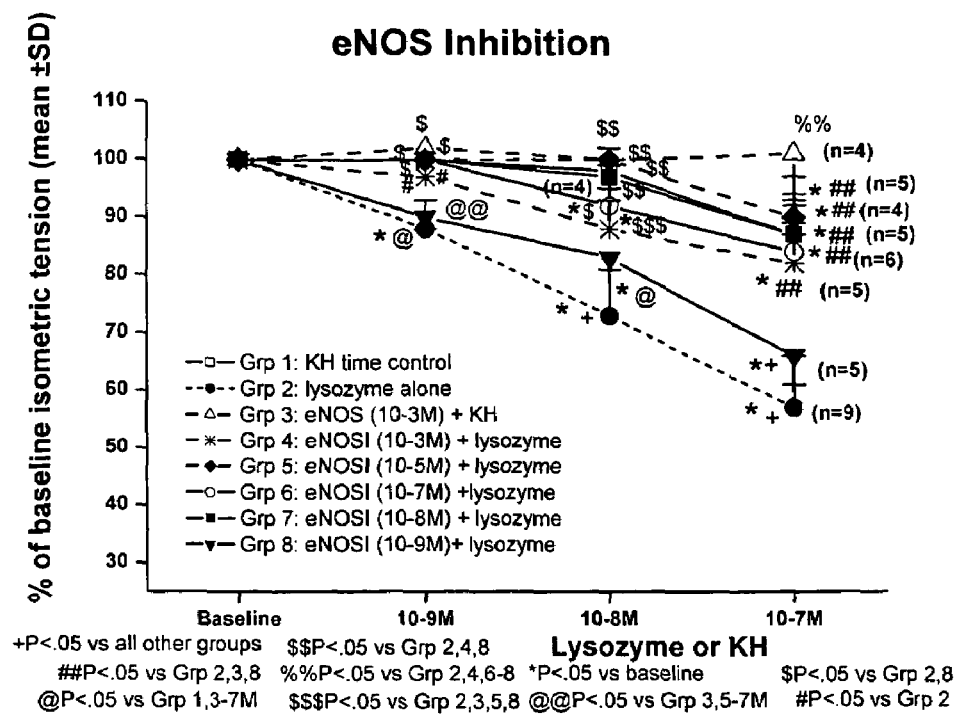

FIG. 28 is a graph showing that eNOS at a concentration of $10^{-8}$M still prevented lysozyme's myocardial depressant effect.

Figure 29:
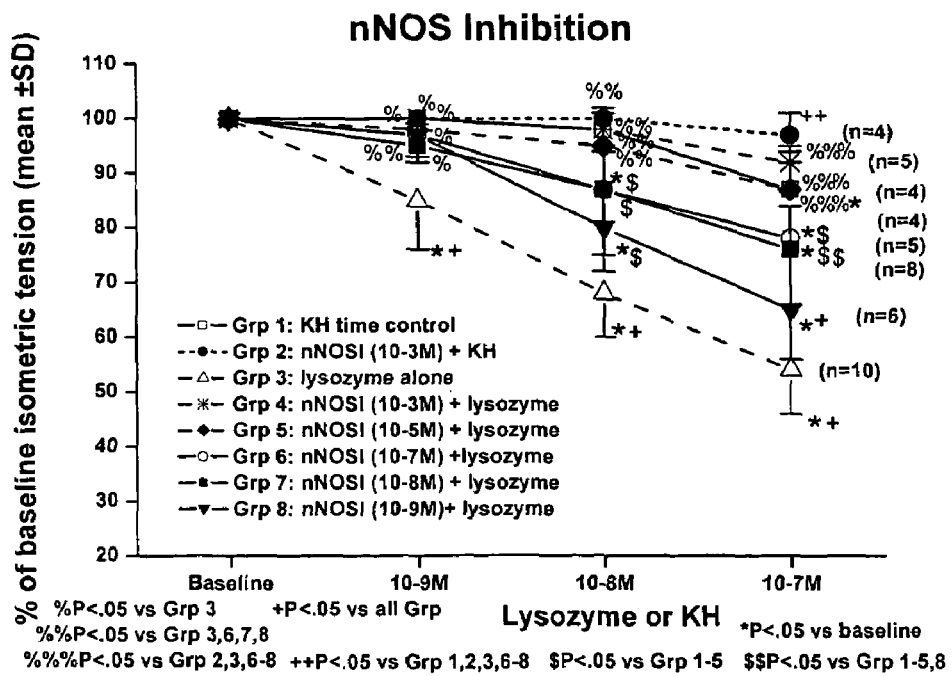

FIG. 29 is a graph showing that nNOS was effective in preventing the myocardial depression caused by lysozyme only at higher concentrations of the inhibitor ($10^{-6}$M to $10^{-7}$M) as compared to eNOS.

Figure 30:
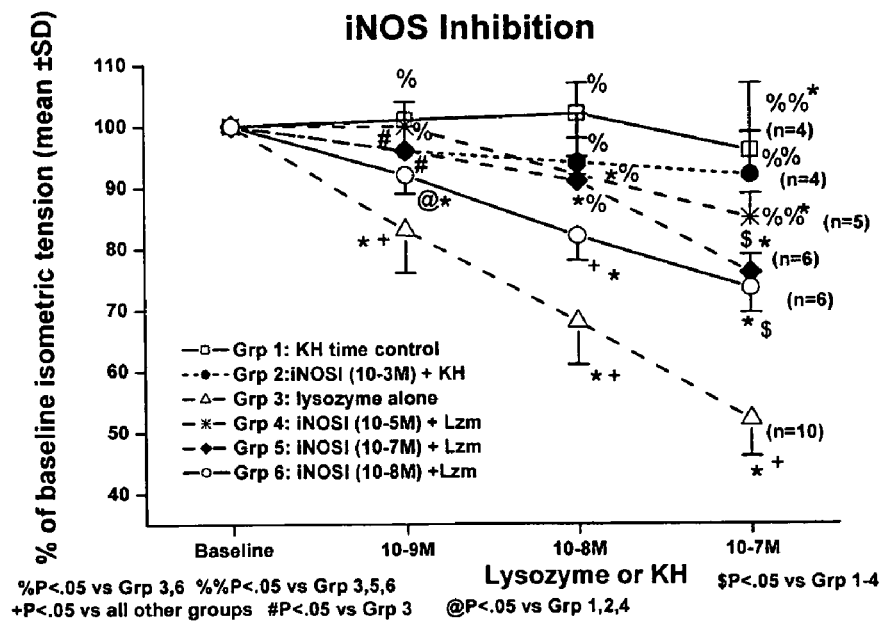

FIG. 30 is a graph showing that iNOS was effective in preventing lysozyme's depressant effect only at higher concentrations of the inhibitor ($10^{-5}$M to $10^{-7}$M) as compared to eNOS.

Figure 31:
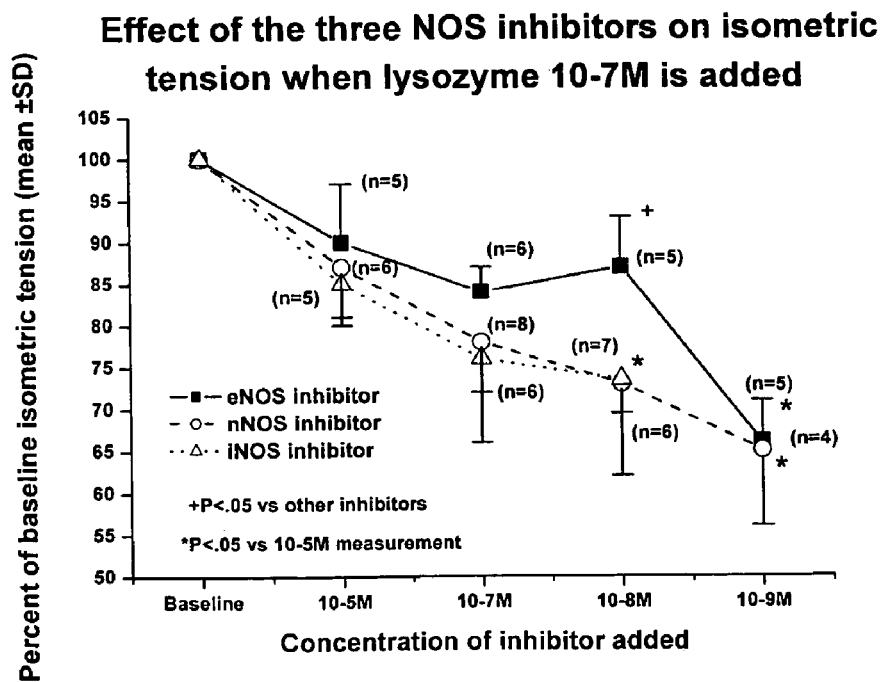

FIG. 31 is a graph providing a comparison of the individual results of three NOS inhibitors, which indicate that eNOS inhibitor was the superior one in reducing lysozyme's myocardial depressant effect as compared with nNOS and iNOS inhibitors.

Figure 32:
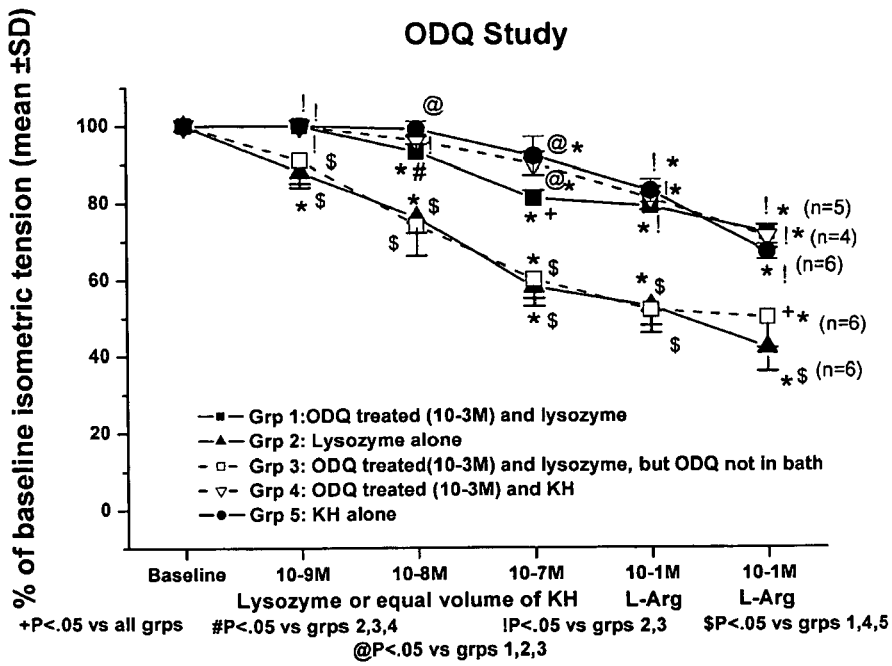

FIG. 32 is a graph showing that ODQ severely reduced the myocardial depressant effect of lysozyme.

Figure 33:
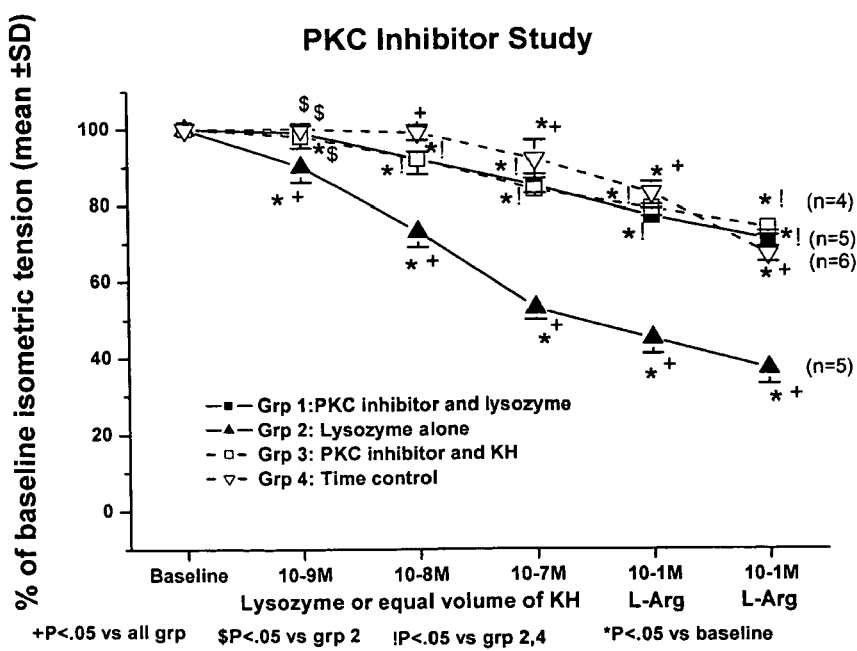

FIG. 33 is a graph showing that PKC inhibitor markedly attenuated the myocardial depressant effect of lysozyme.

Figure 34:
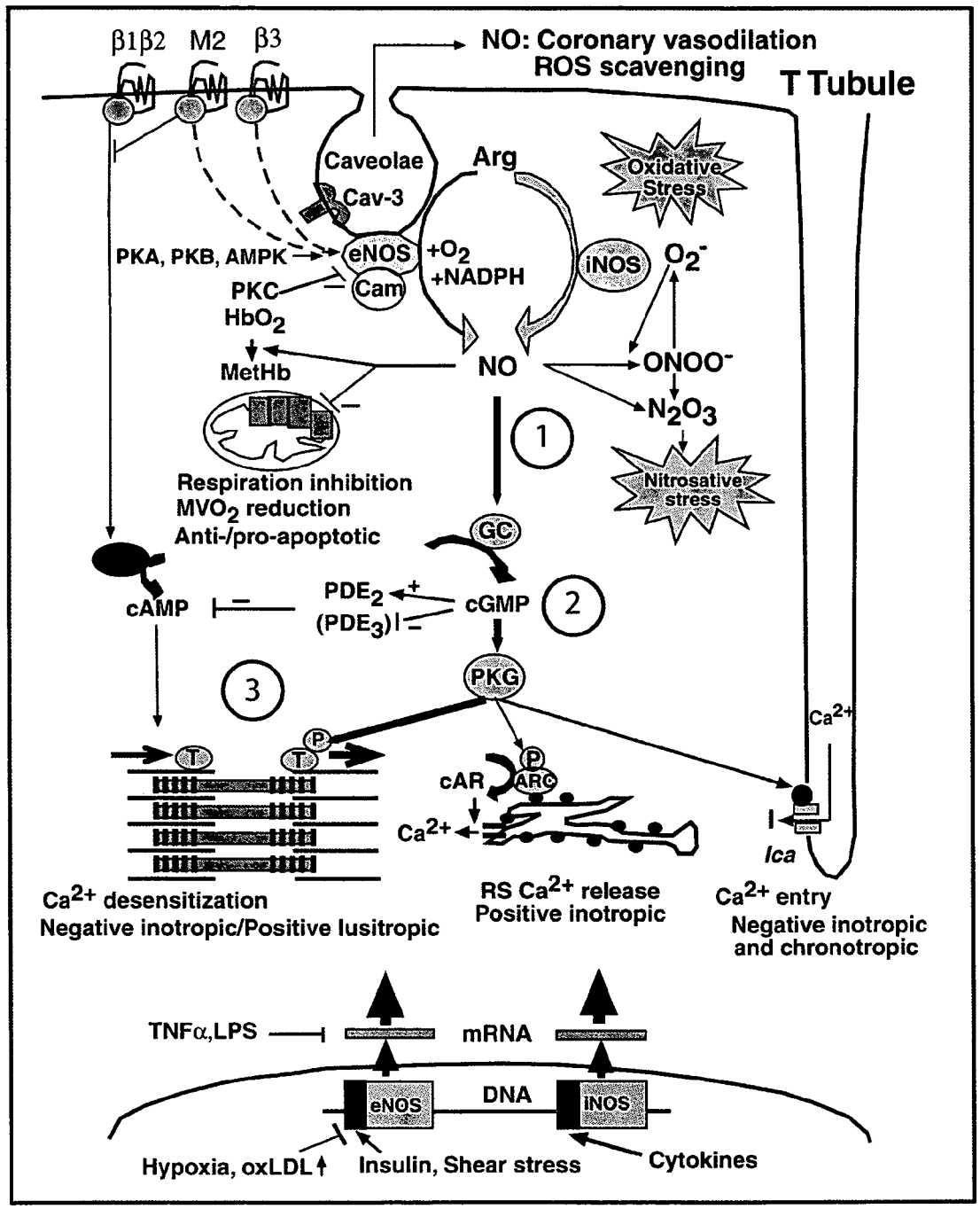

FIG. 34 is a schematic drawing that shows how nitric oxide may cause myocardial depression.

DETAILED DESCRIPTION OF THE INVENTION

I. Therapeutic Methods

The present inventors isolated and purified the filterable cardiodepressant substance (FCS) by size exclusion high pressure liquid chromatography, until a single band was identified on one dimensional gel electrophoresis. This band was then subjected to tandem mass spectrometry and protein sequencing techniques. Both physical and biochemical sequencing techniques identified FCS as lysozyme c (Lzm-S), consistent with that originating from the canine spleen. Confirmatory tests showed that purified Lzm-S produced myocardial depression in the ventricular trabecular preparation at concentrations achieved during sepsis in the in vivo preparation. Other studies performed in the in vitro preparation demonstrated that myocardial depression caused by Lzm-S was inhibited by proteinase K, a nonspecific proteolytic enzyme, as well as TAC and chitobiose, competitive inhibitors of Lzm-S activity. In addition, it was shown that Lzm-S inhibited the adrenergic responses induced by field stimulation and isoproterenol in the in vitro preparation, these results suggesting that inhibit the sympathetic response in sepsis. The present findings indicate that Lzm-S originating from disintegrating leukocytes from organs such as the spleen contributes to myocardial dysfunction in this model. The mechanism may relate to its binding or hydrolysis of a cardiac membrane glycoprotein with an extracellularly oriented carbohydrate tree thereby interfering with myocardial excitation contraction coupling in sepsis.

Accordingly, the present invention provides a method of preventing or inhibiting myocardial dysfunction comprising administering an effective amount of an agent that can inhibit lysozyme to an animal in need thereof.

The term "lysozyme" as used herein includes lysozyme c or Lzm-S which is a bacteriolytic enzyme that can catalyze the hydrolysis of N-acetyl-D-glucosamine (NAG) to N-acetylmuramic acid (NAM) linkages of bacterial cell walls.

The term "agent that can inhibit lysozyme" means any molecule or compound that can inhibit the expression of the lysozyme gene or that can inhibit the activity of lysozyme protein. Examples of agents that can inhibit lysozyme are provided in Section II. Preferred agents that can inhibit lysozyme include carbohydrates, more preferably chitobiose and TAC (chitotriose).

The terms "TAC" and "chitotriose" as used herein both refer to N,N',N" triacetylglucosamine, also commonly referred to as N,N',N" triacetylchitotriose, and are used interchangeably throughout.

The term "chitobiose" as used herein refers to N,N' diacetylglucosamine, also commonly referred to as N,N' diacetylchitobiose.

The term "effective amount" as used herein means an amount effective, at dosages and for periods of time necessary to achieve the desired result.

The term "animal" as used herein includes all members of the animal kingdom, including humans. Preferably, the animal to be treated is a human.

The term "treatment or treating" as used herein means an approach for obtaining beneficial or desired results, including clinical results. Beneficial or desired clinical results can include, but are not limited to, alleviation or amelioration of one or more symptoms or conditions, diminishment of extent of disease, stabilized (i.e. not worsening) state of disease, preventing spread of disease, delay or slowing of disease progression, amelioration or palliation of the disease state, and remission (whether partial or total), whether detectable or undetectable. "Treating" can also mean prolonging survival as compared to expected survival if not receiving treatment.

The results in Example 2 demonstrate that when TAC is given either before sepsis or in early sepsis there is a significant prevention of myocardial depression as compared to the non treated animals. Consequently, lysozyme inhibitors may be useful in preventing the onset of myocardial dysfunction in an animal with sepsis.

Accordingly, the present invention provides a method of preventing or reducing the onset of myocardial dysfunction in an animal with sepsis comprising administering an effective amount of an agent that can inhibit lysozyme to the animal.

The inventors have demonstrated that lysozyme contributes to myocardial dysfunction in an animal model of septic shock. Sepsis is the result of an overwhelming inflammatory response to a severe infection. Therefore, agents that can inhibit lysozyme may also be useful in treating inflammation.

Accordingly, the present invention provides a method of preventing or treating an inflammatory condition comprising administering an effective amount of an agent that can inhibit lysozyme to an animal in need thereof.

The inflammatory condition that can be treated using the method of the invention includes, but is not limited to, bacterial infection (such as sepsis) or one of a group of diseases called systematic inflammatory response syndrome (SIRS). SIRS is a wide-spread inflammatory response to a variety of severe clinical insults that include pancreatitis.

The results in Example 5 demonstrate that when chitobiose was administered after myocardial depression had already developed in an animal with sepsis there was a reversal of the myocardial depression observed. Consequently, lysozyme inhibitors may be useful in reversing myocardial depression in an animal with sepsis.

Accordingly, the present invention provides a method of reversing myocardial depression in an animal with sepsis comprising administering an effective amount of an agent that can inhibit lysozyme to the animal. Preferably the agent is chitobiose.

II. Agents That Inhibit Lysozyme

The finding by the present inventors that lysozyme plays a role in cardiac dysfunction and inflammation allows the discovery and development of agents that inhibit lysozyme for use in modulating these conditions.

The present invention includes the use of any and all agents that modulate lysozyme in the methods of the invention. The agent can be any type of substance, including, but not limited to, nucleic acids (including antisense oligonucleotides), proteins (including antibodies), peptides, peptide mimetics, carbohydrates, small molecules (including organic and inorganic compounds) and lectin inhibitors. Examples of some of the agents that modulate lysozyme are provided below.

(i) Carbohydrates

In one embodiment, the agent that can inhibit lysozyme is a carbohydrate. In a specific embodiment, the agent that inhibits lysozyme is a carbohydrate having at least two N-acetyl glucosamine (NAG) units, preferably 2 or 3 NAG units. In a specific embodiment, the lysozyme inhibitor is chitobiose (N,N' diacetylglucosamine) or TAC (N,N',N" triacetylglucosamine also referred to as chitotriose).

The natural substrate of lysozyme is the hexasaccharide NAG-NAM-NAG-NAM-NAG-NAM (corresponding to monosaccharides in an arrangement A-B-C-D-E-F). The enzyme lysozyme can hydrolyse only between positions D and E yielding as natural reaction products NAG-NAM-NAG-NAM and NAG-NAM. Both the tetrasaccharide NAG-NAM-NAG-NAM and the disaccharide NAG-NAM will act as product inhibitors of the enzyme. After the natural hexasaccharide is bound to lysozyme, the monosaccharide ring D is subjected to distortion by the enzyme: Ring D is forced from the chair conformation into the half-chair conformation before hydrolysis of the beta 1-4 glycosidic bond between rings D and E occurs. The hexasaccharide with a distorted ring D is referred to as the transition state or highly reactive state of the substrate. A transition state inhibitor of lysozyme is NAG-NAG-NAG-NAG*, where NAG* is the lactone analog of NAG. NAG* has a conformation closely resembling the half-chair conformation of ring D of the natural substrate in the transition state. A transition state inhibitor of the composition NAG-NAM-NAG-NAM*, where NAM* is a lactone analog of NAM, should be still more effective. Transition state inhibitors, where available, are most powerful inhibitors of lysozyme.

The carbohydrates used in the methods of the invention can be prepared as neoglycoconjugates in order to prolong their serum half-life. For example, TAC or chitobiose can be chemically coupled to a large molecule such as human serum albumin (HSA) or bovine serum albumin (BSA). Neoglycoconjugates can be prepared using techniques known in the art. (See for example Glycoprotein synthesis: From glycobiological tools to tailor-made catalysts, by B G Davis and J B Jones, Synleft 1990; 9:1495-1507.)

(ii) Binding Inhibitors

In another embodiment, the agent that can inhibit lysozyme is an agent that inhibits the binding of lysozyme to its cellular target.

The inventors show in Example 2 that lysozyme interacts with a glycoprotein on the cardiac membrane. Removal of the carbohydrate portion of the cardiac membrane reduces the effect of lysozyme on myocardial dysfunction. Further proof that binding of lysozyme to glycoproteins is required for its function is provided in Example 3 in which lectins were used to mimic lysozyme's depressant effect on the myocardium and in Example 4, in which the binding sites of lysozyme to membrane glycoprotein were further characterized. Accordingly, the lysozyme inhibitor can be any agent that can interfere with the binding of lysozyme to a glycoprotein on the surface of the cell to be treated such as a cardiac cell. Techniques known in the art can be used to determine if an agent interferes with the binding of lysozyme to a carbohydrate. The inventors previously used one of the principles of elucidating the binding of lysozyme to carbohydrate in Example 2 (FIG. 12) in which enzymatic deglycosylation was used. The inventors used endoglycosidase action to remove larger blocks of carbohydrate and showed that the depressant effect of lysozyme was much attenuated as compared with the native preparation. It is also possible to use exoglycosidases, where individual sugars are removed from the outside positions of the carbohydrate tree and to test for the effect of lysozyme in the in vitro preparation.

One could also determine that lysozyme binds to the cardiac surface membrane by means of immunohistochemistry techniques. In the in vitro preparation, one would instill lysozyme into the in vitro preparation that would bind to the cardiac surface membrane. One would then add a fluorescent labeled antibody that would in turn bind to the lysozyme already located on the membrane. The ventricular trabecular muscle would be removed from the bath and quickly frozen and standard techniques used for pathological examination. Under a confocal microscope or other imaging techniques, one could detect the fluorescent labeled antibody located adjacent to the cardiac surface membrane.

Finally, one could use nuclear magnetic resonance (NMR) techniques. Both the free lysozyme and the free carbohydrate have typical nuclear magnetic resonance spectra. On interaction of the two, there will be a characteristic change of the NMR spectrum.

(ii) Antibodies

In another embodiment, the agent that can inhibit lysozyme is a lysozyme specific antibody. Antibodies to lysozyme may be prepared using techniques known in the art such as those described by Kohler and Milstein, Nature 256, 495 (1975) and in U.S. Pat. Nos. RE 32,011; 4,902,614; 4,543,439; and 4,411,993, which are incorporated herein by reference. (See also Monoclonal Antibodies, Hybridomas: A New Dimension in Biological Analyses, Plenum Press, Kennett, McKearn, and Bechtol (eds.), 1980, and Antibodies: A Laboratory Manual, Harlow and Lane (eds.), Cold Spring Harbor Laboratory Press, 1988, which are also incorporated herein by reference). Within the context of the present invention, antibodies are understood to include monoclonal antibodies, polyclonal antibodies, antibody fragments (e.g., Fab, and $F(ab')_2$) and recombinantly produced binding partners.

(iv) Antisense Oligonucleotides

In another embodiment, the agent that can inhibit lysozyme is an antisense oligonucleotide that inhibits the expression of the lysozyme gene. The term "antisense oligonucleotide" as used herein means a nucleotide sequence that is complementary to its target, e.g. the lysozyme gene. The sequence of the lysozyme gene is known in the art, for example, go to www.tigr.org/docs/tigr-scripts/tgi/geneprod search.pl. 5 different lysozyme genes are deposited.

The term "oligonucleotide" as used herein refers to an oligomer or polymer of nucleotide or nucleoside monomers consisting of naturally occurring bases, sugars, and intersugar (backbone) linkages. The term also includes modified or substituted oligomers comprising non-naturally occurring monomers or portions thereof, which function similarly. Such modified or substituted oligonucleotides may be preferred over naturally occurring forms because of properties such as enhanced cellular uptake, or increased stability in the presence of nucleases. The term also includes chimeric oligonucleotides that contain two or more chemically distinct regions. For example, chimeric oligonucleotides may contain at least one region of modified nucleotides that confer beneficial properties (e.g. increased nuclease resistance, increased uptake into cells), or two or more oligonucleotides of the invention may be joined to form a chimeric oligonucleotide.

The antisense oligonucleotides of the present invention may be ribonucleic or deoxyribonucleic acids and may contain naturally occurring bases including adenine, guanine, cytosine, thymidine and uracil. The oligonucleotides may also contain modified bases such as xanthine, hypoxanthine, 2-aminoadenine, 6-methyl, 2-propyl and other alkyl adenines, 5-halo uracil, 5-halo cytosine, 6-aza uracil, 6-aza cytosine and 6-aza thymine, pseudo uracil, 4-thiouracil, 8-halo adenine, 8-aminoadenine, 8-thiol adenine, 8-thiolalkyl adenines, 8-hydroxyl adenine and other 8-substituted adenines, 8-halo guanines, 8-amino guanine, 8-thiol guanine, 8-thiolalkyl guanines, 8-hydroxyl guanine and other 8-substituted guanines, other aza and deaza uracils, thymidines, cytosines, adenines, or guanines, 5-trifluoromethyl uracil and 5-trifluoro cytosine.

Other antisense oligonucleotides of the invention may contain modified phosphorous, oxygen heteroatoms in the phosphate backbone, short chain alkyl or cycloalkyl intersugar linkages or short chain heteroatomic or heterocyclic intersugar linkages. For example, the antisense oligonucleotides may contain phosphorothioates, phosphotriesters, methyl phosphonates, and phosphorodithioates. In an embodiment of the invention there are phosphorothioate bond links between the four to six 3'-terminus bases. In another embodiment phosphorothioate bonds link all the nucleotides.

The antisense oligonucleotides of the invention may also comprise nucleotide analogs that may be better suited as therapeutic or experimental reagents. An example of an oligonucleotide analogue is a peptide nucleic acid (PNA) wherein the deoxyribose (or ribose) phosphate backbone in the DNA (or RNA), is replaced with a polyamide backbone which is similar to that found in peptides (P. E. Nielsen, et al Science 1991, 254, 1497). PNA analogues have been shown to be resistant to degradation by enzymes and to have extended lives in vivo and in vitro. PNAs also bind stronger to a complementary DNA sequence due to the lack of charge repulsion between the PNA strand and the DNA strand. Other oligonucleotides may contain nucleotides containing polymer backbones, cyclic backbones, or acyclic backbones. For example, the nucleotides may have morpholino backbone structures (U.S. Pat. No. 5,034,506). Oligonucleotides may also contain groups such as reporter groups, a group for improving the pharmacokinetic properties of an oligonucleotide, or a group for improving the pharmacodynamic properties of an antisense oligonucleotide. Antisense oligonucleotides may also have sugar mimetics.

The antisense nucleic acid molecules may be constructed using chemical synthesis and enzymatic ligation reactions using procedures known in the art. The antisense nucleic acid molecules of the invention or a fragment thereof, may be chemically synthesized using naturally occurring nucleotides or variously modified nucleotides designed to increase the biological stability of the molecules or to increase the physical stability of the duplex formed with mRNA or the native gene (e.g. phosphorothioate derivatives and acridine substituted nucleotides). The antisense sequences may be produced biologically using an expression vector introduced into cells in the form of a recombinant plasmid, phagemid or attenuated virus in which antisense sequences are produced under the control of a high efficiency regulatory region, the activity of which may be determined by the cell type into which the vector is introduced.

(v) Peptide Mimetics

The present invention also includes peptide mimetics of the lysozyme protein. Such peptides may include competitive inhibitors, peptide mimetics, and the like. All of these peptides as well as molecules substantially homologous, complementary or otherwise functionally or structurally equivalent to these peptides may be used for purposes of the present invention.

"Peptide mimetics" are structures which serve as substitutes for peptides in interactions between molecules (See Morgan et al (1989), Ann. Reports Med. Chem. 24:243-252 for a review). Peptide mimetics include synthetic structures which may or may not contain amino acids and/or peptide bonds but retain the structural and functional features of a lysozyme peptide, or enhancer or inhibitor of the lysozyme peptide. Peptide mimetics also include molecules incorporating peptides into larger molecules with other functional elements (e.g., as described in WO 99/25044). Peptide mimetics also include peptoids, oligopeptoids (Simon et al (1972) Proc. Natl. Acad. Sci. USA 89:9367), and peptide libraries containing peptides of a designed length representing all possible sequences of amino acids corresponding to a peptide of the invention.

Peptide mimetics may be designed based on information obtained by systematic replacement of L-amino acids by D-amino acids, replacement of side chains with groups having different electronic properties, and by systematic replacement of peptide bonds with amide bond replacements. Local conformational constraints can also be introduced to determine conformational requirements for activity of a candidate peptide mimetic. The mimetics may include isosteric amide bonds, or D-amino acids to stabilize or promote reverse turn conformations and to help stabilize the molecule. Cyclic amino acid analogues may be used to constrain amino acid residues to particular conformational states. The mimetics can also include mimics of inhibitor peptide secondary structures. These structures can model the 3-dimensional orientation of amino acid residues into the known secondary conformations of proteins. Peptoids may also be used which are oligomers of N-substituted amino acids and can be used as motifs for the generation of chemically diverse libraries of novel molecules.

(vi) Other Substances

In addition to the above substances, other substances that can modulate lysozyme can also be identified and used in the methods of the invention. For example, substances which can bind lysozyme may be identified by reacting lysozyme with a substance which potentially binds to lysozyme, then detecting if complexes between the lysozyme and the substance have formed. Substances that bind lysozyme in this assay can be further assessed to determine if they are useful in modulating or inhibiting lysozyme and useful in the therapeutic methods of the invention.

Accordingly, the present invention also includes a method of identifying substances which can bind to lysozyme comprising the steps of:

(a) reacting lysozyme and a test substance, under conditions which allow for formation of a complex between the lysozyme and the test substance, and (b) assaying for complexes of lysozyme and the test substance, for free substance or for non complexed lysozyme, wherein the presence of complexes indicates that the test substance is capable of binding lysozyme.

Conditions which permit the formation of substance and lysozyme complexes may be selected having regard to factors such as the nature and amounts of the substance and the protein.

The substance-lysozyme complex, free substance or non-complexed proteins may be isolated by conventional isolation techniques, for example, salting out, chromatography, electrophoresis, gel filtration, fractionation, absorption, polyacrylamide gel electrophoresis, agglutination, or combinations thereof. To facilitate the assay of the components, antibody against lysozyme or the substance, or labelled lysozyme, or a labelled substance may be utilized. The antibodies, lysozyme, or substances may be labelled with a detectable substance.

The lysozyme or the test substance used in the method of the invention may be insolubilized. For example, the lysozyme or substance may be bound to a suitable carrier. Examples of suitable carriers are agarose, cellulose, dextran, Sephadex, Sepharose, carboxymethyl cellulose, polystyrene, filter paper, ion-exchange resin, plastic film, plastic tube, glass beads, silica, polyamine-methyl vinyl-ether-maleic acid copolymer, amino acid copolymer, ethylene-maleic acid copolymer, nylon, silk, etc. The carrier may be in the shape of, for example, a tube, test plate, beads, disc, sphere etc.

The insolubilized lysozyme or substance may be prepared by reacting the material with a suitable insoluble carrier using known chemical or physical methods, for example, cyanogen bromide coupling.

The lysozyme or test substance may also be expressed on the surface of a cell in the above assay.

The lysozyme gene or protein may be used as a target for identifying lead compounds for drug development. The invention therefore includes an assay system for determining the effect of a test compound or candidate drug on the activity of the lysozyme gene or protein.

Accordingly, the present invention provides a method for identifying a compound that modulates lysozyme gene or protein activity comprising:

(a) incubating a test compound with a lysozyme protein or a nucleic acid encoding a lysozyme protein; and (b) determining the effect of the test compound on lysozyme protein activity or lysozyme gene expression and comparing with a control (i.e. in the absence of a test compound) wherein a change in the lysozyme protein activity or lysozyme gene expression as compared to the control indicates that the test compound is a potential modulator of the lysozyme gene or protein.

III. Compositions

The present invention also includes pharmaceutical compositions containing the agents that can inhibit lysozyme for use in the methods of the invention. Accordingly, the present invention provides a pharmaceutical composition for inhibiting inflammation comprising an effective amount of an agent that can inhibit lysozyme in admixture with a suitable diluent or carrier. The present invention further provides a pharmaceutical composition for preventing or inhibiting cardiac dysfunction comprising an effective amount of an agent that can inhibit lysozyme in admixture with a suitable diluent or carrier. The present invention also provides a pharmaceutical composition for treating sepsis comprising an effective amount of an agent that can inhibit lysozyme in admixture with a suitable diluent or carrier.

Such pharmaceutical compositions can be for intralesional, intravenous, topical, rectal, parenteral, local, inhalant or subcutaneous, intradermal, intramuscular, intrathecal, transperitoneal, oral, and intracerebral use. The composition can be in liquid, solid or semisolid form, for example pills, tablets, creams, gelatin capsules, capsules, suppositories, soft gelatin capsules, gels, membranes, tubelets, solutions or suspensions.

The pharmaceutical compositions of the invention can be intended for administration to humans or animals. Dosages to be administered depend on individual needs, on the desired effect and on the chosen route of administration.

The pharmaceutical compositions can be prepared by per se known methods for the preparation of pharmaceutically acceptable compositions which can be administered to patients, and such that an effective quantity of the active substance is combined in a mixture with a pharmaceutically acceptable vehicle. Suitable vehicles are described, for example, in Remington's Pharmaceutical Sciences (Remington's Pharmaceutical Sciences, Mack Publishing Company, Easton, Pa., USA 1985).

On this basis, the pharmaceutical compositions include, albeit not exclusively, the active compound or substance in association with one or more pharmaceutically acceptable vehicles or diluents, and contained in buffered solutions with a suitable pH and iso-osmotic with the physiological fluids. The pharmaceutical compositions may additionally contain other agents such as other agents that can prevent the inhibition of apoptosis or that are used in treating inflammatory conditions or sepsis.

The following non-limiting examples are illustrative of the present invention. While not wishing to be bound by any particular theory or mechanism of the invention, the inventors have proposed certain theories and mechanisms for the invention in the disclosed examples. It is to be understood that the invention is not intended to be limited to any particular theory or mechanism discussed herein.

EXAMPLES

Example 1

Lysozyme: a Mediator of Myocardial Depression and Adrenergic Dysfunction in Septic Shock The objective of the present study was to identify the nature of a filterable cardiodepressant factor (FCS) that contributes to myocardial dysfunction in a canine model of *Escherichia coli* septic shock. In a previous study, it was found that FCS increased in plasma after 4 h of bacteremia (Am J Physiol 1993; 264: H1402) in which FCS was identified by a bioassay that included a right ventricular trabecular preparation (RVT). In that study, FCS was only partially identified by pore filtration techniques and was found to be a protein of molecular weight between 10-30K. In the present study, FCS was further purified by size exclusion high pressure liquid chromatography, until a single band was identified on one dimensional gel electrophoresis. This band was then subjected to tandem mass spectrometry and protein sequencing techniques and both techniques identified FCS as lysozyme c (Lzm-S), consistent with that originating from the canine spleen. Confirmatory tests showed that purified Lzm-S produced myocardial depression in the RVT preparation at concentrations achieved during sepsis in the in vivo preparation. In addition, Lzm-S inhibited the adrenergic response induced by field stimulation in the in vitro preparation, these results suggesting that Lzm-S may inhibit the neural sympathetic response in sepsis. The present findings indicate that Lzm-S originating from disintegrating leukocytes from organs such as the spleen contributes to myocardial dysfunction in this model. The mechanism may relate to its binding or hydrolysis of a cardiac membrane glycoprotein thereby interfering with myocardial excitation contraction coupling in sepsis.

In the present study, the inventors further purified FCS to the extent that a single broad band could be found on one-dimensional-gel electrophoresis. The inventors then determined the nature of this substance by microcapillary reverse phase high pressure liquid chromatography (HPLC) tandem mass spectrometry (MS/MS) and protein sequencing techniques (8,9). Once this substance was isolated, the inventors showed that it decreased myocardial contraction and adrenergic responses to neural stimulation and the β-agonist isoproterenol in respective right ventricular trabecular preparations. The inventors also showed that these effects could be blocked by a competitive inhibitor of FCS, the results providing further evidence that this substance may be important in the pathophysiology of myocardial dysfunction in sepsis.

Methods

These experiments were approved by the University Animal Care Committee and conform with the Guide for the Care and Use of Laboratory Animals published by the US National Institutes of Health (NIH Publication No 85-23,1996) (10).

The model of *E. coli* sepsis used in this study has previously been described (6). In brief, the dogs (20 to 30 kg) were anesthetized with pentobarbital sodium (30 mg/kg); the trachea was intubated with an endotracheal tube; and the lungs were mechanically ventilated. The animal was given 3 ml of heparin (1000 units/ml) intravenously. After 1 hr of stability, sepsis was induced by intravenous infusion of $10^{10}$ colony-forming units (CFU) of live *E. coli* (0111:B4) that were suspended in normal saline and were administered over 1 h. Approximately $5 \times 10^9$ CFU/h of *E. coli* were then infused for 3 additional hours, at which time left ventricular contractility and mean arterial pressure have been shown to be depressed to approximately 60-75% of baseline in this model (6).

Isolation of FCS

In a previous study, FCS activity was identified in the 10-30 KD plasma fraction by pore filtration techniques (7) and this fraction served as a starting point for further purification. In the dogs described above, sixty milliliters of blood were taken from the femoral artery before and after 4 h of sepsis, and the samples centrifuged. Because of the large size of the animals, this phlebotomy did not affect their hemodynamic status. The plasma samples were sequentially passed through filters with cut-offs of 30,000 and 10,000 molecular weight (Millipore, Bedford, Mass.), respectively, to isolate the 10-30 KD plasma fraction. Approximately three ml of this fraction could be obtained from each of the presepsis and sepsis samples.

Aliquots of the 10-30 KD plasma fraction (0.05 to 1 ml) were then added to a right ventricular (RV) trabecular preparation to test for the presence of FCS activity. The RV preparation has previously been described (6,7). Briefly, mongrel dogs (3 to 10 kg) were anesthetized with pentobarbital, and their hearts were removed. Three to four thin trabeculae (<1 mm diameter) were obtained from the right ventricle and were suspended in a vertical constant temperature bath (5 ml) that contained Krebs Henseleit (KH) solution. The muscle was stimulated electrically at 0.5 Hz. Aliquots of plasma fractions (from 0.05 to 1 ml) were added to respective organ baths at 5 minute intervals. The changes observed in the pre and septic plasma fractions were expressed relative to tensions found at baseline (i.e. prior to the addition of the sample). An increase in the depressant activity in the septic plasma fraction relative to that found in the presepsis sample was indicative of an increase in FCS.

Since pore filtration techniques are an imperfect method of purification, size-exclusion high pressure liquid chromatography (SEC-HPLC) was additionally used in the present study to further purify the 10-30 KD plasma fraction. In this procedure, 50 µl protein markers (Boehringer Mannheim Biochemica) were first run through a column (Progel-TSK G2000SWXL) in 0.1 M phosphate buffer, pH 6.7, flow rate at 1.0 ml/min to derive the standard curve. The standard markers used were 465 KD (5.58 min), 150 KD (8.75 min), 50 KD (10.98 min), 17 KD (11.98 min), 38D (14.45 min). Then the 10-30 KD plasma fraction (100 µl) was injected into the column. The eluent obtained from the column was divided into three fractions termed F1, F2, and F3 in which the molecular weight of the substances contained in the F1 fraction was >30 KD, in the F2 fraction was between 10-30 KD, and in the F3 fraction was <10 KD. F1, F2, and F3 fractions were then tested by the right ventricular muscle bioassay to confirm that FCS activity was contained in the 10-30 KD plasma fraction.

In addition, the respective F1, F2, and F3 pre and sepsis fractions from all of the dogs were pooled, and aliquots of the samples were then run on a single dimension polyacrylamide gel electrophoresis (SDS-PAGE, 12.5%) and stained with silver nitrate. The volume and protein concentration of the samples were 20 µl and 56 µg, respectively. There were no differences in the bands found in the F1 and F3 fractions on SDS-PAGE between presepsis and sepsis samples (see Result Section). On the other hand, in the F2 fraction, a broad band was found in the sepsis sample located at approximately 15 KD that could not be observed in the presepsis sample. This band, as well as a comparable area in the presepsis sample was cut from the gel and sent to the Harvard Microchemistry Facility (Cambridge, Mass.) for sequence analysis.

This analysis included microcapillary reverse phase HPLC tandem mass spectrometry (µLC/MS/MS) on a Finnigan LCQ quadrupole ion trap instrument (8,9). In this procedure, a reverse-phase HPLC run is directly coupled to the nano-electrospray ionization source of an ion trap mass spectrometer. This configuration is capable of acquiring individual sequence (MS/MS) spectra on-line at high sensitivity (<<<10 femtomole) for multiple peptides in the chromatographic run. These fragmentation spectra are then correlated with known sequences in which the algorithm Sequest developed at the University of Washington and the programs developed at the Harvard Microchemistry Facility were used. In addition, a HPLC chromatogram of the enzymatically digested sample was obtained from the pre and sepsis samples. Two chromatogram peaks in the sepsis sample that were not found in the presepsis sample were subsequently subjected to chemical sequencing analysis (11, 12).

Since results of the sequencing suggested that the FCS was produced in the spleen, FCS activity was measured in the spleen, the proposed source of FCS, as well as the heart, the proposed target organ of FCS. In addition, FCS activity was measured in lymphocytes, a cell type that would not be associated with production of this protein and would therefore serve as a negative control. Neutrophils, another source of FCS were not measured, since these cells would be found in the spleen. In these experiments, spleens and hearts were removed from dogs subjected to 4 hrs of E. coli sepsis (septic group), and the results were compared to organs of animals subjected to 4 hrs of infusion of normal saline (nonseptic group). 10 gram aliquots of the spleens and hearts were obtained and were placed in 50 ml KH buffer. The mixture was homogenized and centrifuged at 1500 g for 10 minutes. The supernatant was passed through respective 30 and 10 KD filters to isolate the 10-30 KD fraction. Aliquots of the 10-30 KD sample were then placed into the organ bath, and the reduction in isometric tension relative to baseline was compared between the septic and nonseptic preparations. In addition, lymphocytes were isolated from plasma samples of dogs by cell separation media placed in buffer solution (Organon Teknika Corporation, Durham N.C.), and the cells were analyzed for FCS activity in the pre and septic samples. A modification of the method of Boyum was used (13) in which centrifugation through a Ficoll sodium diatrizoate solution causes differential migration that results in the formation of several cell layers. In the lymphocyte layer, the procedure produces $5 \times 10^6$ cells/ml that was composed of lymphocytes after staining and by light microscopy analysis.

Purification of Canine Spleen Lysozyme and Assay of Activity

Since tandem mass-spectrometry showed that cardiac depressant activity was due to spleen lysozyme (Lzm-S) (see Results), Lzm-S was purified in a manner described by Grobler et al (14). In the present study, note that the term Lzm-S is used rather than lysozyme c, since from the standpoint of the present results, the lysozyme identified by sequencing could arise from the source organ, ie the spleen or leukocytes arising from that organ, or possibly from other organs (see Discussion). In the preparatory process used, the spleen was homogenized in a blender in 2 vol of water and the homogenate was centrifuged at 7000 rpm for 15 minutes at 4° C. The pellet was reextracted with water and centrifuged again. The supernatants were pooled and the pH was adjusted to 4.5 with 10% acetic acid. The solution was heated to boiling for a short period (3 minutes) and then centrifuged as before. The pH of the supernatant was adjusted to 7.0 with 2 M Tris, and the fraction that precipitated between 30 to 80% saturation with ammonium sulfate was collected by centrifugation. The pellet was dissolved in 0.1 M Tris-HCl, pH 7.4 and dialyzed against the same buffer. Lzm-S was subsequently purified by cation-exchange chromatography (CEC) with CM-cellulose (Whatman CM-52, Kent United Kingdom). The columns were equilibrated with a linear gradient (200 to 600 ml) from 0 to 0.4 M NaCl in 0.1 M Tris pH 7.4. The protein was further purified by SEC-HPLC. Purification was confirmed by means of SDS gel and two-dimensional electrophoresis.

In addition, the amount of Lzm-S activity found in the preseptic and septic plasma fractions was estimated by the turbidometric method of Shugar (15). Aliquots of suspension of 25 mg heat killed *Micrococcus lysodeikticus* in 100 ml of phosphate buffer, pH 6.4 with 0.1% NaCl and 0.3 ml of standard or presepsis and sepsis plasma fraction samples were used. Lzm-S activity was measured in a spectrophotometer as change in percent transmission at 450 nm for an interval of 1 minute following the addition of the sample to the bacterial suspension.

Effect of Lzm-S on Myocardial Isometric Tension

The effect of purified Lzm-S on myocardial depression was then studied in the ventricular trabecular preparation. In initial experiments, the objective was to compare Lzm-S prepared from septic and nonseptic spleens to see if there was any difference between the two preparations. Although no differences were apparent by SDS-PAGE gel, different isoforms of the enzyme could have developed in sepsis thereby increasing its potential to cause myocardial depression. Aliquots of the septic and nonseptic preparations were added (at 5 minute intervals) to respective organ baths, and the changes in isometric tension were then compared between Lzm-S obtained from spleens of septic and nonseptic animals.

In subsequent experiments, the objective was to determine whether pretreatment of Lzm-S with the proteolytic enzyme proteinase-K reduced the extent to which myocardial depression developed in the in vitro preparation (7). Proteinase-K (attached to beaded agarose; Sigma Chemical, St Louis, Mo.) was added to the pure Lzm-S preparation. The effects of proteinase-K treated and nontreated Lzm-S on isometric tension were compared between the samples. Since proteinase-K is a non-specific proteolytic enzyme, a specific competitive inhibitor of lysozyme, TAC (chitotriose) was subsequently examined to determine whether it prevented the depression in isometric tension observed in the in vitro preparation (16,17). TAC is the trisaccharide of N-acetylglucosamine (NAG) that has three NAG residues linked by beta (1-4) glycosidic linkages that competitively inhibits the enzymatic activity of Lzm-S.

In one set of experiments, it was determined whether TAC prevented the reduction in tension observed with Lzm-S. A dose of $10^{-3}$M TAC (based on preliminary experiments) was added to the organ bath before the addition of Lzm-S. Lzm-S was then added to bring the final concentrations to $10^{-10}$M, $10^{-9}$M, $10^{-8}$M, and $10^{-7}$M in sequential steps. In a related set of experiments, the effect of TAC was studied under a similar protocol in which the ventricular trabecular preparation was paced at 1 Hz instead of 0.5 Hz. The objective was to determine whether the higher frequency altered the inhibitory response of TAC. In a third set of experiments, the sequence of adding TAC and Lzm-S was reversed. Lzm-S ($10^{-7}$M) was initially added to the preparation, after which TAC at bath concentrations of $10^{-6}$M, $10^{-5}$M, $10^{-4}$M, $10^{-3}$M were sequentially added. The objective was to determine whether TAC could attenuate the effect of Lzm-S on reducing the isometric response after an initial depression in isometric tension had already been attained.

Effect of Lzm-S on Adrenergic Function

Since myocardial depression in sepsis may also be related to a diminished sympathetic response, the possible role of Lzm-S in contributing to this effect was additionally investigated in the right ventricular preparation as previously described (18). Neural adrenergic stimulation was produced in which the pulse width of the electrical stimulus-trains was increased from 2 ms to 20 ms, keeping other stimulus parameters unchanged. The increase in tension seen with sympathetic nerve stimulation was calculated as a percent increase from basal twitch amplitude. In the protocol used, the adrenergic response was measured before and after $10^{-10}$M, $10^{-9}$M, and $10^{-8}$M Lzm-S were added to the organ bath. The results obtained with Lzm-S were compared with those obtained in time control experiments in which equal volumes of KH were added to the preparation at identical intervals. In a second set of experiments, it was observed whether TAC prevented the decrease in the adrenergic response produced by Lzm-S. Either TAC ($10^{-4}$M) or KH was added to an organ bath, and the results obtained with TAC treatment were compared with those obtained without the addition of the inhibitor.

In a third set of experiments, the effect of lysozyme ($10^{-8}$M) on inhibiting the adrenergic response to the β-agonist isoproterenol ($10^{-8}$M) was examined in the right ventricular preparation in which the muscle was paced at 0.5 Hz. The change in basal twitch tension after isoproterenol was added to the lysozyme treated preparation was compared to that found in the nontreated preparation. The objective was to determine if the β-adrenergic effect of exogenous catecholamines could be inhibited by lysozyme in the in vitro preparation.

Statistical Analysis

Statistics comparisons between groups were made by means of a two way repeated measures analysis of variance (ANOVA) (factor A, different treatment groups; factor B, different time periods). A Student-Newman-Keuls' (SNK) multiple range test was used to determine where differences occurred. In the analysis of plasma fractions F1, F2, F3 (see FIG. 1), 11 animals were used. Based on reference 7, this number gave us 80% power to detect a difference of 10% between pre and sepsis samples. In the gel experiments, 24 animals were necessary because many types of experiments were performed on the plasma samples obtained, and a lot of the protein was lost in the preparation of the samples. Results are reported as mean±1SE.

Results

In the separation procedures outlined, the 10-30 KD pre and septic plasma fractions, initially obtained by pore filtration techniques, were passed through a SEC-HPLC column for further purification, and the eluents from the respective samples were divided into three fractions termed F1, F2, and F3. The results shown in FIG. 1 indicate that there was a significant increase in depressant activity found in the F2 fraction, but not in the other fractions. In the F3 fraction, depression in the septic fraction was slightly less than that found in the preseptic fraction. It is interesting to note that even in the preseptic sample, there is some background depressant activity (BDA) that is found in all samples. As described in a previous study (7), the nature of BDA is not yet defined, but it appears to be of lipid moiety with different physical properties as compared with FCS. The increase in depressant activity in sepsis therefore does not represent an increase in BDA, but the formation of a new substance, ie. FCS. For this reason, it has been our approach in defining the nature of FCS to compare pre and septic plasma fractions taken from the same dog. An increase in depressant activity found in a sepsis fraction relative to that found in the presepsis fraction is indicative of the formation of FCS.

Figure 1A:
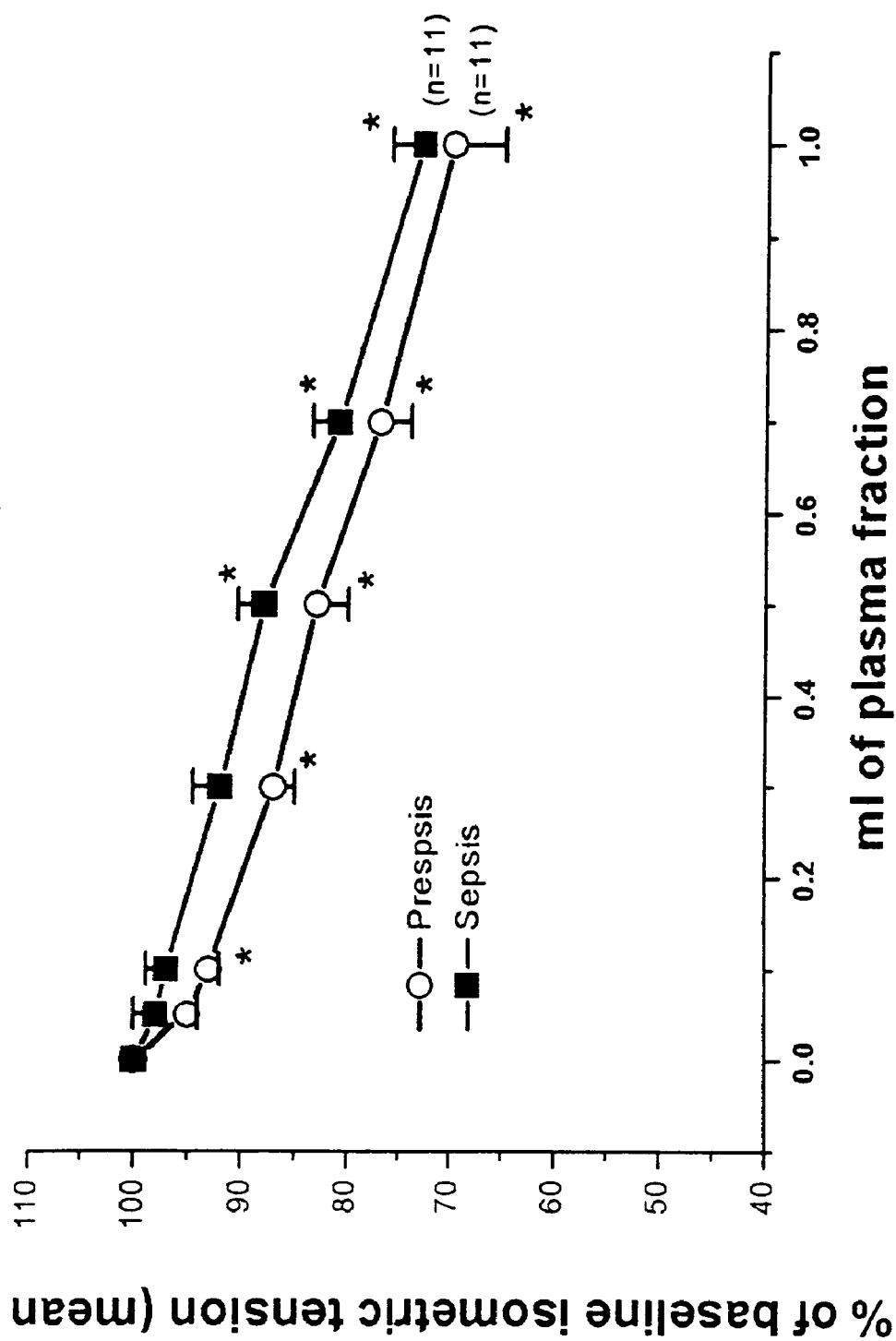
Figure 1B:
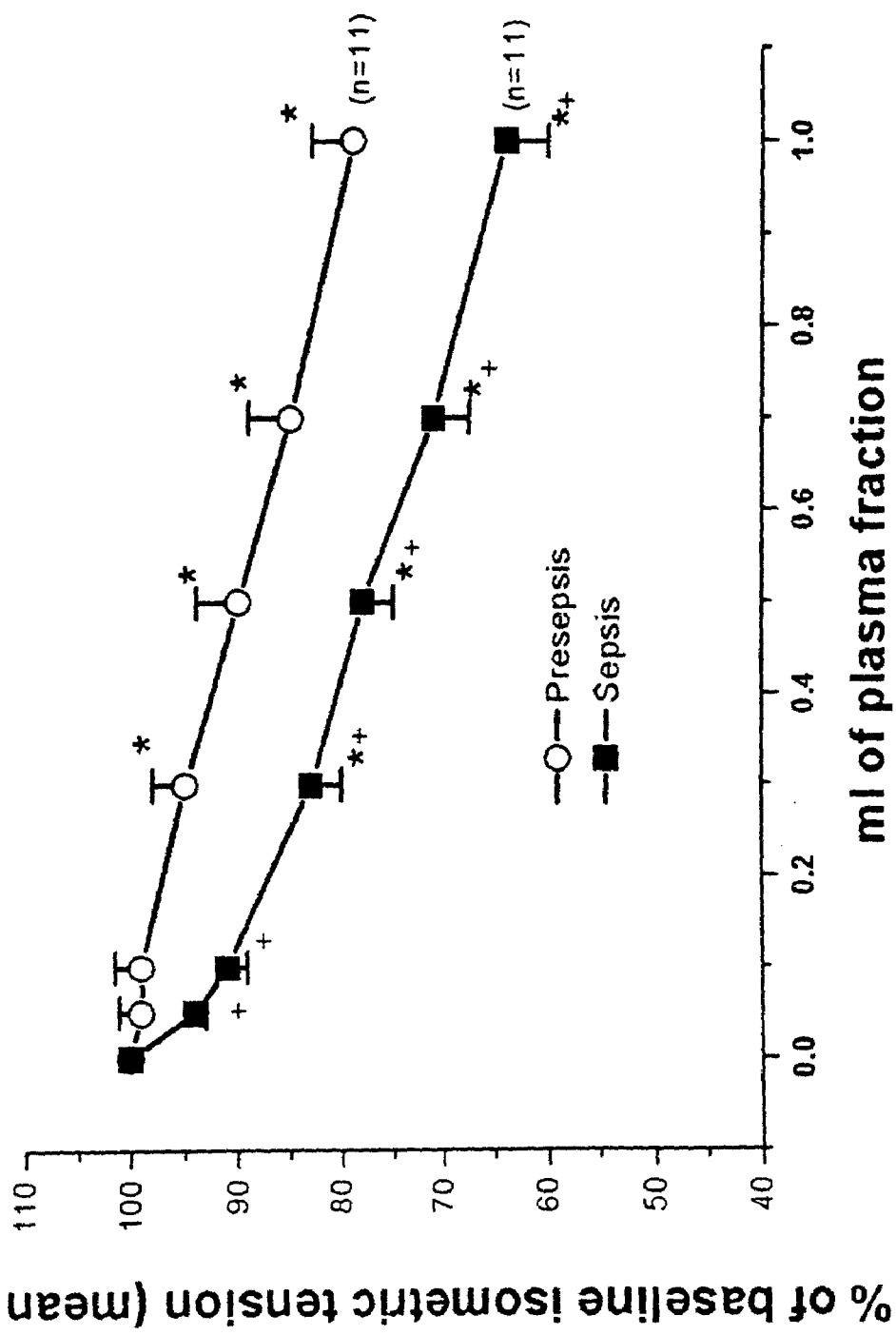

From the respective F1, F2, and F3 fractions, a SDS-PAGE gel was prepared that represented the pooled sample of 24 dogs obtained from the pre and sepsis samples (see FIG. 2: note that some of the dogs used in the gel preparation were not studied in the organ bath shown in FIG. 1). In FIG. 2, the F1 and F3 fractions showed no differences in bands between the two fractions. However, in the F2 fraction, a broad band was identified at ~15 KD in the septic sample, but not in the nonseptic (control) sample and as noted above that contained FCS activity. The substance depicted in the gel was identified as canine spleen lysozyme with a high degree of confidence by both physical and chemical sequencing techniques (8,9, 11).

In addition to the plasma, evidence of myocardial depressant activity was also examined in the spleen, heart, and lymphocytes. In terms of the inventors' hypothesis (see Discussion), the heart was thought to be the target organ of FSC; the spleen was considered to be the source organ of FCS, while lymphocytes were not thought to be involved either in the formation or the action of FCS. When expressed per ml of organ homogenate, the results showed that as compared with the presepsis sample, in the septic sample, increased depressant activity was found in the spleen and heart, while no increase was found in the lymphocyte fraction (see FIG. 3). Purified Lzm-S was additionally prepared from spleens taken from septic and nonseptic dogs, and the results showed a marked decrease in isometric tension that occurred to a similar extent in both preparations (FIG. 4A); time control experiments in which KH was placed into the organ bath over an identical interval showed only small changes in tension. Thus, when standardized on a milligram basis of pure Lzm-S, no differences in activity could be observed between the septic and nonseptic preparations, these results suggesting that more leukocytes contained in the organ sample contributed to the increased depressant activity found in septic spleens (see Discussion).

The activity of purified Lzm-S, as determined by the turbidometric method of Shugar (15), was found to be $4.4 \times 10^4$ international units per mg of Lzm-S. Lzm-S activity was then determined in the pre and septic plasma fractions, and the results were 20 units/ml and 70 units/ml, respectively. The latter values would correspond to a negligible amount detected in the presepsis sample (i.e beyond our ability to define a specific amount below $10^{-10}$M) while in the septic sample, this activity would correspond to a Lzm-S concentration of $10^{-8}$M (see below).

Figure 4A:
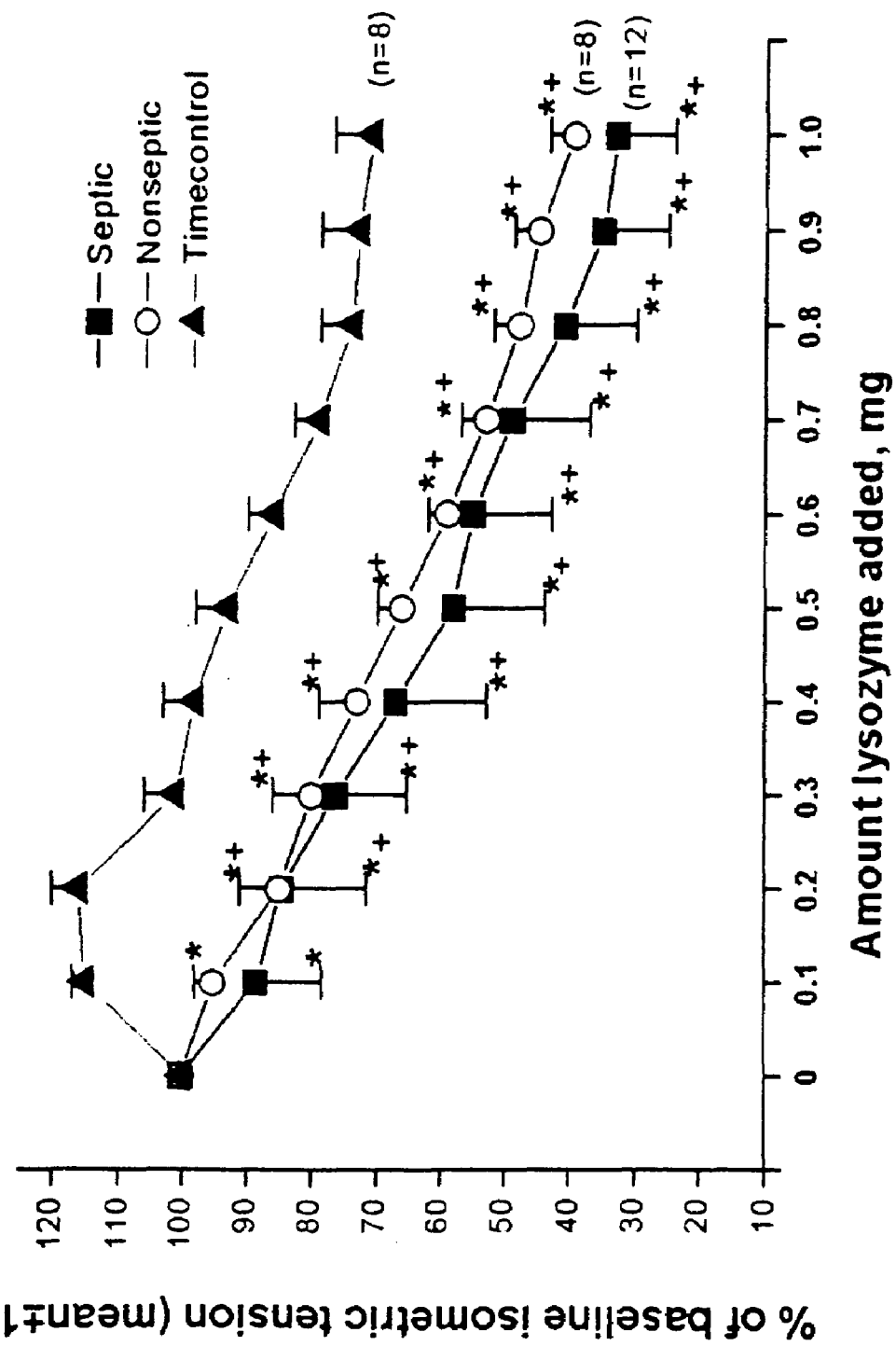
FIG. 4A is a graph showing that Lysozyme (Lzm-S) was prepared from the spleens of animals subjected to 4 hrs of sepsis (septic) and spleens of animals subjected to normal saline infusion (nonseptic). Lzm-S was placed into the in vitro bath and the change in tension was recorded. There was no difference in the depressant effect (mean±1SE) found between the two splenic preparations. In the time control experiments, an identical amount of KH was placed into the bath over the interval of the experiment. Accordingly, as assessed by per gram weight of spleen in FIG. 3, the septic spleens showed a greater degree of depression than the nonseptic spleens, but when purified lysozyme was compared between septic and nonseptic spleens on a milligram basis, no difference was observed between the two preparations. Since there may be more polymorphonuclear cells found in septic spleens, the quantity of lysozyme would be greater than that found in nonseptic spleens, but the potency of depressant activity may not be different between preparations (see Discussion in Example 1). By two way ANOVA and SNK, *$P<0.05$ vs baseline; +$P<0.05$ vs time control group.
Figure 4B:
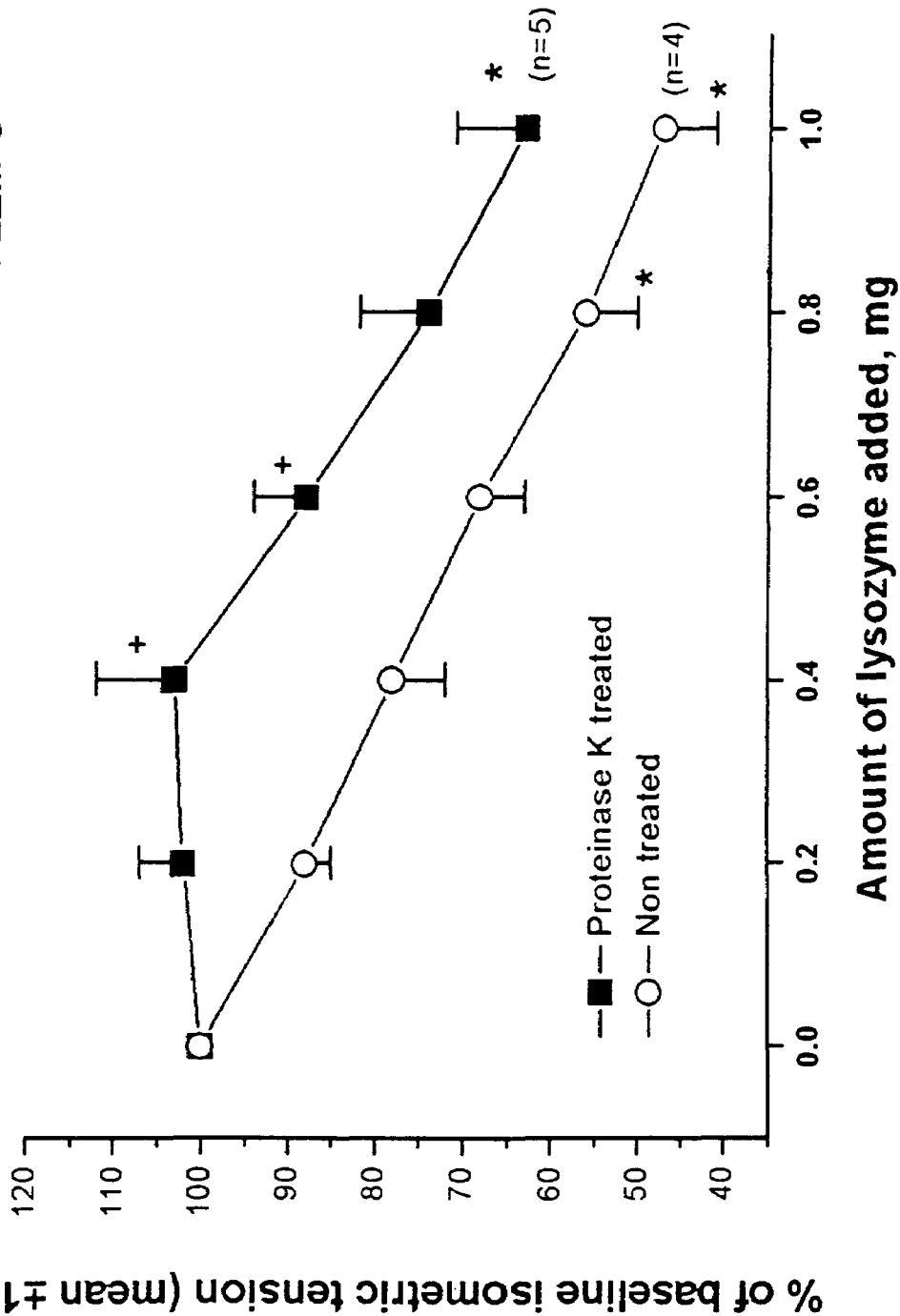
FIG. 4B is a graph showing that proteinase K treated Lzm-S caused less depression than the untreated sample at the lower lysozyme concentrations. Mean (±1SE) values are given. By two way ANOVA and SNK, *$P<0.05$ vs baseline; +$P<0.05$ treated vs nontreated groups.

Non-specific and specific inhibitors of Lzm-S were used to determine whether the depression by Lzm-S could be attenuated in the in vitro preparation. In one group of experiments (see FIG. 4B), Lzm-S was treated with proteinase K which is a nonspecific proteolytic treatment. Proteinase K treatment caused a reduction in depressant activity as compared to the untreated sample that was most apparent at the lower concentrations of the treated sample.

Figure 5A:
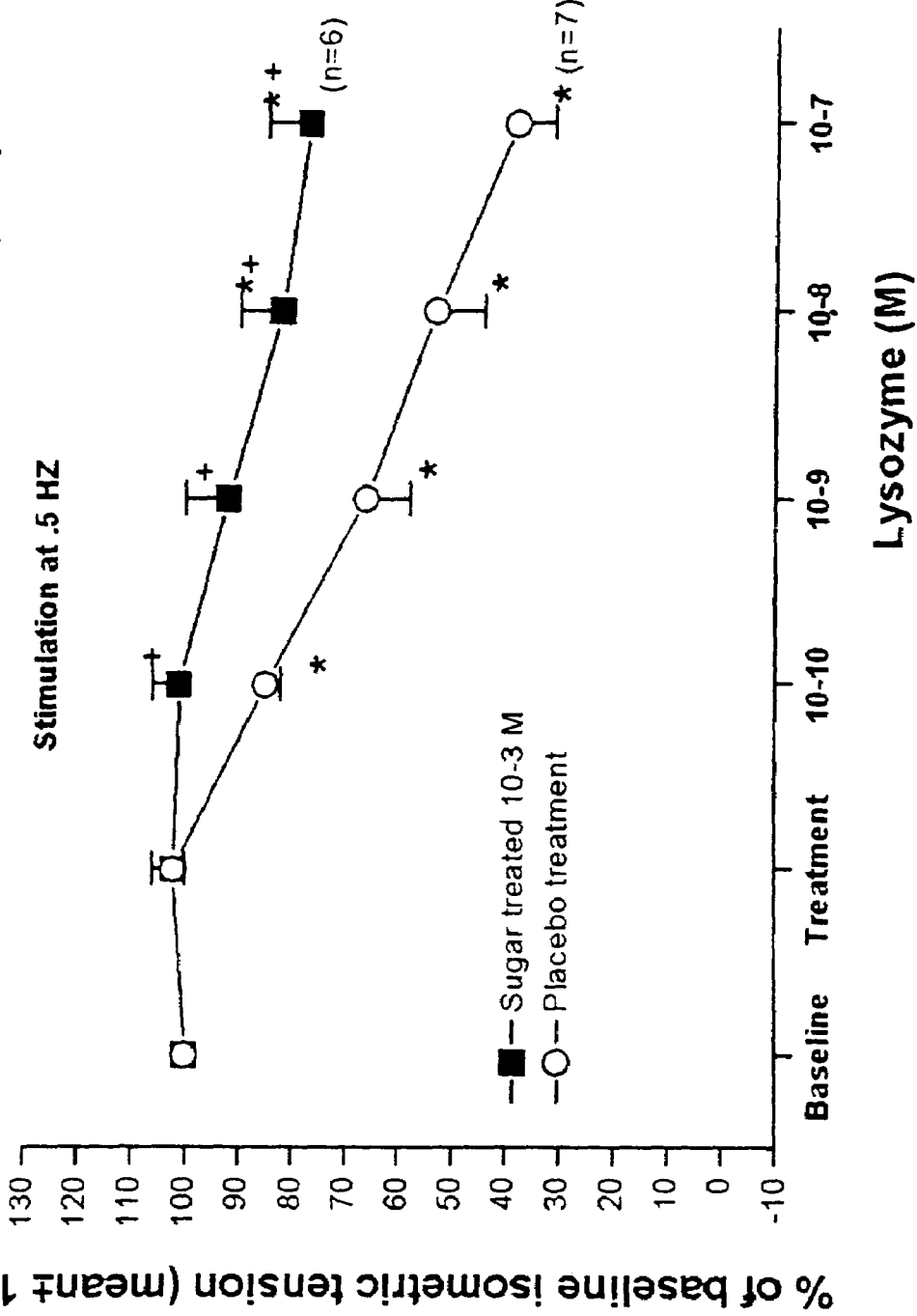
Figure 5C:
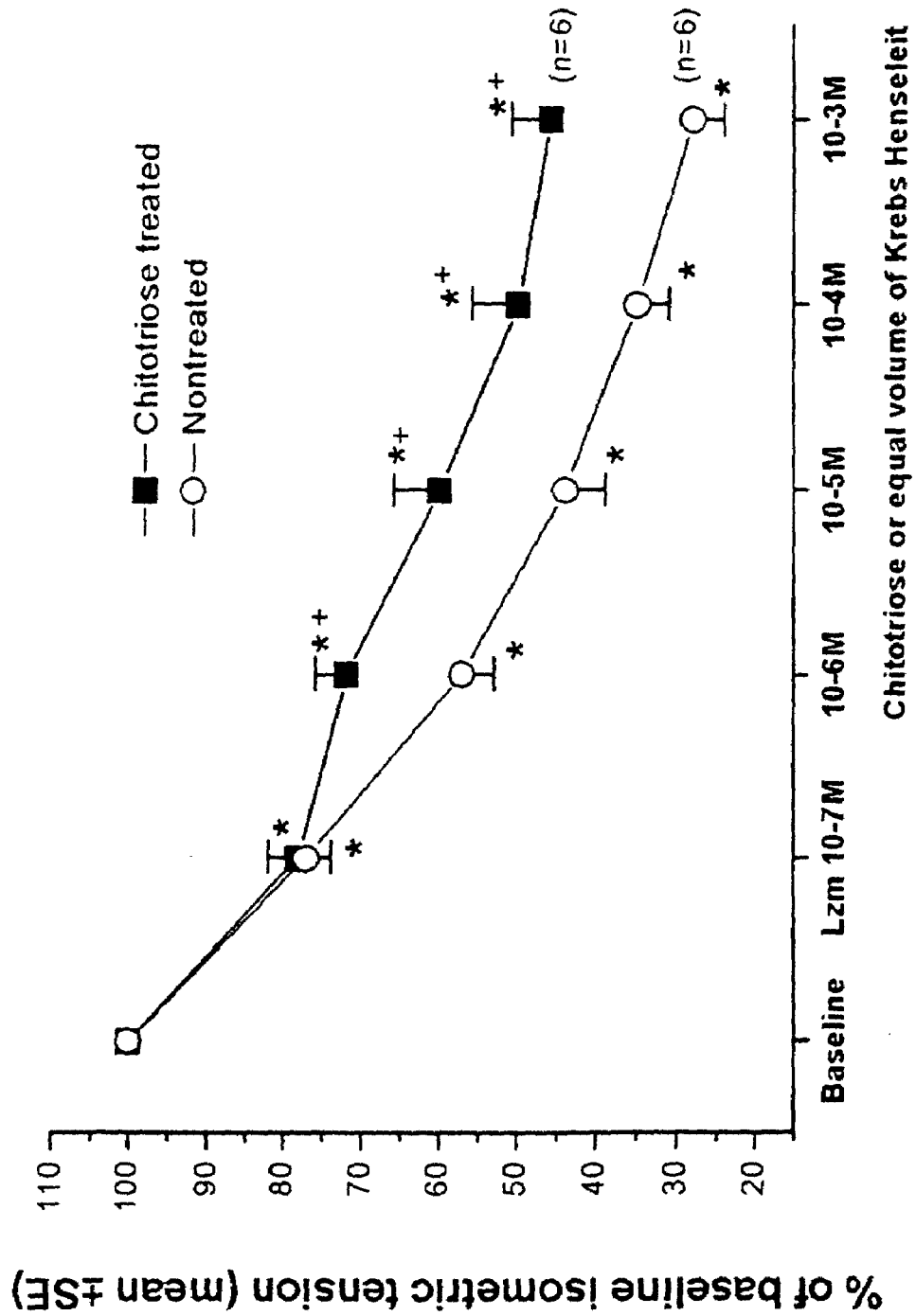

In FIG. 5A, TAC (chitotriose) ($10^{-3}$M), a competitive inhibitor of Lzm-S, was added to the bath prior to the addition of Lzm-S. As compared with the baseline condition, TAC itself had no effect on isometric tension. However, with subsequent addition of Lzm-S, the depression in isometric tension observed in the TAC treated group was significantly less than that found in the nontreated group. In FIG. 5B, the pacing rate of the trabecular preparation was increased from 0.5 Hz to 1 Hz. The objective was to determine whether the effect of TAC ($10^{-3}$M) on attenuating the depressant activity of Lzm-S was still observed at this higher heart rate and this indeed was the case. In FIG. 5C, Lzm-S was added to the organ bath before rather than after the addition of TAC, and the results showed that even after myocardial depression had been initiated by Lzm-S, treatment attenuated the reduction in isometric tension as compared with the nontreated group.

Figure 6:
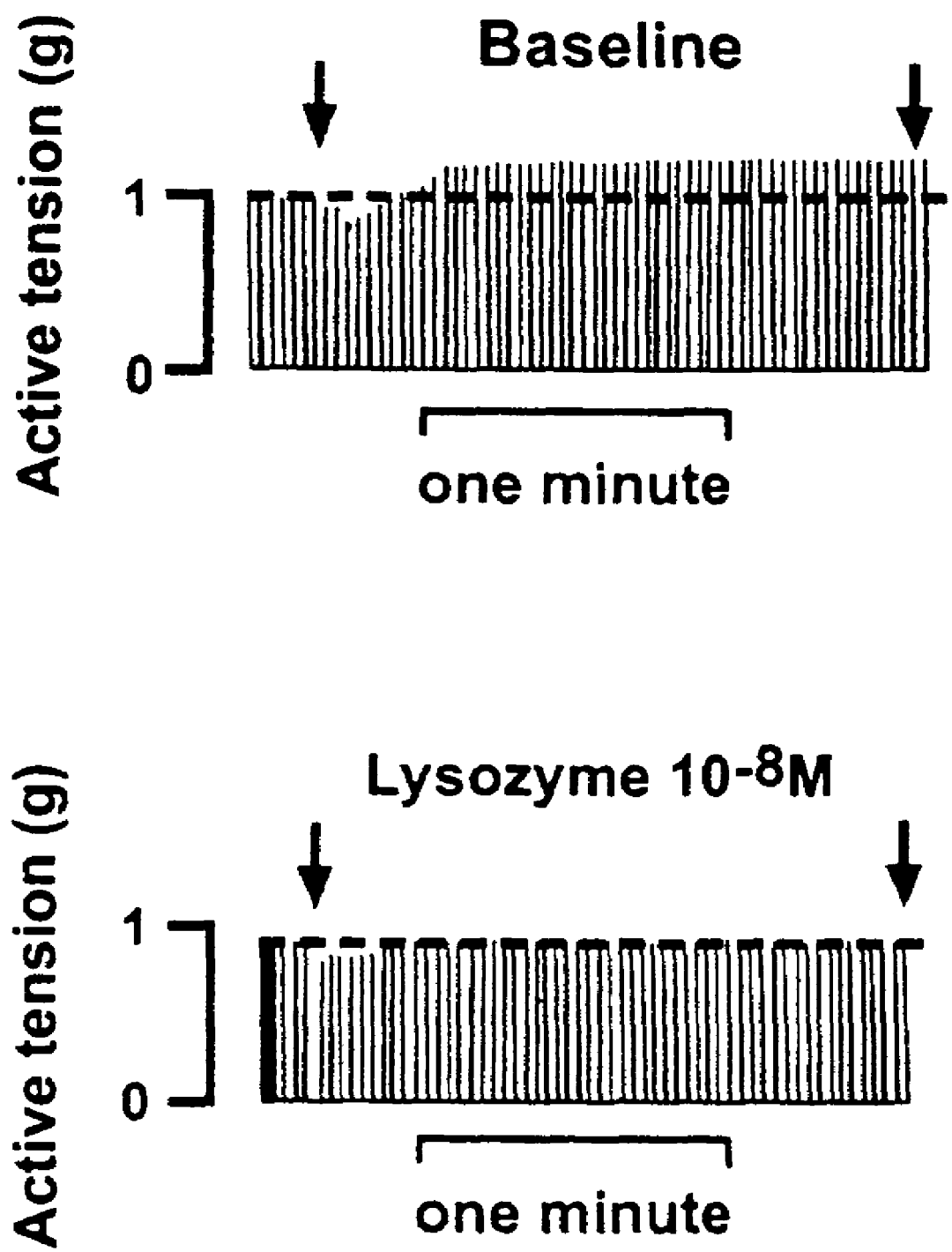
FIG. 6 shows the sympathetic response to field stimulation in the ventricular trabecular preparation at baseline (upper panel) and after treatment with lysozyme (lower panel) in which isometric tension is plotted against time. Adrenergic response is indicated by interval between arrows. Small dip in isometric tension at beginning of stimulation is believed to represent effect of synchronization, and may be due to abnormal conduction of action potential when sympathetic stimulation is initially applied and then stopped (18). Horizontal dashed line represents basal tension. At baseline, the adrenergic response increased approximately 25%, while there was no increase when lysozyme was added to the preparation.
Figure 7C:
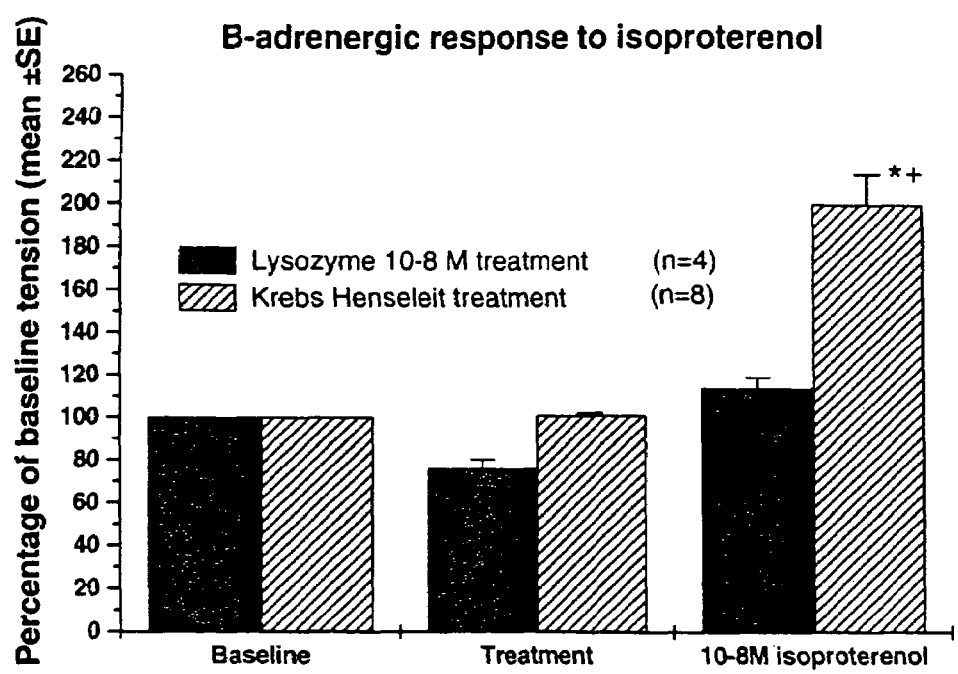

In another set of experiments, the effect of Lzm-S on the adrenergic response was determined. In the example in the upper panel in FIG. 6, no Lzm-S treatment was administered, and the increase in adrenergically mediated contractile response was approximately 25%. In the lower panel, Lzm-S was administered and the response was near zero. In FIG. 7A, mean values are shown. In the time control group, the adrenergic response was unchanged as compared to the baseline value, while in the Lzm-S treated group, the adrenergic response progressively decreased when higher concentrations were added to the preparation. In FIG. 7B, pretreatment with TAC prevented the reduction in adrenergic response otherwise found when Lzm-S was added without the inhibitor. In FIG. 7C, the adrenergic response to the β-agonist isoproterenol was associated with significantly less increase in isometric tension in the lysozyme treated preparation as compared with the nontreated preparation.

Discussion

The significant finding of this study is that Lzm-S contributes to myocardial dysfunction in experimental sepsis. It is important to note that the inventors' approach to identifying this depressant factor was different from that used by other investigators (19,20). Rather than to postulate a priori that a specific substance, such as endotoxin, cytokines, etc, was accountable for causing myocardial depression in sepsis, the inventors initiated this study without preconceived notion about what the nature of this substance could be. The inventors obtained plasma from the septic animal and used the right ventricular trabecular assay to determine whether a given plasma fraction developed cardiac depressant activity over 4 h of bacteremia. The inventors always compared pre and septic plasma fractions that were obtained from the same dog because the presence of background myocardial depressant activity would otherwise confound the interpretation of the data. Eventually, the inventors were able to purify myocardial depressant factor, and this factor was identified as Lzm-S.

Grobler et al (14) sequenced canine spleen lysozyme and the molecular weight calculated from the amino acid sequence was 14,578 and thus fits well with the molecular weight identified as FCS in the present study.

Once the nature of FCS was identified, the inventors were able to show that purified Lzm-S caused myocardial depression in a manner identical to that produced when the 10-30 KD septic plasma fraction was added to the in vitro preparation. The inventors then showed that its effect could be blocked by the nonspecific proteolytic enzyme proteinase K, and more importantly by TAC, a competitive inhibitor of Lzm-S. The inventors also demonstrated that TAC was able to attenuate the depressant effect of Lzm-S when given either before or after Lzm-S was added to the in vitro preparation. The inventors also confirmed that the concentration of Lzm-S required to cause myocardial depression in the in vitro preparation was comparable to that found in vivo. In the presepsis plasma fraction, the concentration of Lzm-S was low and insufficient to cause myocardial depression while it increased to $10^{-8}$M in the septic plasma fraction, a concentration that was shown to produce a decline in isometric tension of approximately 50% in the in vitro preparation. Therefore, based on the in vitro findings, the concentration found in vivo would be sufficient to cause left ventricular dysfunction in our model.

In an earlier study, Burgess et al (21) used elevations in serum lysozyme as a marker to diagnose the development of an occult intraabdominal abscess in critically ill patients following trauma. Lysozyme activity was found to increase over the course of hospitalization in septic patients with intraabdominal abscess, while activity did not increase in nonseptic control groups. Burgess et al (21) measured serum lysozyme activity in a manner similar to the present study and found that a mean value of 39 units/ml was reached in their septic patients. Although their value was lower than the mean value of 70 units/ml found in the septic plasma fraction in the present study, the patients described by Burgess et al (21) were not in septic shock and hemodynamic measurements were not obtained.

In the present study, the decline in myocardial tension observed with Lzm-S occurred within 5 minutes, and thus its mechanism of action would favor a direct effect of this agent on the myocardium. Many mechanisms of cardiac depression induced by sepsis have previously been postulated. Among others, these involve the effects of inflammatory mediators on releasing cytokines that would in turn cause myocardial depression through changes in signal transduction, or through mechanisms that would promote cell death by means of apoptotic pathways in the heart (19,20,22). However, such mechanisms would occur in hours rather than minutes and would not fit with the rapid effect observed in the in vitro preparation. The inventors know, moreover, that an intact membrane is required for action of Lzm-S (23). The inventors showed in a skinned ventricular preparation, that the addition of the septic plasma fraction did not affect myofilament tension, while it did so in the intact muscle. The inventors think, therefore, that Lzm-S probably decreases myocardial contraction by interfering with membrane function and that this interference must occur at an extracellularly orientated site in accordance with the biochemical properties of the enzyme described below.

Lysozyme is a bacteriolytic agent originally identified by Fleming in 1922 in mucus (24). Lysozyme has been shown to catalyse the hydrolysis of N-acetyl-D-glucosamine (NAG) to N-acetylmuramic acid (NAM) linkages of bacterial cell walls thereby disrupting the bacterial cell (16,17). It also exists among the cells of the blood exclusively in neutrophilic granulocytes and monocytes, whereas in tissues, the greatest concentrations are found in the bone marrow, lungs, intestines, spleen, and kidneys (25). Plasma lysozyme is believed to stem mainly from disintegrating neutrophilic granulocytes, and the high concentrations that are found in bone marrow, lung, spleen, and intestine have been suggested to relate to the breakdown of granulocytes located in these organs (25-27). In the present study, the inventors have used the term Lzm-S rather than lysozyme c, since from the standpoint of the present results, lysozyme identified by the sequencing analyses could have arisen from the source organ, ie the spleen or leukocytes arising from that organ, or possibly from other organs.

Figure 3A:
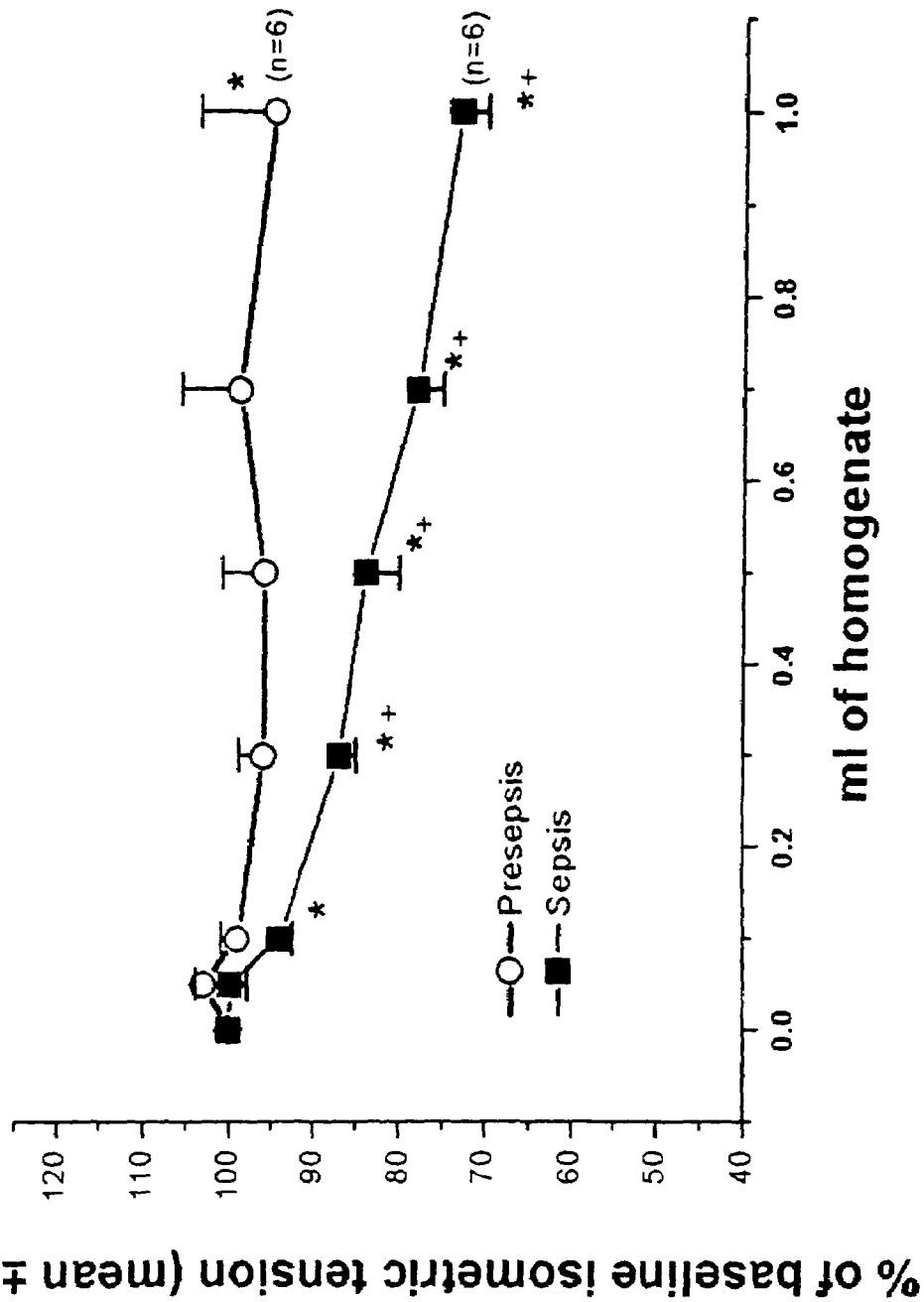
Figure 3B:
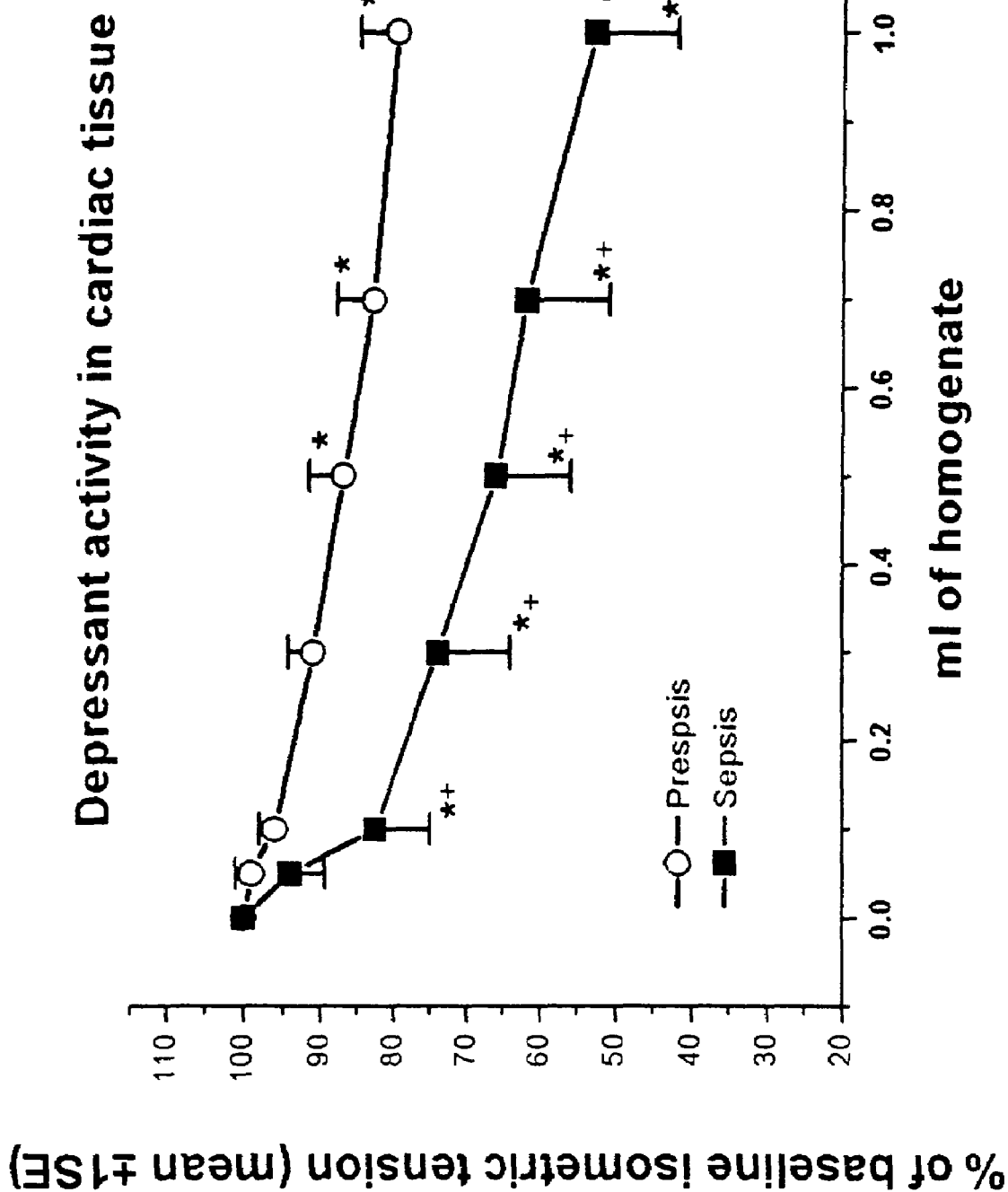

In FIG. 3, the inventors compared the cardiodepressant activity in spleens taken from septic versus nonseptic animals and demonstrated that depressant activity increased in the septic spleens. As assessed by per gram weight of spleen, the septic spleens showed a greater degree of depression than the nonseptic spleens. However, when purified lysozyme was compared between septic and nonseptic spleens on a milligram basis, no difference was observed between the two preparations. Since there may be more polymorphonuclear cells found in septic spleens, the quantity of lysozyme would be greater than that found in nonseptic spleens, but the potency of depressant activity would not be different between preparations (see FIG. 4).

The mechanism of action of lysozyme in causing cardiac depression is a very interesting question. In the heart, most membrane proteins are posttranslationally modified, are heavily N-glycosylated, and therefore are glycoproteins (28-30). In turn, changes in the N-glycosylated regions may affect membrane function and may alter myocardial contraction. The inventors consider two possibilities about how Lzm-S may affect membrane function by acting on a glycoprotein. In one mechanism, lysozyme binds to an extracellularly saccharide-bearing structure and hydrolyses the bond between two monosaccharide units, such that this hydrolysis causes the biological effect of a decrease in myocardial contraction. Alternatively, lysozyme binds to an extracellulary orientated saccharide bearing structure, is unable to hydrolyse it, but because of its binding induces a conformational change of the carbohydrate tree and the glycoprotein bearing it. This conformational change causes the biological effect of a depression in myocardial function. For lysozyme to cause hydrolysis, the presence of a vicinal NAG-NAM structure is required, while for binding alone, a structure containing NAG-NAG should be sufficient (16,17). The inventors believe that binding to a NAG-NAG membrane structure is the most likely possibility.

In terms of the relation of the inventors' results to previous studies, Hansen et al (26,27) measured plasma lysozyme concentrations in nonseptic humans and found a mean plasma concentration of 2.4 µg/ml in 24 individuals, although more recent studies suggest that the amount is much less and approximates 1 µg/ml (31). The higher concentrations found in some individuals in the studies of Hansen et al (26,27) may be close enough to cause myocardial depression as ascertained by our in vitro preparation. However, when previous studies are considered, some additional aspects need to be entertained. Firstly, myocardial function was never systematically investigated in these patients, so that changes may not have been detected. Secondly, the sensitivity of the myocardium of human subjects to lysozyme may be less than that found for canine myocardium and this aspect needs to be elucidated. Thirdly, it is not clear the extent to which plasma lysozyme represents the actual concentration found in the myocardium. Since lysozyme is a relatively large molecule, some permeability of the vascular endothelium as that which occurs in sepsis may be required for an increase in myocardial concentrations to occur.

In summary, the present findings indicate that Lzm-S originating from disintegrating leukocytes (i.e. predominantly neutrophils) from organs such as the spleen contributes to myocardial dysfunction in this model. In other studies (32), leukocytes have also been shown to be an important component in causing myocardial dysfunction in sepsis. Although histology was not performed in this study, Granton et al (32) found neutrophils in hearts of animals subjected to bacteremia, and close proximity of activated neutrophils would expose myocardium to high concentrations of Lzm-S. The inventors hypothesize that Lzm-S causes myocardial dysfunction by binding to a carbohydrate portion of a membrane glycoprotein. This binding leads to a conformational change of the carbohydrate portion and the anchoring protein portion of the glycoprotein. Alternatively, Lzm-S can cleave part of the carbohydrate structure which would also lead to a conformational alteration of the glycoprotein. Such actions could interfere with myocardial excitation contraction coupling in sepsis.

Example 2

N,N',N" Triacetylglucosamine, an Inhibitor of Lysozyme, Prevents Myocardial Depression in *E. coli* Sepsis in Dogs Objection The inventors previously found that lysozyme c (Lzm-S), consistent with that originating from the spleen, was a mediator of myocardial depression in an *Escherichia coli* model of septic shock in dogs (Example 1). The inventors further showed in a right ventricular trabecular preparation (RVT) that Lzm-S's depressant activity could be blocked by N,N',N" triacetylglucosamine (chitotriose or TAC), a competitive inhibitor of Lzm-S. The inventors hypothesized that Lzm-S binds to or cleaves a cardiac membrane glycoprotein thereby interfering with myocardial contraction in sepsis. In the present study, the inventors examined whether TAC could prevent myocardial depression in an in vivo preparation and whether other related NAG structures could also inhibit Lzm-S's effect in RVT.

In one part of the present study, the effect of TAC on myocardial function when treatment was intravenously administered at various time intervals in the *E. coli* model was examined. Treatment was administered prior to the induction of sepsis (Pretreatment Study), 1.5 hrs after sepsis was induced (Early Treatment Study: ETS), and after 3.5 hrs of sepsis was induced (Late Treatment Study: LTS) in respective experiments. In the Pretreatment Study and ETS, myocardial depression would not have as yet occurred in the model, while myocardial depression would have been present in LTS (12). It could therefore be determined whether TAC could prevent the development of myocardial depression in the Pretreatment Study and ETS and whether it could also reverse myocardial depression that had already occurred in LTS.

In a second part of this study, it was determined whether deglycosylation of N-linked oligosaccharides from cardiac membrane glycoproteins to which Lzm-S would bind would result in a lessening of Lzm-S's depressant effect. This would provide additional evidence that the carbohydrate portion of the cardiac membrane glycoprotein was important in Lzm-S's myocardial depressant effect. Furthermore, the inventors tested a series of NAG oligosaccharides and variants to the NAG structure as inhibitors of Lzm-S's depressant activity in the right ventricular trabecular preparation (17,12).

The primary objective of the present study was to examine whether TAC or related lysozyme inhibitors would be potentially useful in the treatment of cardiovascular collapse in sepsis.

Methods

These experiments were approved by the University Animal Care Committee and conform with the Guide for the Care and Use of Laboratory Animals published by the US National Institutes of Health (NIH Publication No 85-23,1996) (10).

In vivo Experiments

In all of the studies outlined, the animals were randomized into treatment and nontreatment placebo groups (see below). The *E. coli* model used in these studies was identical to that previously described (6). Sepsis was induced by the intravenous infusion of $10^{10}$ colony forming units of live *E. coli* (designation 011:B4). The bacteria were suspended in normal saline solution and were given over 0.5 hour. A constant infusion of approximately $5 \times 10^9$ colony forming units/hour of *E. coli* was then maintained for the remainder of the experiment.

The animals (16-24 kg) were initially anesthetized with thiopental sodium (20 mg/kg, intravenously) and constantly infused with sufentanil citrate (1 ug/min) and midazolam (5 ug/kg/min) (33). Drug rates were adjusted as required to abolish the palpebral reflex. The animals were placed in the supine position; the trachea was intubated with an endotracheal tube; and the lungs were mechanically ventilated at a tidal volume of 20 ml/kg. The ventilator rate was initially set to maintain blood pH at approximately 7.35 and was increased as necessary to reverse the metabolic acidosis that developed over the course of the study. Approximately 100% oxygen was inspired, so that hypoxemia would not affect the results of the study.

Under sterile conditions, the right jugular vein was percutaneously cannulated with an introducer (Arrow International, Reading, Pa.). A thermister tipped catheter was advanced from the jugular vein into the pulmonary artery to measure mean pulmonary arterial pressure (Ppa), mean pulmonary capillary wedge pressure (Pwp), mean right atrial pressure (Pra), thermodilution cardiac output (CO, Columbus Instruments, OH), and to obtain mixed venous oxygen blood samples. Another introducer was placed into the left jugular vein for administration of intravenous saline solution and the treatment or placebo drug (see below). A polyethylene catheter was also percutaneously placed into the femoral artery to measure mean blood pressure (MAP), and to obtain samples of blood for blood gas analysis, blood hematocrit (Hct), lactate concentrations, and blood cultures in some cases. Lactate was measured by an automated lactate dehydrogenase based assay (34) and was performed only in ETS and LTS because of equipment difficulties in the Pretreatment Study.

All catheters were connected to transducers (Cobe Laboratories), were referenced relative to the left atrium and were connected to a chart recorder (Astro-Med, W Warwick, R.I.). Heart rate (HR) was measured from the recorder tracing. Stroke-volume (SV) was calculated as CO/HR. Systemic vascular resistance (SVR) was calculated from [(MAP-Pra)/CO]×80. At each measurement interval (see below), a full set of measurements included MAP, CO, Ppa, Pra, Pwp, Hct, HR, SV, and arterial and mixed venous blood samples.

In the analysis, stroke work (SW) was the primary index of cardiac performance and the primary hemodynamic endpoint chosen in the in vivo studies (35,18) (see Discussion). At constant preload, SW reflects both the decreases in afterload and the changes in contractile function that accompany sepsis. SW was determined at approximately the same Pwp at each measurement interval. The baseline Pwp usually averaged ≈8-10 mmHg, and normal saline solution was given as necessary to maintain Pwp constant over the experimental period. SW was calculated from SV (MAP-Pwp).

Experimental Protocols

Pretreatment Study. In the Pretreatment Study, TAC was given before the bacteria were infused. Based on previous studies, it takes approximately 3 to 4 hours of constant bacteremia in order for myocardial depression to develop in this model (6,18). A three to five hour course of bacteremia was therefore considered necessary to determine if TAC could block the decline in SW observed at this interval. In the pretreatment protocol, measurements were obtained at baseline, after administration of treatment or placebo, and then after 3 h and 5 h of continuous *E. coli* infusion (see schematic of protocol in FIG. 8).

The dose of TAC used in the Pretreatment Study was based on calculations previously obtained from the ventricular trabecular experiments in which it was estimated that a plasma concentration of at least $10^{-5}$M would be required to inhibit lysozyme's depressant activity in vivo (49). Based on the molecular weight of TAC (628 MW), the average size of the dog (20 kg), and the estimated distribution space of approximately 50% of total body weight, the dose chosen was 100 mg (Sigma Corp, Canada, Oakville, Ontario) mixed in 200 ml 5% dextrose in water ($D_5W$) that was given intravenously over 0.5 hr. After this initial dose, a dose of 50 mg mixed in 50 ml $D_5W$ was continuously infused over each hour for the remainder of the study. The placebo group received an identical amount of $D_5W$ over the course of the study. In the pretreatment group, blood cultures were obtained to make sure that TAC did not affect the viability of the organism infused.

Late Treatment Study. In LTS, the objective was to see if TAC would reverse myocardial depression once it had already been produced. TAC was administered after 3.5 hours after the initiation of bacteria and was given over a 0.5 hour in 200 ml $D_5W$. Because it was also noted in the in vitro trabecular preparation that once lysozyme was already placed into the bath, a higher concentration of TAC was required to inhibit the effect of lysozyme, the initial dose was increased to 250 mg in LTC. After this initial dose, as in the Pretreatment Study, a dose of (50 mg mixed in 50 ml $D_5W$)/h was given over the remainder of the study. The placebo group received an identical amount of $D_5W$ per over the course of the study. In LTS, measurements were obtained at baseline, after 3.5 hours of bacteremia, immediately after treatment or placebo, and 2 hours after TAC or placebo treatment was administered (i.e. 6 h postsepsis; see FIG. 8).

Early Treatment Study. The purpose of this study was to assess the effect of TAC when treatment was administered during sepsis, but before myocardial depression developed. Treatment was administered at 1.5 hours after bacteremia was begun (6). Based on the lack of response of some animals in the LTS, the initial dose of TAC was increased to 400 mg, and followed by 50 mg/h mixed in 50 cc $D_5W$ over the remainder of the study. The placebo group received an identical amount of $D_5W$ over the course of the study.

In vitro Experiments

The right ventricular (RV) preparation used in this study has also been described (49,6). Briefly, mongrel dogs (3 to 10 kg) were anesthetized with pentobarbital. The hearts were removed, flushed with 50 ml of Krebs-Henseleit solution (KH), and placed in ice-cold KH bubbled with a mixture of 95% $O_2$ and 5% $CO_2$. Three to four thin trabeculae (<1 mm diameter) were obtained from the right ventricle and were tied at each end with 6-O silk thread. Each thin muscle was suspended in a vertical constant temperature bath (5 ml) that contained KH (in mM: NaCl, 118; KCl, 4.7; $CaCl_2$ 2.5; $MgSO_4$, 1.2; $KH_2PO_4$, 1.4; $NaHCO_3$, 25; and dextrose, 11). The muscle was stimulated electrically via punctate platinum bipolar electrodes with rectangular pulses (1 ms duration) at an intensity of 50% above threshold delivered at intervals of 2,000 ms. The trabeculae were stretched to optimal length.

In the first part, the objective was to provide further evidence that interaction of Lzm-S with the cardiac membrane glycoprotein was an essential mechanism through which the enzyme mediated myocardial depression. Since the sugar moiety to which Lzm-S would attach would be removed in the deglycosylated muscle, less reduction in depressant activity would be observed when Lzm-S was added to such a preparation. Deglycosylation of the N-linked oligosaccharides from cardiac membrane glycoproteins was performed under native conditions with a Native Protein Deglycosylation Kit (Product Code N-Degly, Sigma Corporation Canada, Oakville, Ontario). The endoglycosidase used was Endo-β-N-acetylglucosaminidase $F_1$ (Endo $F_1$ from *Chryseobacterium meninosepticum*). Endo $F_1$ cleaves between the two N-acetylglucosamine residues in the diacetylchitobiose core of the oligosaccharide, generating a truncated sugar molecule with one N-acetylglucosamine residue remaining on the asparagines (36). The ventricular trabeculae were incubated in the enzyme for 2 h. The effect of Lzm-S at a range of concentrations between $10^{-9}$M to $10^{-5}$M was compared between deglycosylated and nonglycosylated groups of ventricular trabeculae in which the different concentrations of Lzm-S used were added to the organ bath at 5 minute intervals. The concentration of Lzm-S previously found in septic plasma was $10^{-8}$M which was approximately in middle of the range used in the deglycosylation experiments 49). The Lzm-S used in these experiments was purified from the spleens of nonseptic dogs as previously described (49,14).

The second objective of the in vitro study was to determine whether saccharides that were structurally related to TAC could also inhibit Lzm-S's myocardial depressant activity in the in vitro preparation. Inhibitory activities of N-acetylglucosamine (NAG), N,N' diacetylglucosamine (NAG-NAG: N,N' diacetylchitobiose), and N,N',N",N"' tetraacetylglucosamine (NAG-NAG-NAG-NAG: N,N',N",N"'-tetraacetylchitotetraose) were examined (Sigma Corp Canada, Oakville Ontario). These are structurally similar to TAC, but have a different number of NAG units (17). Two somewhat related sugars were also examined to see if there was potential for blocking the activity of lysozyme. These included D-cellotriose and N-aceytllactosamine. D-cellotriose includes three glucose residues linked by beta (1-4) glycosidic linkages, while N acetyllactosamine includes N-acetylglucosamine and galactose residues linked by beta (1-4) glycosidic linkages (12).

After baseline tension was determined, either the sugar or placebo was placed into respective organ baths. The concentration of the sugar used was $10^{-3}$M based on the inventors' previous experiments with TAC 49), while the concentrations of lysozyme were $10^{-9}$, $10^{-8}$, and $10^{-7}$M, respectively. Measurements were obtained at 5 minute intervals. The changes in isometric tension measured from baseline were compared between the treated and placebo baths.

Statistics

Statistical analyses included one and two way—analysis of variance for repeated measures and Student Neuman Keuls' multiple comparison test. Results are reported as mean±1SE.

Results

In vivo Studies

Baseline variables between the treatment and nontreatment groups were not different in any of the three studies. The major hemodynamic results obtained in the Pretreatment Study are shown in FIG. 9. In the placebo treated group, MAP (left upper panel) decreased over 5 hours of sepsis as compared with baseline. In the treatment group, TAC had no effect on baseline MAP, while it significantly prevented the decrease in MAP observed at the 5 hour period in the nontreated group.

The changes in CO, SV, and SW observed in the treatment and nontreatment groups are also shown in FIG. 9 (see left lower panel and right upper and lower panels, respectively). In the treatment group, pretreatment with TAC had no significant effect on CO, but on the mean CO increased slightly as compared with baseline, and this increase was associated with a slight accompanying increase in Pwp in some dogs (see Table 1; note that it was decided not to remove fluid in this condition to achieve Pwp identical to that at baseline because this change in Pwp was relatively small and transient). A similar increase in Pwp with a lesser increase in CO was observed with placebo administration in the nontreatment group, so that the results were not different between the two groups (see Table 1 and FIG. 9). In the treatment group, as compared with baseline, CO increased further at the 3 h period, while it remained unchanged in the nontreatment group. The change in CO observed between baseline and 3 h was significantly different between the two groups. The changes in SV and SW observed between baseline and 5 h were also significantly different between the treated and nontreated groups.

The results obtained in Pwp, HR, Hct, arterial pH and SVR over the course of the study were not different between the two groups and are shown in Table 1. PH declined over time in both groups due to the development of a metabolic acidosis that was non lactate in nature. The amount of normal saline administered was highly variable among the individual animals, but was not significantly different between the two groups (2.0±1 L in the treated vs 1.3±0.34 L in the nontreated group). Blood cultures were positive for *E. coli* in all experiments in both the treatment and nontreatment groups.

In ETS, TAC was infused after 1.5 h of sepsis (see FIG. 8), and the major hemodynamic results are shown in FIG. 10. In the treatment group, MAP (left hand upper panel) increased in 4 of the 5 dogs over the 6 hrs of sepsis, while it decreased in 4 of the 5 dogs in the nontreatment group; however, the results were not different between the two groups. In the treatment group, CO (left lower panel) increased over the course of sepsis as compared with the nontreated group, while SV (right upper hand panel) showed a similar finding. In the nontreatment group, SW (right lower hand panel) decreased approximately by 50% as compared with baseline, while it remained unchanged in the treatment group. The changes in SW were significantly different between the two groups. The results obtained in Pwp, HR, Hct, lactate, arterial pH, and SVR over the course of the study were not different between the two groups and are shown in Table 2. The amount of normal saline infused was also not different in the treated (2±0.7 L) and nontreated groups (1.3±0.5 L).

In LTS, TAC was administered after 3.5 h of sepsis. The major hemodynamic findings are shown in FIG. 11. Once myocardial depression was observed, there was little effect of treatment on SW in this model. Although SW increased on the mean after TAC was administered, this increase was relatively small as compared to the decline in SW observed between the baseline and 3.5 h interval. This increase was also not different from that found in the nontreatment group. The results obtained in Pwp, HR, Hct, lactate, arterial pH, and SVR (see Table 3), and the amount of normal saline solution administered were also not different between the two groups (3.6±1 L in the treated vs 4.3±1 L in the nontreated groups).

In vitro Studies

In the in vitro preparation, lysozyme decreased isometric tension at all of the concentrations studied, while there was little change in the time control group (FIG. 12; left upper panel). The effect of Lzm-S on deglycosylated trabeculae is shown in the left lower panel. Depression observed in the deglycosylated muscle was less as compared with the native preparation when Lzm-S was added to the preparation. Other experiments were performed to test whether sugars that were related to TAC or had slight variations in structure would prevent the depressant effect of Lzm-S on the myocardium. There was no inhibitory effect of tetraacetylchitotetraose (right upper panel) on the decline in isometric tension caused by Lzm-S in the in-vitro preparation. However, in a manner similar to that described for TAC (49), diacetylchitobiose inhibited the depressant effect of Lzm-S (see FIG. 12 right lower).

In other experiments, neither N-acetylglucosamine (NAG), N-acetyllactosamine nor cellotriose had inhibitory properties on lysozyme's myocardial depressant effects in the in vitro preparation. At Lzm-S concentrations of $10^{-9}$, $10^{-8}$, and $10^{-7}$M, isometric tensions decreased to 85±2%*, 61±4.5*%, and 44±2*% of baseline following pre-treatment with N-acetylglucosamine; (n=4); decreased to 60±0%*, 55±1*%, and 48±1*% of baseline, following pre-treatment with N-acetyllactosamine (n=2); and decreased to 84±9%*, 79±13%*, 58±17%* of baseline, respectively following pre-treatment with cellotriose (n=3) (*P<0.05 vs baseline). Because these values were so close to those found in the nontreated groups, only a few experiments were performed in each set of experiments.

Discussion

In Example 1, the inventors identified Lzm-S as a cause of myocardial depression in *E. coli* sepsis and showed that TAC, a competitive inhibitor of this enzyme, blocked the myocardial depression caused by Lzm-S in the right ventricular trabecular preparation. However, the relevance of the latter findings that were performed in a tightly controlled setting to the entity of sepsis remained to be determined. In this example, the inventors extended these findings and showed that in an in vivo model, TAC prevented the development of myocardial depression as well.

In the Pretreatment Study, the inventors gave the drug before *E. coli* was infused and found that the reduction in SW usually observed at the 5 h interval was prevented as compared with the nontreated septic group. In ETS, the inventors administered TAC in the middle of sepsis, before myocardial depression is found in this model, and the results again showed that TAC prevented the reduction in stroke-work as compared with the nontreated sepsis group. In LTS, although there appeared to be a limited response to treatment in some experiments, this increase was relatively small and SW remained quite reduced as compared with the pre-sepsis measurement.

Thus, TAC was able to prevent the development of myocardial depression in sepsis even when bacteremia was ongoing as in ETS, while not in LTS when myocardial depression had already developed. In a model of *Pseudomonas aeruginosa* bacteremia and pneumonia in dogs (35), the inventors previously used continuous arterial venous hemofiltration (CAVH) to remove myocardial depressant activity from the circulation. The inventors found that early use of CAVH was associated with a greater degree of preserved myocardial function as compared to when CAVH was administered after myocardial depression had already developed.

Nevertheless, there may be some evidence to suggest that TAC may reverse myocardial depression even when administered after depression had already developed. In a previous study, the inventors were able to show that in ventricular trabeculae subjected to 4 h of bacteremia, there was a gradual improvement of isometric tension when the trabeculae were continuously washed over a period of 1 h (7). In LTS, the dose of TAC may have been too small to reverse myocardial depression and therefore a higher dose of treatment may have been able to competitively remove Lzm-S from the cardiac membrane. Alternatively, hydrolysis of the membrane glycoprotein by Lzm-S may have irreversibly injured the muscle making it unsusceptible to inhibition by TAC (see below).

The mechanism of action of Lzm-S in causing cardiac depression is a very intriguing question. In the in vitro preparation, the decline in myocardial tension observed with Lzm-S occurs within 5 minutes, and thus its mechanism of action would favor a direct effect on the myocardium (6,28). In the heart, most membrane proteins are posttranslationally modified, are heavily N-glycosylated, and therefore are glycoproteins (51,29,30,21). Others have found that changes in N-glycosylation may alter the function of L-type calcium channels, regulation of potassium channels, and activation of sodium channels (29,30,21). The inventors consider two possibilities about how Lzm-S may affect membrane function by acting on a glycoprotein. In one mechanism, Lzm-S binds to an extracellular saccharide-bearing structure and hydrolyses the bond between two monosaccharide units, such that this hydrolysis causes the biological effect of a decrease in myocardial contraction. Alternatively, Lzm-S binds to an extracellularly orientated saccharide bearing structure, is unable to hydrolyse it, but because of its binding induces a conformation change of the carbohydrate tree and the glycoprotein bearing it. This conformational change causes the biological effect of a depression in myocardial function. For Lzm-S to cause hydrolysis, the presence of a vicinal NAG-NAM structure is required, while for binding alone, a structure containing NAG-NAG should be sufficient. Binding of Lzm-S to the surface membrane could be overcome by an inhibitor, such as TAC, while a cleaved bond would not be restored by this treatment. This is one explanation about why myocardial function was not reversible once depression had already occurred in LTS. The precise mechanism by which Lzm-S causes myocardial depression once bound to the surface membrane needs to be addressed in future studies.

To provide further evidence that the carbohydrate portion of the glycoprotein was the mechanism through which Lzm-S may cause myocardial depression in sepsis, the inventors performed deglycosylation experiments in which the N-linked oligosaccharides from glycoproteins on the cardiac membrane were cleaved. The reduction in isometric tension caused by Lzm-S in the deglycosylated muscle was much less than that found in the native muscle. The inventors also tested numerous possible inhibitors in order to learn something about the specificity of Lzm-S in causing myocardial depression (17). Of the inhibitors tried, only TAC and N,N'-diacetylchitobiose showed a beneficial effect, these results pointing to the specificity of the inhibitor in preventing Lzm-S's depressant activity on the myocardium.

Plasma lysozyme is believed to stem mainly from disintegrating neutrophilic granulocytes and monocytes (25,53,27). In an earlier study, Burgess et al. (52) used elevations in serum Lzm-S as a marker to diagnose the development of an occult intra-abdominal abscess in critically ill patients following trauma. Lysozyme activity was found to increase in septic patients with intra-abdominal abscess, although hemodynamic measurements were not obtained. More information is needed to assess the concentrations that are reached in septic shock in the clinical setting and to relate these concentrations to the changes in cardiovascular performance observed.

The inventors also used SW as their primary index of myocardial performance and the limitations of this measurement need to be considered. SW is dependent on left ventricular (LV) preload, afterload, and contractility. The inventors maintained Pwp (their index of preload) relatively constant over the course of the study. At the beginning of the study, there were only slight differences in Pwp between the groups in the respective studies, and no changes in Pwp were found between the baseline and post-sepsis measurements in any of the groups studied. The inventors therefore do not believe that these small differences in Pwp accounted for the findings observed. On the other hand, it is possible that TAC may have affected LV diastolic function, so that diastolic volume was increased for a given Pwp. In a previous study, the inventors showed that diastolic pressure-volume relations remained unchanged over the course of sepsis in this model, while LV systolic performance progressively decreased (6). The inventors therefore favor the notion that TAC improved SW study by means of an improvement in contractility. Nevertheless, it is possible that TAC altered LV diastolic filling in the present study. This possibility will need to be addressed in future experiments.

Changes in LV afterload may also affect SW. The inventors measured SVR over the course of the study, and although this parameter is a derived index and may not be totally representative of afterload (52), SVR was not different between comparable groups. Variations in Hct may alter afterload through its affect on viscosity, since Hct decreased over the course of the study. However, decreases occurred to a similar extent in comparable groups, and most likely developed because of the infusion of normal saline to replace the large amounts of diarrhea that ensured over the course of the study. The volume infused was highly variable among the dogs, but was not different in the treatment and nontreatment groups in the respective studies. Moreover, this infusion mostly likely accounted for the metabolic acidosis that developed over the course of study that was non lactate in nature.

Despite its limitations, the inventors used SW as the measurement of myocardial performance because it incorporates meaningful clinical parameters of hemodynamics, namely MAP and SV. These parameters are widely used to monitor patients in the intensive care unit. In previous sepsis studies, the inventors used volumetric indices to evaluate cardiac contractility in this model, such as the slope of the end-systolic pressure volume relationship (6) and the slope of the preload recruitable relationship (18). However, these indices have limited practical utility in the care of patients in the intensive care unit, since the physician wants to know if a treatment improved MAP and CO or SV. Additional studies will need to be performed to further evaluate the effect of TAC on other indices of cardiac contractility in sepsis.

In addition, although the preparation was identical in the three studies, mean baseline HR varied slightly among the different groups, but no significant differences were observed. The range of HR in the individual dogs was quite large and varied between 45 and 120. The inventors are of the view that the variability in HR observed among the groups was related to the small number of animals studied. Moreover, in the design of the in vivo studies, the inventors did not use nonseptic treated and nontreated control groups in the experimental protocols, since when TAC was administered in the nonseptic condition in the Pretreatment Study, other than to observe a slight increase in Pwp related to the added volume, there was little change in the hemodynamic results noted. Since TAC did not produce changes in isometric tension when added alone in the in vitro preparation (49), the inventors thought that there was little rationale for the inclusion of treated and nontreated nonseptic control groups in the present study.

It is also noteworthy that the inventors previously showed that Lzm-S inhibited the β-adrenergic response to both neural stimulation and isoproterenol in the in vitro preparation, and that this inhibitory effect could be blocked by TAC. The β-adrenergic receptor is a heavily glycosylated protein (51), and the extent to which TAC enhanced the adrenergic response in the present study also needs to be considered in the interpretation of the results. On the other hand, the lack of an effect of TAC on SVR is consistent with the findings reported in the inventors' previous studies that showed that CAVH also did not affect SVR (6,35). Accordingly, the inventors do not believe that the vasodilation found in sepsis can be attributable to the effect of lysozyme. Whether TAC is beneficial to the functioning of other organs is not clear at this time.

In summary, the present study showed that TAC prevented the development of myocardial depression in an in vivo preparation. However, once myocardial depression had already occurred, there was little reversal of this depression. Further experiments will be required to assess whether TAC may be useful once myocardial depression has already developed. In the present study, the inventors also showed that in addition to TAC, Lzm-S is strongly inhibited by N,N'-diacetylchitobiose, but not to other related oligosaccharides. This finding is consistent with studies of structure and function where the inhibitors for this enzyme were found to be quite specific (16,17). It is also important to note that this study does not exclude other mechanisms that have previously been proposed to cause myocardial depression in sepsis (20,22). Whereas it is recognized that the relevance of animal models to the human condition must be interpreted cautiously, the results suggest that inhibition of Lzm-S by TAC or N,N'-diacetylchitobiose may be useful in the treatment of cardiovascular collapse in sepsis.

Example 3

Specific Lectins Mimic the Myocardial Dysfunction Caused by Lysozyme in Canin v Ntricl In the present Example, the inventors hypothesized that lectins with a carbohydrate specificity similar to that described for lysozyme with primary affinity for oligomers of N-acetylglucosamine (NAG-NAG-NAG structure) (eg *Datura stramonium* lectin and *Lycopersicon esculentum* lectin) would cause myocardial depression in a right ventricular trabecular preparation (RVT). The inventors compared the latter lectins with those with affinities to variants to the NAG-NAG-NAG structure, that included affinities for the chitobiose structure (NAG-NAG: *Triticum vulgaris* lectin), for the N-acetyllactosamine structure (*Erythrina corallodendron* lectin), and for terminal N-acetyl galactosaminyl residues (*Helix pomatia* lectin). The results showed that lectins with an affinity for the NAG-NAG-NAG structure demonstrated a depression in isometric tensions similar to that described for lysozyme which was significantly greater than that found for the other lectins. The inventors conclude that binding to rather than hydrolysis of the carbohydrate tree on the cardiac membrane is all that is required for lysozyme to cause myocardial depression. Lectins that bind with a specificity of lysozyme also show comparable depression. These data provide further evidence that the release of mediators, such as lysozyme, that bind to cardiac membrane glycoproteins may lead to myocardial dysfunction in sepsis.

Methods

These experiments were approved by the University Animal Care Committee and conform with the Guide for the Care and Use of Laboratory Animals published by the US National Institutes of Health (NIH Publication No 85-23,1996).

The right ventricular (RV) preparation used in this study has also been described. Briefly, mongrel dogs (3 to 10 kg) were anesthetized with pentobarbital. The hearts were removed, flushed with 50 ml of Krebs-Henseleit solution (KH), and placed in ice-cold KH bubbled with a mixture of 95% $O_2$ and 5% $CO_2$. Three to four thin trabeculae (<1 mm diameter) were obtained from the right ventricle and were tied at each end with 6-O silk thread. Each thin muscle was suspended in a vertical constant temperature bath (5 ml) that contained KH (in mM: NaCL, 118; KCl, 4.7; $CaCl_2$ 2.5; $MgSO_4$, 1.2; $KH_2PO_4$, 1.4; $NaHCO_3$, 25; and dextrose, 11). The muscle was stimulated electrically via punctate platinum bipolar electrodes with rectangular pulses (1 ms duration) at an intensity of 50% above threshold delivered at intervals of 2,000 ms. The trabeculae were stretched to optimal length.

The lectins chosen were based on their specificity for binding to carbohydrate structures similar to those to which lysozyme would bind as well to slight variants in the NAG structure. The latter would indicate whether binding to specific carbohydrate structures affected the degree of myocardial depression that occurs in the in vitro preparation. *Lycopersicon esculentum* lectin (MW 71 K) has an affinity for NAG oligomers and is a glyocprotein that contains approximately equal amounts of protein and carbohydrate (37). *Datura stramonium* lectin (MW: 86K) has affinity for oligomers of N-acetylglucosamine and N-acetyllactosamine (38). This lectin is a glycoprotein that contains approximately 35% carbohydrate. *Triticum vulgaris* lectin (MW: 36K) has an affinity for N-acetyl-glucosamine residues and N-acetyl-glucosamine oligomers (39). This lectin contains no protein bound carbohydrate. *Erythrina corallodendron* lectin (MW: 60 K) has an affinity for N-acetyllactosamine, N acetyl-galactosamine, lactose, and D-galactose (40). *Helix pomatia* lectin (MW: 79K) has affinity for terminal N-acetyl galasoaminyl residues (41).

After baseline tension was determined, either the lectin or placebo was placed into respective organ baths. The concentrations of the lectins used were $10^{-8}M$, $10^{-7}M$, and $10^{-6}M$ based on the concentration of lysozyme found in sepsis that averaged approximately $10^{-8}M$. In the case of *Datura stramonium* lectin, moreover, the effect of TAC on inhibiting the myocardial depression caused by this lectin was also examined. TAC was found to be an inhibitor of lysozyme in the in vitro preparation in previous experiments, and since *Datura stramonium* lectin has similar affinity for the NAG-NAG-NAG structure as does lysozyme, it was determined whether TAC ($10^{-4}M$) blocked the depressant activity of this lectin in the in vitro preparation. Measurements were obtained at 5 minute intervals. The changes in isometric tension measured from baseline were compared between the lectin treated and placebo preparations.

Statistics

Statistical analyses included two way analysis of variance and Student Neuman Keuls' multiple comparison test.

Results

The results obtained with *Datura stramonium* are shown in FIG. 13 (upper panel). *Datura stramonium* lectin caused a dose response reduction in myocardial tension. At a lectin concentration of $10^{-6}M$, isometric tension decreased to approximately 35% of baseline. There were no changes in isometric tension observed in the time control group over this interval. In FIG. 13 (lower panel) the preparation was treated with either TAC or KH in respective organ baths. The degree of myocardial depression caused by *Datura stramonium* in the TAC treated preparation was markedly attenuated as compared with the placebo preparation.

In FIG. 14 (upper panel), the results obtained with *Lycopersicon esculentum* lectin are shown. At a lectin concentration of $10^{-6}M$, *Lycopersicon esculentum* again reduced isometric tension to approximately 35% of baseline, while there were no changes in isometric tension found in the time control group over this interval. In FIG. 14 (lower panel), *Triticum vulgaris* lectin caused much less reduction in isometric tension as compared with either *Datura stramonium* lectin or *Lycopersicon esculentum* lectin. At a lectin concentration of $10^{-6}M$, *Triticum vulgaris* lectin reduced isometric tension to 70% of baseline, while there were no changes observed in the time control group.

In FIG. 15, the results obtained with *Erythrina corrallodendron* lectin and *Helix pomatia* lectin are shown. Although some decline in isometric tension was observed with these lectins, these reductions were small as compared with *Datura stramonium* lectin and *Lycopersicon esculentum* lectin. At lectin concentrations of $10^{-6}M$, the reductions observed with *Erythrina corallodendron* and *Helix pomatia* lectin were to approximately 75% of baseline, which were just slightly greater than the results obtained in the time control group.

Discussion

There were two reasons for performing this study. On the one hand, the inventors wanted to determine if the mechanism by which lysozyme causes myocardial depression in sepsis is related to the binding of the enzyme to the carbohydrate portion of cardiac membrane or whether hydrolysis of the bond between two monosaccharide units is an important requirement. For lysozyme to cause hydrolysis, the presence of a vincinal NAG-NAM structure on the cardiac membrane would be necessary, while for binding alone, a structure that contained NAG-NAG or NAG-NAG-NAG units would be sufficient. Lectins are carbohydrate binding proteins that display no enzymatic activity (42). *Datura stramonium* lectin and *Lycopersicon esculentum* lectin (see FIGS. 13 and 14, respectively) have predominant affinity for the NAG-NAG-NAG structure and resulted in marked decreases in isometric tension in the in vitro preparation. According, these findings would support the notion that binding alone is all that is required for lysozyme to cause myocardial depression in sepsis.

The second reason for performing this study was to determine the degree to which lectins with different carbohydrate binding specificities would cause myocardial dysfunction in the right ventricular trabecular preparation. The inventors looked at lectins with specificities to oligomers of NAG (NAG-NAG-NAG), residues of NAG (NAG-NAG), and to variants of the NAG structure (ie N-acetyllactosamine and terminal N-acetyl galactosaminyl residues) and determined the extent to which each compound would reduce isometric tension in the in vitro preparation. The results showed that lectins with a primary affinity for the NAG-NAG-NAG structure (e.g. *Lycopersicon esculentum* lectin and *Datura stramonium* lectin) (37,38) caused a much greater reduction in isometric tension than that caused by the lectin whose primary affinity was to the NAG-NAG residue (eg *Tricticum vulgaris* lectin) (39). Furthermore, there was only a minimal reduction in isometric reduction caused by the lectins with specificities to the variants to the NAG structure, such as *Erythrina corallodendron* lectin and *Helix pomatia* lectin.

In the previous Examples, the inventors examined the effect of lysozyme on isometric tension in the right ventricular trabecular preparation and found that at a concentration of $10^{-6}$ M, the reduction in isometric observed was to approximately 30% of baseline. This degree of depression is very similar to that found with either *Datura stramonium* lectin and *Lycopersicon esculentum* lectin in the present study. Since, on a molar bases, all three compounds—*Datura stramonium* lectin, *Lycopersicon esculentum* lectin, and lysozyme—produced similar degrees of depression, one could argue that they all preferentially targeted the NAG-NAG-NAG structure on the cardiac membrane to the same extent. Although it is felt that this is the case, the inventors recognize the need to be cautious about this interpretation. Individual lectins have peculiar tendencies that affect their binding to various carbohydrate structures and these cannot readily be discerned by their structure; for instance *Datura stramonium* lectin may target the NAG-NAG structure and N-acetyllactosamines, while *Tricticum vulgaris* lectin may also have specificity to N-acetylneuraminic acid. Such differences may complicate comparisons among the various lectins. Nevertheless, from the standpoint of the present study, it appears that myocardial depression in the in vitro preparation can best be explained by compounds, such as lysozyme, *Lycopersicon esculentum* lectin and *Datura stramonium* lectin that favor the NAG-NAG-NAG structure on the cardiac membrane.

Although many of the cardiac membrane proteins are glycosylated, we are still unclear about how changes in glycosylation may alter function in the myocardium. Others have found that changes in N-glycosylation may alter the function of L-type calcium channels, regulation of potassium channels, and activation of sodium channels (28-30). Changes in the function of these channels may lead to myocardial depression in sepsis. The inventors hypothesize that binding by lysozyme causes a functional change in the properties of a membrane glycoprotein with an extracellularly orientated carbohydrate tree thereby interfering with myocardial excitation contraction coupling in sepsis.

It therefore seems reasonable to assume that the binding by lectins would result in a similar functional change in the cardiac membrane glycoprotein. The structures of *Datura stramonium* lectin and *Lycospersicon esculentum* lectin are quite distinct (37,38), and the only common denominator between them is that they target the NAG-NAG-NAG structure on the cardiac membrane. Although the physiological functions of many lectins are not clear, these range from affecting cell-cell interactions, intracellular-routing of glycoproteins and vesicles, cellular mitosis, among others (42). However, it is unlikely that any such mechanisms would be applicable to the results reported in the present study, since the aforementioned mechanisms would require a relatively long time frame to occur. In the present study, the decline in myocardial tension observed in the in vitro preparation when the lectins were instilled occurred within 5 minutes, and thus their mechanism of action (like lysozyme) would favor a direct effect on the cardiac membrane glycoprotein. Future experiments are required to discern the specific physiological changes that occur related to this binding.

The inventors previously showed that in *E. coli* sepsis, lysozyme increased in plasma over the course of bacteremia and the concentrations reached are significantly high enough to produce myocardial depression in the right ventricular trabecular preparation. The inventors further found that this depression could be blocked by TAC in in vitro and in vivo preparations (Examples 1 and 2). The present study extends these findings. It shows that lectins that bind to the carbohydrate portion of cardiac membrane with a specificity of lysozyme may also cause comparable myocardial depression. Taken together, these data provide further evidence that during the inflammatory response, the release of mediators, such as lysozyme, by binding to an extracellularlly orientated saccharide bearing structure, induces a conformation change of the carbohydrate tree and the glycoprotein bearing it, that in turn leads to myocardial dysfunction in sepsis.

Example 4

Characterization of Surface Membrane N-glycan Binding Sites of Lysozyme for Myocardial Depression in Sepsis The inventors hypothesized that lysozyme binds to or cleaves a cardiac surface membrane N-glycoprotein thereby interfering with myocardial contraction in sepsis. The primary objectives of the present Example were to determine whether the binding of lysozyme to the N-glycan structure was reversible and to assess the part of the N-glycan structure to which lysozyme binds.

Methods

These experiments were approved by the University Animal Care Committee and conform with the Guide for the Care and Use of Laboratory Animals published by the US National Institutes of Health (NIH Publication No 85-23, 1996) (10).

The RVT preparation used in this study has previously been described (43,44). Briefly, mongrel dogs (3 to 10 kg) were anesthetized with pentobarbital. The hearts were removed, flushed with 50 ml of Krebs-Henseleit solution (KH), and placed in ice-cold KH bubbled with a mixture of 95% $O_2$ and 5% $CO_2$. Three to four thin trabeculae (<1 mm diameter) were obtained from the right ventricle and were tied at each end with 6-O silk thread. Each thin muscle was suspended in a 5 ml vertical constant temperature bath that contained KH. The muscle was stimulated electrically via punctate platinum bipolar electrodes with rectangular pulses (1 ms duration) at an intensity of 50% above threshold delivered at intervals of 2,000 ms. The trabeculae were stretched to optimal length.

The plasma concentration of Lzm-S attained in the inventors' sepsis model is approximately $10^{-8}$M (43), and the $10^{-7}$M to $10^{-9}$M range was used in the experiments described below. Lzm-S was purified from the spleens of nonseptic dogs as previously described (43). Furthermore, when Lzm-S, lectin, or KH (see below) was added to the RVT preparation, measurements were determined at 5 min intervals unless otherwise indicated.

Reversibility Experiments

Reversibility of Lzm-S's myocardial depressant effect in the RVT preparation was assessed by repeatedly washing the muscle with KH and by the repeated additions of either N,N'-diacetylchitobiose (chitobiose) or N,N',N''-triacetylchitotriose (TAC or chitotriose) (43,44). Chitobiose and TAC are competitive inhibitors of Lzm-S and consist of GlcNAcβ1-4GlcNAc, and GlcNAcβ1-4GlcNAcβ1-4GlcNAc structures, respectively. When given before Lzm-S instillation, these treatments have previously been shown to competitively inhibit Lzm-S's depressant activity in in vitro and in vivo studies (43,44).

Seven groups of trabeculae were examined in the reversibility study. In 4 of the 7 groups examined, after baseline measurements were obtained, $10^{-7}$M Lzm-S was added to the RVT preparation and determination of isometric tension was repeated 5 min later (treatment condition). Repeat measurements were then performed for three consecutive intervals at 15 min apart in which different interventions were performed among the groups; in group 1, no further intervention was performed; in group 2 the trabeculae were repeatedly washed with KH at the beginning of each 15 min interval; in group 3, $10^{-3}$M chitobiose was repeatedly added to the preparation at the beginning of each interval; in group 4, $10^{-3}$M TAC was repeatedly added at each interval. The remaining three groups were control groups in which KH rather than Lzm-S was added to the preparation in the treatment condition: in group 5, repeated washes at 15 intervals apart were examined; in groups 6 and 7, chitobiose ($10^{-3}$M) and TAC ($10^{-3}$M), respectively, were added at 15 min intervals.

Assessment of N-glycan Structure to Which Lzm-S Binds

Regardless of the type of carbohydrate structure to which Lzm-S may bind, it is possible to deglycosylate the carbohydrate structure by means of exoglycosidases in which a specific sugar residue is removed from the terminal end of the carbohydrate tree (47). The extent to which removal of a residue is associated with a reduction in the depressant effect of Lzm-S can be used to ascertain the functional importance of a sugar residue. The initial hypothesis was that Lzm-S binds to the chitobiose structure (i.e GlcNAcβ1-4GlcNAc residues) of the tri-mannosyl core (see FIG. 16). In the exoglycosidase experiments, six groups of trabeculae were studied. In group 1, no treatment was administered and the effect of Lzm-S was examined at $10^{-9}$M, $10^{-8}$M, and $10^{-7}$M concentrations. In group 2, the trabeculae were initially bathed in sialidase (60 μl; 5 U/ml) for two hours to remove any N-acetylneuramic acid (NeuNAc) residues, after which the effect of Lzm-S was determined (all kits from Prozyme, San Leandro, Calif.; kit GE 23; Sialidase A). In group 3, the trabeculae were bathed with sialidase and β-galactosidase (60 μl; 3 U/ml) to remove possible NeuNAc and galactose (Gal) residues, after which the effect of Lzm-S was examined (Kit GE 12; β-galactosidase). In group 4, the effect of Lzm-S was examined after the trabeculae were incubated with sialidase, galactosidase, and β-glucosaminidase (60 μl; 45 U/ml) to remove the NeuNAc, Gal, and GlcNAc residues (Kit 31: β-glucosaminidase), respectively. In group 5, the trabeculae were bathed with the three previous enzymes as well as enzymes to remove all of the mannose residues [(Kit GE 60; α(1-6) core mannosidase (60 μl; 1 U/ml); Kit 62; α(1-3,4 mannosidase (60 μl; 11 U/ml); Kit Glyco X-5015: β1-4 mannosidase) (60 μl; 1 U/200 μl)] and most possible fucose attachments [Kit 70; α1-3,4 fucosidase (60 μl; 0.5 U/ml) and Kit 73; α(1-2) fucosidase (60 μl; 100 mU/ml)].

As described in the results, the depressant activity of Lzm-S was completely lost in group 5, even though the hypothesized structure to which Lzm-S would bind (i.e. the GlcNAcβ1-4GlcNAc moiety) was not removed from the membrane. Based on the analysis of the structures degraded, it was hypothesized that the important structure removed in group 5 was the mannose residue attached by the β1-4 linkage to the GlcNAcβ1-4GlcNAc structure (see bolded structures in FIG. 16). In group 6, the exact same protocol was performed as that described in group 5, except that the β(1-4) mannosidase enzyme that cleaved the Manβ1-4 linkage was not included in the enzyme mix.

In other experiments, endo-β-N-acetylglucosaminidases were used to define the type of carbohydrate structure to which lysozyme binds. Endo-β-N-acetylglucosaminidases cleave the linkage between the two GlcNAcβ1-4GlcNAc residues in the chitobiose core (48) (see bold "F" in FIG. 16). *Flavobacterium meningosepticum* secretes three endo-β-N-acetylglucosaminidases, termed endo $F_1$, endo $F_2$, and endo $F_3$ that have specificities for distinct oligosaccharide structures. Endo $F_1$ cleaves only high-mannose and hybrid oligosaccharides. Endo $F_2$ preferentially processes bi- antennary complex oligosaccharides. Endo $F_3$ is specific for bi- and tri-antennary complex oligosaccharides. In respective groups, the ventricular trabeculae were treated with either endo $F_1$(0.3 unit), endo $F_2$(0.1 unit), and endo $F_3$(0.1 unit) for 2 hours (as per Native Protein De-glycosylation Kit; Product Code N-Degly, Sigma Corporation Canada, Oakville, Ontario). The enzyme was washed off of the muscle with KH. The effect of Lzm-S was compared between the endo F treated and nontreated groups in the organ bath. In separate control experiments, the effect of KH rather than that of Lzm-S was examined over a similar interval between endo F treated and nontreated groups.

Lectin Experiments

Lectins are nonenzymatic proteins that bind to carbohydrates and can be classified by their specificity for a particular sugar or polysaccharide (42). *Lycopersicon esculentum* lectin (LEL) and *Datura stramonium* lectin (DSL) have affinity for the GlcNAcβ1-4GlcNAcβ1-4GlcNAc (i.e. the TAC structure) (37,38) similar to that described for Lzm-S; on the other hand, *Triticum vulgaris* lectin (TVL) (39) has a predominant affinity for the GlcNAc β1-4GlcNAc moiety (ie. the chitobiose structure) (39), while *Erythrina corallodendron* lectin (ECL) (40) and *Helix pomatia* lectin (HPL) have affinity for totally unrelated structures that include for the former N-acetyllactosamine, N acetyl-galactosamine, lactose, and D-galactose (40) and for the latter N-acetyl galactosaminyl residues (41). After baseline tension was determined, either the lectin or placebo (i.e. KH) was placed into respective organ baths in which the concentrations of the lectins used were similar to those described for Lzm-S. In the case of DSL, moreover, it was assessed whether TAC could also prevent the depression caused by this lectin.

To Examine Whether the Carbohydrate Portion of the Membrane Glycoprotein to Which Lysozyme Binds is Affected in the Single Myocyte Preparation The effects of Lzm-S and *Lycopersicon esculentum* lectin (LEL) on excitation-contraction coupling were examined in guinea pig myocytes as previously described by Louch et al (46). Guinea pig myocytes were used in these studies because it was difficult to procure canine myocytes in the collaborating laboratory where the myocyte studies were performed. In the myocyte preparation, the guinea pig heart was perfused with calcium free solution that contained (in mM); 120 NaCl, 3.8 KCl, 1.2 $KH_2PO_4$, 1.2 $MgSO_4$, 10 HEPES, and 11 glucose (pH 7.4 with NaOH). The heart was treated with collagenase A (25 mg/50 ml buffer, Boehringer-Mannheim) and protease type XIV (4.8 mg/50 ml buffer, Sigma Corp) for 5 minutes. The ventricle was then minced in a buffer with the following composition (in mM): 80 KOH, 50 glutamic acid, 30 KCL, 30 $KH_2PO_4$, 20 taurine, 10 HEPES, 10 glucose, 3 $MgSO_4$, and 0.5 EGTA (pH 7.4 with KOH).

Cells were voltage clamped with high resistance electrodes (18-25) and held at −80 mV (Axoclamp 2B amplifier, Axon Instruments). Currents were recorded during test steps from −55 to 0 mV with discontinuous single electrode voltage-clamp (sample rate 7-8 kHz). Test steps were preceded by trains of conditioning pulses to ensure consistent calcium loading of the sarcoplasmic reticulum. Contractions were recorded as unloaded cell shortening with a video edge detector (Crescent Electronics) and video camera (model TM-640). Amplitudes of contractions and L-type calcium currents were measured at one minute intervals during superfusion of the cells with buffer alone (time control), buffer plus Lzm-S ($10^{-7}$M), or buffer plus lectin ($10^{-6}$M). Since the data showed that neither Lzm-S nor lectin had any effect on contraction and had little effect on L-type calcium current in guinea pig ventricular myocytes, it was hypothesized that the enzymes and buffers utilized may affect the carbohydrate structure on the membrane. In order to test for this possibility, the effect of Lzm-S on isometric tension was examined in the RVT preparation in which similar buffers and enzymes were used, but the ventricular trabeculae were not minced.

Statistics

Statistical analyses included two way repeated measures analysis of variance (between-within ANOVA) and Student Newman-Keuls' multiple comparison test. In the design of the experiment, a single sample in a given experiment represents a muscle from a single dog. Of the 3 to 4 trabeculae obtained from a dog, each trabecular muscle was used for a different subset of experiments in a specific study. The results are expressed as mean (±1SD).

Results

In FIG. 17, the reversibility experiments are shown for the Lzm-S treated (upper panel) and KH treated (lower panel) groups. In the Lzm-S group in which no intervention was performed, isometric tension measured at the $3^{rd}$ measurement interval decreased to ≈40% of baseline. In the Lzm-S treated group in which the muscle was repeatedly washed with KH solution, isometric tension determined at the $2^{nd}$ and $3^{rd}$ measurement intervals returned to the baseline level. In the Lzm-S treated groups in which chitobiose and TAC were added to respective preparations, the Lzm-S inhibitors attenuated the decrease in isometric tension as compared to when no intervention was instituted, but these treatments did not return isometric tension back to baseline. In control experiments (lower panel), in which KH rather than Lzm-S was added to the preparation, chitobiose and TAC by themselves displayed a modest depressant effect over the interval of the experiment.

FIG. 18 shows the exoglycosidase experiments in which the effect of Lzm-S on isometric tension was determined after terminal sugars of the membrane glycoprotein were sequentially removed. When no treatment was administered, Lzm-S at $10^{-7}$M caused a decrease in isometric tension to approximately 40% of baseline (see group 1). Treatments with sialidase or the combination of a sialidase, galactosidase, and glucosaminidase had no inhibitory effect on the response to Lzm-S (see groups 2,3,4). On the other hand, in group 5, when treatment was performed with all enzymes that included sialidase, galactosidase, glucosaminidase, the three types of mannosidases (α1-3,4); (α1-6); (β1-4)], and the fucosidases, it was found that the myocardial depressant effect of Lzm-S was eliminated. In group 6, when the β1-4 mannosidase was omitted from the enzymes included in group 5, Lzm-S's myocardial depressant effect was restored to that found in groups 1-4.

In FIG. 19 (upper panel), the effect of Lzm-S on ventricular trabeculae treated with endo-$F_1$, endo-$F_2$, and endo-$F_3$ are shown. Endo-$F_1$ and endo-$F_3$ significantly reduced the myocardial depressant effect of Lzm-S as compared with the nontreated Lzm-S group, while endo-$F_2$ did not have any attenuating effect. In control experiments (FIG. 19 lower panel), in which KH rather than Lzm-S was added to the preparation, the endo-F enzymes by themselves displayed some depressant effect over time that occurred to a similar extent among the enzymes tested.

The lectin experiments are shown in FIG. 20. DSL (FIG. 20 left upper panel) which has a primary specificity for the TAC structure (38) caused a decline in isometric tension similar to that found for Lzm-S. Moreover, this decline in isometric tension could be reversed by pre-treatment with TAC (left lower panel). LEL which also has affinity to the TAC structure (37) also produced a marked decrease in isometric tension (FIG. 20 right upper panel). However, TVL which has a specificity to the chitobiose structure (39) and ECL (40) and HPL (41), both of which have specificities for entirely different moieties caused much less a decline in isometric tension as compared with DSL and LEL (right lower panel).

In FIG. 21, the results are shown when myocytes were exposed to Lzm-S. There was no difference in contraction between the treated and non treated cells and no difference in L-type calcium currents between the two groups over the course of the experiment (data not shown). A similar negative effect was observed when the myocytes were treated with LEL (data not shown). In FIG. 21 (lower panel), the results show that when the ventricular trabeculae were treated with protease type XIV and collagenase A in a manner similar to that described for the single myocyte preparation, the effect of Lzm-S on isometric tension was not different as compared to that observed with KH treatment.

Discussion

In this Example, the inventors characterized the N-glycan to which Lzm-S binds to cause myocardial depression in sepsis. Based on the types of carbohydrate structures to which Lzm-S could theoretically bind, it was initially hypothesized that binding of Lzm-S would occur to the GlcNAcβ1-4GlcNAc structure in the region of the tri-mannosyl core (see FIG. 16). However, when all of the sugar residues except for the GlcNAcβ1-4GlcNAc residue were removed by exoglycosidase treatments, all depressant activity of was Lzm-S was eliminated. Thus, the primary hypothesis was incorrect and further examination was required.

Rand-Meir et al (7) reported that the TAC structure (i.e. GlcNAcβ1-4GlcNAcβ1-4GlcNAc) was a better inhibitor of Lzm-S's enzymatic activity than the two unit chitobiose structure (6,7). Furthermore, they showed that Lzm-S cannot only accommodate GlcNAc in its binding, but that the enzyme also binds glucose and deoxyglucose. In deoxyglucose, the oxygen of the number 2 position of glucose is missing. On the other hand, the N-acetyl moiety in GlcNAc is linked via the number 2 carbon atom to the rest of the glucose molecule. The inventors therefore considered that the active site of Lzm-S might be tolerant of changes to the number 2 position of the monosaccharide unit that is accommodated. Glucose and mannose differ only in the orientation of the hydroxyl group at the number 2 position of the molecule, in one sugar the OH-group is above the plane, in the other it is below the plane of the pyranose ring. Thus, the inventors hypothesized that the Man residue linked by β1-4 linkages to the GlcNAcβ1-4GlcNAc in the core structure may be important for the myocardial depressant effect of Lzm-S: When the Manβ1-4GlcNAcβ1-4GlcNAc structure was left intact in group 5, the inventors showed that Lzm's depressant activity was again apparent, the results supporting the conclusion that Lzm-S binds to a variant of the chitotriose structure in the tri-mannosyl core of a membrane glycoprotein.

In other experiments, the inventors used different endo-β-N-acetylglucosaminidases to determine the particular type of carbohydrate structure to which Lzm-S may bind (48). Lzm-S's depressant activity was markedly attenuated by endo-$F_1$, which has specificity for high mannose/hybrid types, and by endo-$F_3$, which has specificity for bi- and tri-antennary complex oligosaccharides. On the other hand, there was little effect for endo-$F_2$ which preferentially processes bi-antennary complex oligosaccharides. Stiles et al (50) examined the carbohydrate subtypes of the mammalian β-adrenergic receptors in hamster lung and rat erythrocytes, and also provided evidence for the existence of both high-mannose and complex type carbohydrate chains on $β_2$-adrenergic receptors. The inventors' results show that Lzm-S binds to similar carbohydrate classes to cause myocardial depression in sepsis.

In terms of the analyses used, the carbohydrate binding properties of Lzm-S were examined by techniques that included endo-β-N-acetylglucosaminidases and exoglycosidases. In the exoglycosidase experiments, the inventors did not find any effect of the enzymes in groups 2 to 4. One could therefore question whether the enzyme concentration and/or incubation period may have been insufficient to cause an effect. Because of the following rationale, it is believed that this is unlikely. The exoglycosidases are quite unique, in that each enzyme degrades only the non-reducing (i.e. terminal) residues of a particular carbohydrate structure. In terms of the endo-β-N-acetylglucosaminidase experiments, it was found that the glycoproteins to which Lzm-S binds are of high mannose/hybrid or tri-antennary complex types. For the condition of the high mannose structure, the addition of the sialidase, β-galactosidase, and β-glucosaminidase would not be expected to have an effect, since NeuNAc, Gal, and adjacent GlcNAc residues are not present on this type of structure.

However, in the case of the complex tri-antennary structure or hybrid structure, some or all of these terminal sugars would be present. Evidence of the effectiveness of sialidase, galactosidase, and glucosaminidase is given by the fact that in order for the mannosidases to have successfully degraded the adjacent mannose units, the terminal NeuNAc, Gal, and adjacent GlcNAc residues must have previously been removed. Otherwise, the elimination of Lzm-S's depressant effect when all of the mannosidases were given in group 5 would not have been observed.

The washing experiments (FIG. 17) and the lectin experiments (FIG. 20) indicate that the myocardial depression caused by Lzm-S is reversible, although it must be remembered that in the design of the experiment longer periods of contact of Lzm-S with the membrane glycoprotein may have resulted in a different effect in FIG. 17. Lectins are nonenzymatic proteins with a specificity for a particular carbohydrate structure, but unlike Lzm-S, do not have the capability of hydrolyzing the bond between two monosaccharide units (42). Thus, the lectin results support the notion that Lzm-S does not irreversibly cleave the membrane glycoprotein. Furthermore, it was found that bathing the ventricular trabeculae with KH totally reversed the depression caused by Lzm-S. On the other hand, the addition of the Lzm-S inhibitors TAC and chitobiose resulted in an attenuated depression, but not in a complete reversal of the depressant effect. The lack of complete reversal may reflect the fact that binding by Lzm-S is sufficiently strong enough, so that it cannot be easily reversed by TAC or chitobiose. However, a very high dose was given, making this explanation less likely. To some extent, the inhibitors by themselves were shown to have some modest cardiac depressant activity thereby limiting their ability to reverse the myocardial depression observed. In addition, there is the possibility that Lzm-S by binding to the cardiac membrane glycoprotein initiates intracellular events, such that binding leads to production of other mediators that cause myocardial depression. Thus, although inhibitors may prevent further interaction between Lzm-S and the membrane glycoprotein, washing may be important in removing the mediators from the environment, and in doing so, in reversing myocardial depression. Further work will be required to determine the extent to which each of these mechanisms explains the present results.

Of interest, the inventors also showed that chitobiose, a two GlcNAc structure, was able to attenuate the reduction in isometric tension caused by Lzm-S, even though a three unit moiety (i.e. Manβ1-4GlcNAcβ1-4GlcNAc structure) was required for Lzm-S's depressant effect. It is also known from previous experiments that the single and four unit GlcNAc structure (i.e. GlcNAc and N,N',N'',N'''-tetraacetylchitotetraose, respectively) do not inhibit Lzm-S's depressant effect to any extent in the RVT preparation (44). Thus, it requires at least two GlcNAc units to block Lzm-S's myocardial depressant effect, while more than 3 GlcNAc units are ineffective. The inventors surmise that a size consideration as well the composition of the inhibitor is important in determining whether a molecule is effective in inhibiting the myocardial depression produced by Lzm-S.

The results further suggest that the glycoprotein to which Lzm-S binds is disrupted by some of the agents used in preparing the single myocyte preparation (46) and that important chemical groups may be digested in the preparation and isolation of myocytes. This consideration may be relevant when data from the intact preparation and isolated myocytes are compared. However, since the inventors were not able to compare canine myocytes and canine trabeculae directly, it is recognized that this is a limitation of the study.

In summary, the present results support the inventors' previous conclusions indicating that Lzm-S contributes to myocardial dysfunction in sepsis (43,44). The findings show that Lzm-S binds to a Manβ1-4GlcNAcβ1-4GlcNAc structure in the tri-mannosyl core of high-mannose/hybrid and tri-antennary carbohydrate structures. The tri-mannosyl core of the N-glycan is conserved among species (45), and thus the present work may be relevant to understanding the nature of myocardial depression found in the human condition. Further work has been carried out (Example 6) to determine the nature of the glycoproteins to which Lzm-S binds.

Example 5

N,N' Diacetylchitobiose, an Inhibitor of Lysozyme, Reverses Myocardial Depression in Experimental Septic Shock Objective In Example 2, the inventors showed that in a canine model of *Escherichia coli* bacteremia in dogs, lysozyme was released as part of the inflammatory reaction and acted as a mediator of the myocardial depression observed. The inventors further showed that N,N',N'' triacetylchitotriose (TAC), a competitive inhibitor of lysozyme, was able to prevent the development of myocardial depression when given either as pretreatment or early after 1.5 hr of sepsis in this model. However, when TAC was given at 3.5 hr post sepsis after myocardial depression had already developed, the inventors could not detect a beneficial effect of this treatment on reversing myocardial depression in this model (see Example 2).

Although TAC was not beneficial in reversing myocardial depression, the inventors subsequently observed that N,N'-diacetylchitobiose (chitobiose) may be even a more potent inhibitor of lysozyme's myocardial depressant effect in in vitro experiments. The extent to which chitobiose may also be superior to reversing myocardial depression in the in vivo preparation has not been tested. Furthermore, based on additional in vitro testing, the inventors estimate that the dose of TAC used in the previous in vivo experiments may have been too low to reverse myocardial depression, since when plasma concentrations of TAC were measured, they were found to be in the low $10^{-5}$M range, while based on in vitro testing, a range between $10^{-4}$M to high $10^{-5}$M would have been preferred. In the present study, the inventors examined whether the administration of chitobiose after 3.5 hrs of *E. coli* sepsis at a relatively high dose could reverse the myocardial depression that develops in this model.

Methods

The *E. coli* model used in this study was identical to that previously described. Sepsis was induced by the intravenous infusion of $10^{10}$ colony forming units of live *E. coli* (designation 0111:B4). The bacteria were suspended in normal saline infusion, which was given over 0.5 h. A constant infusion of approximately $5 \times 10^9$ colony forming units/h of *E. coli* was then maintained for the remainder of the experiment.

During the experiment, the animals (16-21) kg were anesthetized with thiopental sodium (20 mg/kg iv) and constantly infused with sufentanil citrate (1 ug/min) and midazolam (5 ug/kg/min). The rates were adjusted to abolish the palpebral reflex. The animals were placed in the supine position; the trachea was intubated with an endotracheal tube; and the lungs were mechanically ventilated at a tidal volume of 20 ml/kg. The ventilator rate was initially set to maintain blood pH at approximately 7.35 and was changed as necessary over the course of the experiment to maintain blood pH as normal as possible. 100% oxygen was inspired to prevent hypoxemia from contributing to the results, and arterial oxygen tension was maintained greater than 500 mmHg over the course of the study in all experiments.

A thermister tipped catheter was advanced from the jugular vein into the pulmonary artery to measure pulmonary arterial pressure, mean pulmonary capillary wedge pressure (Pwp), right atrial pressure, thermodilution cardiac output (CO, Columbus Instruments, Ohio), and to obtain mixed venous oxygen blood samples. A polyethylene catheter was placed into the femoral artery to measure mean blood pressure (MAP) and to withdraw samples of blood for blood gas analysis. All catheters were connected to transducers (Cobe Laboratories) and were referenced relative to the left atrium. All transducers were connected to a chart recorder (Astro-Med, W Warwick, R.I.). Heart rate (HR) was measured from the recorder tracing. Stroke volume (SV) was calculated as CO/heart rate. Stroke work (SW) was calculated from SV× (MAP-Pwp).

After baseline measurements were obtained, bacteria were infused over a six hour period. Chitobiose was infused at 3.5 hours post sepsis after myocardial depression had already developed and was administered over a 0.5 h period. The dose used was 1000 mg (40 mg/kg) in which the drug was mixed in 100 ml $D_5W$. Based on preliminary calculations, this dose could achieve an approximate plasma concentration of $0.5 \times 10^{-4}$ M. 100 mg/hr of chitobiose (5 mg/kg) mixed in 50 ml of $D_5W$ was then infused over the remaining course of the experiment. Measurements were obtained after 3.5 hr of sepsis, after treatment, and 1 and 2 hrs post treatment. Stroke work (SW) was the primary measurement of the myocardial contractility used in this study. Pulmonary capillary wedge pressure (Pwp) was used as an index of preload and was maintained constant between conditions at approximately 10 mmHg. Normal saline solution was given as necessary to maintain Pwp relatively constant.

Statistics included one way analysis of variance for repeated measures and Student Newman Keuls' multiple comparison test. The results are reported mean±1SD.

Results

The mean arterial blood pressures measured of the 4 dogs studied are shown in FIG. 22. The results showed an approximately 40% decline in mean arterial pressure at the 3.5 hr postsepsis period as compared with baseline. As compared with 3.5 hrs postsepsis, there was a significant increase in mean arterial pressure after treatment. Mean arterial blood pressure remained higher as compared with 3.5 hrs postsepsis over the duration of the experiment.

The changes in stroke-work are shown in FIG. 23. As compared to baseline, there was an approximately 50% reduction in stroke work at 3.5 hrs postsepsis. As compared with 3.5 hrs postsepsis, there was a significant increase in stroke-work at 1 and 2 hrs post treatment. Stroke work measured at the post treatment conditions was not different from that found at baseline.

Stroke-volume (see FIG. 24) showed similar changes as those found in stroke work, but the findings did not reach statistical significance among the treatment conditions. The cardiac output measured at the various conditions are shown in FIG. 25 and were higher at the different conditions as compared with baseline.

Over the course of the experiment, there were no differences in Pwp among the conditions. Pwp measured 10±0.8 mmHg at baseline, 9.6±0.8 mmHg post sepsis, 10.4±0.5 post treatment, 9.5±1.2 mmHg at 1 hr post treatment, and 9.9±0.9 mmHg at 2 hrs post treatment.

As compared to baseline, there was a significant increase in HR post sepsis, but HR was not changed post treatment. HR measured 48±9 at baseline, 98±24* post sepsis, 91±25* after treatment, 86±20* at 1 hr post treatment, and 87±12* at 2 hrs post treatment (*P<0.05 vs. baseline).

Discussion

In this Example, the inventors showed that when chitobiose was administered after myocardial depression had already developed in this *E. coli* model, there was a reversal of the myocardial depression observed. This is in contrast to the results previously reported when TAC was administered under identical circumstances in which no reversal in myocardial depression was found (Example 2). These beneficial findings could be attributable to both the higher dose of the lysozyme inhibitor used in this study (approximately 2.5 times as much) and to the fact that chitobiose may be a better inhibitor of lysozyme's myocardial depressant effect than is TAC. The inventors are of the view that both factors contributed to the results found in this study, although the latter factor may play the more important role.

In previous in vitro studies, the results suggested that chitobiose was a better inhibitor of lysozyme's myocardial depressant effect than was TAC. When chitobiose ($10^{-3}$M) was added to the in vitro preparation before lysozyme was instilled, lysozyme at a concentration of $10^{-7}$M caused only a slight decrease in isometric tension to approximately 90% of baseline, while when no treatment was administered, isometric tension fell to approximately 50% of baseline. In contrast, under identical circumstances in which pretreatment with TAC ($10^{-3}$M) was used, there was less inhibitory effect and isometric tension fell to approximately 77% of baseline. Thus, these results would indicate that when treatment is administered prior to the addition of lysozyme, a greater inhibitory effect may be found with chitobiose.

More importantly, in other in vitro experiments in which either TAC or chitobiose was added to the in vitro preparation after myocardial depression had already been produced by lysozyme, chitobiose attenuated the decline in isometric tension to better extent than did TAC. In these experiments, when no treatment was added, the decline in isometric tension was to 39% of baseline. On the other hand, chitobiose attenuated this decline to 65% of baseline, which was significantly better than the 55% of baseline observed with TAC (Example 4). Thus, whereas TAC and chitobiose are both effective inhibitors of lysozyme's myocardial depressant effect in vitro, the results obtained in this in vivo study indicate that chitobiose in contrast to TAC may reverse the myocardial depression once it has occurred in this sepsis model.

Furthermore, the fact that chitobiose was able to reverse the myocardial depression observed after 3.5 hr of sepsis would be consistent with the reversible nature of the myocardial depression caused by lysozyme shown in recent in vitro studies. These studies indicated that lysozyme causes myocardial dysfunction by binding to a carbohydrate portion of a membrane glycoprotein, and in particular to a TAC variant of the tri-mannosyl core of a membrane glycoprotein (Example 4). The inventors also showed that the binding of lysozyme to the membrane glycoprotein was reversible, in that when ventricular trabeculae were washed with Krebs Henseleit solution, the myocardial depression caused by lysozyme was completely eliminated. In addition, it was determined that nonenzymatic proteins termed lectins that bind to the carbohydrate structure with a specificity similar to that of lysozyme may also cause myocardial depression. Since lectins do not have the capability of hydrolyzing the bond between two monosaccharide units, this would additionally support the concept that the binding between the membrane glycoprotein and lysozyme is reversible. Importantly, the present results showed that myocardial depression that develops in the in vivo preparation may be reversed by chitobiose.

The mechanism by which lysozyme causes myocardial depression in sepsis has been investigated. Studies suggest that lysozyme causes depression by means of the nitric oxide-guanosine 3',5' cyclic monophosphate pathway (Example 6). In this pathway, lysozyme activates a nitric oxide synthase by acting on a protein kinase that in turn leads to myocardial depression.

In summary, the present study adds further information showing the utility of chitobiose in the treatment of sepsis. In contrast to previous findings, chitobiose reverses myocardial depression after it has already developed in this sepsis model. Lysozyme inhibitors represent novel agents in the treatment of cardiovascular collapse in septic shock.

Example 6

The Nitric-oxide Guanosine 3',5'Cyclic Monophosphate Pathway is Involved in Lysozyme Induced Myocardial Depression Objective The mechanism by which lysozyme causes myocardial depression in *E. Coli* sepsis was not previously clear. In the in vitro preparation, the myocardial depression observed after lysozyme is instilled into the bath occurs within minutes, so that the mechanism must involve the activation of an existing signaling pathway that directly leads to myocardial depression. Alternatively, lysozyme causes myocardial depression by direct or indirect effects on the sarcoplasma or sarcolemma membranes that in turn lead to changes in membrane depolarization, such that an inhibition of the calcium current reduces the inotropic state.

Of the possible mechanisms involved, and particularly based on the acuteness of the myocardial depression observed in the in vitro preparation, the inventors hypothesized that lysozyme leads to myocardial depression by activation of nitric oxide (NO). Under various conditions, NO can be released from cardiac endothelial cells or generated within cardiac myocytes themselves. NO has been shown to modulate the myocardial inotropic state. Whether it is positively or negatively inotropic may depend on several factors including the concentration of NO, the rate of NO release, and/or the presence of β-adrenergic stimulation. Low concentrations of NO lead to an increase in inotropy, while high concentrations cause myocardial depression. Endogenous NO is formed by the sequential oxidation of L-arginine. This process is catalyzed by a family of nitric oxide synthases (NOS) that utilize NADPH and oxygen as co-substrates. Three NOS isoforms have been identified and are named after the site of their initial isolation. The neuronal (nNOS or type I) and endothelial (eNOS or type III) are constitutively expressed and synthesize NO in response to an increase in intracellular $Ca^{2+}$. The third isoform (iNOS or type II) may be induced in selected tissues in response to a range of inflammatory mediators and its activity is functionally not dependent on additional $Ca^{2+}$ release. All three isoforms may be found in the heart, although NO may be also generated adjacent to myocytes by eNOS present in the vascular endothelium of myocardial capillaries and venules and in the endocardial lining.

The intracellular signaling pathways responsible for the myocardial depression caused by NO remain poorly understood. One hypothesis is that NO activates soluble guanylyl cyclase and elevates cyclic monophosphate (cGMP), which triggers contractile changes via activation of cGMP-dependent protein kinase (PKG). The negative inotropic effect of NO and cGMP have largely been attributed to a cGMP-mediated reduction in myofilament $Ca^{2+}$ responsiveness, possibility via activation of PKG, although this mechanism has not been fully substantiated.

In this Example, the isolated canine ventricular trabecular preparation was used to examine whether the effect of lysozyme was mediated by NO and also whether eNOS, nNOS, or iNOS was the most likely NOS isoform involved. The inventors additionally assessed whether lysozyme's depressant effect could be attenuated by inhibition of either guanylyl cyclase with 1H-[1,2,4] oxidadiazolo-[4,3-a] quinoxalin-1-one (ODQ) or by inhibition of PKG with guanosine 3',5'-cyclic monophosphorothioate, β-phenyl-1, $N^2$-etheno-8-bromo-Pp-isomer, sodium salt (Rp-8-Br-cGMP). The present Example therefore shows whether the nitric-oxide guanosine 3',5'cyclic monophosphate pathway was the mechanism by which lysozyme induced myocardial depression in septic shock.

Methods

These experiments were approved by the University Animal Care Committee and conform with the Guide for the Care and Use of Laboratory Animals published by the US National Institutes of Health (NIH Publication No 85-23, 1996).

The right ventricular trabecular preparation used in this study has previously been described. Briefly, mongrel dogs (3 to 10 kg) were anesthetized with pentobarbital. The hearts were removed, flushed with 50 ml of Krebs-Henseleit solution (KH), and placed in ice-cold KH bubbled with a mixture of 95% $O_2$ and 5% $CO_2$. Three to four thin trabeculae (<1 mm diameter) were obtained from the right ventricle and were tied at each end with 6-O silk thread. Each thin muscle was suspended in a 5 ml vertical constant temperature bath that contained KH. The muscle was stimulated electrically via punctate platinum bipolar electrodes with rectangular pulses (1 ms duration) at an intensity of 50% above threshold delivered at intervals of 2,000 ms. The trabeculae were stretched to optimal length.

The plasma concentration of lysozyme attained in the inventors' sepsis model is approximately $10^{-8}$M, and the $10^{-7}$M to $10^{-9}$M range was used in the experiments described below. Lysozyme was purified from the spleens of nonseptic dogs as previously described. Measurements were obtained at 5 minute intervals.

In one group of experiments, the non-specific nitric oxide synthase inhibitor $N^G$-monomethyl-L-arginine (L-LNMMA) was used to determine whether it could inhibit the depressant effect of lysozyme. The muscle was incubated with L-NMMA ($10^{-3}$M) for approximately one hour after which lysozyme was instilled into the preparation. As a negative control group, ventricular trabeculae were incubated with D-NMMA after which lysozyme was instilled. With the D-isomer, no inhibition of lysozyme's effect would be expected.

In separate experiments, the respective roles of eNOS, nNOS, and iNOS were evaluated in which the objective was to determine which of the NOS isoforms was responsible for the myocardial depression observed with lysozyme. The relatively specific inhibitors for eNOS (L-NIO.2HCl [L-$N^5$-(1-[Iminoethyl]-ornithine.2HCl], nNOS (N-ω-Propyl-L-arginine [$N^5$-[Imino(propylamino)methyl]-L-ornithine], and iNOS (1400W.dihydrochloride [N-(3-aminomethyl)benzyl)acetamidine.2HCl] were compared in respective experiments in which a range of concentrations of either NOS inhibitor was used.

In other experiments, the muscle was incubated ODQ ($10^{-3}$M) or the PKG inhibitor (Rp-8-Br-cGMP) for one hour. The effect of lysozyme on isometric tension was compared to trabeculae without the respective inhibitors.

Statistics

The results are expressed as a percent of baseline isometric tension. Statistical analyses included two-way analysis of variance and Student Newman Keuls' multiple comparison test. The results are reported as mean (±SD).

Results

In FIG. 26, the results show that L-NMMA markedly attenuated lysozyme's myocardial depressant effect in the in vitro preparation. As shown in the figure, the NO donor L-arginine was able to competively overcome the effect of L-NMMA. Among the control experiments included, L-NMMA alone caused no change in isometric tension over the duration of the experiment. In FIG. 27, D-NMMA (the isomer of L-NMMA) showed no inhibition of lysozyme's myocardial depressant activity.

The effects of the three NOS inhibitors are shown in FIG. 28 (eNOS), FIG. 29 (nNOS), and FIG. 30 (iNOS), respectively. At high concentrations, all three inhibitors were able to attenuate the effect of lysozyme. However, the inhibitor to which lysozyme was most sensitive was eNOS. As shown in FIG. 28, eNOS inhibited lysozyme's depressant effect at a concentration of $10^{-8}$M, while the other inhibitors required a higher concentration. The individual effects of the three inhibitors are compared in FIG. 31 in which it was shown that eNOS was the most potent in the prevention of lysozyme's myocardial depressant effect as compared with the other NOS inhibitors.

In FIGS. 32 and 33, the results show that lysozyme's myocardial depressant effect could be blocked by both ODQ and Rp-8-Br-cGMP. Control experiments showed no effect of the enzyme inhibitors on the development of isometric tension in the in vitro preparation.

Discussion

In this Example, the results indicate that lysozyme causes myocardial depression by the release of NO. The NOS isoform involved in this depression appears to be eNOS. eNOS has been identified in both endothelial and myocytes. It is not clear from this study the extent to which the myocyte or endothelium is involved in contributing to lysozyme's effect. Since inhibitors of cGMP and PKG are also able to block the effect of lysozyme, it appears that the release of NO results in an increase in cGMP that in turn activates PKG and leads to myocardial depression.

The mechanism by which activation of PKG results in myocardial depression may be related to a decrease in myofilament $Ca^{2+}$ sensitivity. There is some evidence that PKG can phosphorylate troponin I and that the contractile effects of NO may related to troponin I phosphorylation (see FIG. 34). Further work will have to be performed to determine if lysozyme acts by this phosphorylating mechanism.

In addition, the glycoprotein to which lysozyme binds will also have to be determined. As shown in FIG. 34, it is the inventors' hypothesis that this binding occurs in the region of the caveolae, and that this binding stimulates the release of NO. The present study supports the notion that the nitric-oxide guanosine 3',5'cyclic monophosphate pathway is involved in the myocardial depression induced by lysozyme.

In terms of FIG. 34, L-arginine and adequate cofactors, nitric oxide (NO) is generated by inducible nitric oxide synthase (iNOS) in the cytosol and by endothelial nitric oxide synthase (eNOS) in caveolae and in the vicinity of the sarcoplasmic reticulum (SR) (nNOS). To be activated, eNOS must be dissociated from caveolin-3 and activated by calmodulin (CaM). eNOS activity can be modulated by various protein kinases (PKA, PKB, PKC, AMPK) and activated by muscarinic $M_2$ receptor and $B_3$-adrenergic receptor coupled with inhibitory G proteins (Gi) through undefined mechanisms. Once generated, NO exerts direct inhibitory effects on mitochondrial respiratory complexes or indirect oxidative and nitrosative stress through peroxintrite (OONOO⁻), super oxide ($O_2^-$) and $N_2O_2$ generation. Its main signaling pathway involves activation of guanylate cyclase (GC), generating cyclic guanosine monophosphate (cGMP). This second messenger can activate either cyclic adenosine monophosphate (cAMP) phosphodiesterases ($PD_2$ and $PD_3$), thereby limiting (or increasing for $PDE_3$), the β1-β2 adrenergic pathway, or protein kinase G (PKG). PKG will phosphorylate different proteins responsible for the following effects of NO: 1) troponin I (T), leading to calcium desensitization, sarcomere relaxation and consequent negative inotropic effect, positive lusitropic effect: 2) adenosine diphosphate (ADP) ribosyl cyclase (ARC), increasing the cyclic ADP ribose, opening the ryanodine receptor, and leading to calcium release from the SR (increased excitation-contraction coupling); and 3) the voltage-sensitive L-type calcium channel (Ica), reducing the calcium entry and promoting a negative inotropic effect. Finally, some important modulators [(+) and (−)] of nitric oxide synthase (NOS) gene transcription and NOS mRNA stability are noticed at the nuclear level: hypoxia (−), oxidized low-density lipoproteins (oxLDL)(−), tumor necrosis factor alpha (TNF-α)(−), lipopolysaccharides (LPS) (−), insulin (+), and shear stress (+).

In the present study, the pathways delineated by the circles #1, #2, and #3 in FIG. 9 have been examined and show that the release of NO causes activation of cGMP and PKG. In future experiments, a skinned preparation will be used as previously described to see if the sensitivity of the myofilaments to $Ca^{2+}$ is decreased as compared to KH treated muscles.

While the present invention has been described with reference to what are presently considered to be the preferred examples, it is to be understood that the invention is not limited to the disclosed examples. To the contrary, the invention is intended to cover various modifications and equivalent arrangements included within the spirit and scope of the appended claims.

All publications, patents and patent applications are herein incorporated by reference in their entirety to the same extent as if each individual publication, patent or patent application was specifically and individually indicated to be incorporated by reference in its entirety.

TABLE 1

Hemodynamics and blood parameters in the Pretreatment Study

|  | Baseline | Treatment | 3 h | 5 h |
|---|---|---|---|---|
| Treatment Group (n = 6) | | | | |
| HR | 74 ± 11 | 78 ± 5 | 105 ± 5* | 90 ± 5 |
| Pwp | 9.3 ± .8 | 10.4 ± 1 | 9 ± .9 | 9.6 ± .9 |
| SVR | 2472 ± 320 | 1872 ± 320 | 1272 ± 221* | 1504 ± 249* |
| Arterial pH | 7.35 ± .01 | 7.28 ± .01* | 7.25 ± .001* | 7.22 ± 0.1* |
| Hct | 33 ± 1 | 34 ± 2 | 28 ± 2 | 26 ± 3 |
| Placebo Group (n = 6) | | | | |
| HR | 82 ± 16 | 82 ± 16 | 97 ± 5 | 90 ± 5 |
| Pwp | 8.9 ± 1 | 10.3 ± 1 | 8.9 ± .6 | 8.3 ± .8 |
| SVR | 2072 ± 310 | 1420 ± 164 | 1274 ± 141 | 1711 ± 348 |
| Arterial pH | 7.33 ± .01 | 7.31 ± .01 | 7.25 ± .01* | 7.23 ± .01* |
| Hct | 33 ± 2 | 31 ± 2 | 25 ± 2* | 24 ± 2* |

Mean (±SE). Treatment and placebo treatments were administered over 0.5 h. Measurements were obtained immediately after infusion was completed. Sepsis was then initiated after which three and five hour postsepsis measurements were obtained.
HR is heart rate (beats/min);
Pwp is pulmonary capillary wedge pressure (mmHg),
SVR is systemic vascular resistance (dynes s $cm^{-5}$),
Hct is hematocrit (%).
*$P < .05$ vs. baseline by one way ANOVA and SNK.

TABLE 2

Hemodynamics and blood parameters in the Early Treatment Study (n = 5)

|  | Baseline | 6 h |
|---|---|---|
| Treatment Group (n = 5) | | |
| HR | 68 ± 9 | 94 ± 8 |
| Pwp | 10 ± .5 | 10.9 ± 1 |
| SVR | 2160 ± 581 | 1792 ± 233 |
| Arterial pH | 7.23 ± .03 | 7.24 ± .03 |
| Hct | 31 ± 2 | 30 ± 4 |
| Lactate | 1 ± .1 | 1 ± .1 |
| Placebo Group (n = 5) | | |
| HR | 71 ± 15 | 96 ± 8 |
| Pwp | 9 ± 1 | 9.8 ± 1 |
| SVR | 1888 ± 164 | 1600 ± 389 |
| Arterial pH | 7.35 ± .02 | 7.27 ± .03 |
| Hct | 33 ± 3 | 32 ± 3 |
| Lactate | .7 ± .1 | .9 ± .1 |

Mean (±SE). 6 h measurements were obtained 6 h after sepsis was initiated.
HR is heart rate (beats/min);
Pwp is pulmonary capillary wedge pressure (mmHg),
SVR is systemic vascular resistance (dynes s $cm^{-5}$),
Hct is hematocrit (%),
lactate is in mM.

TABLE 3

Hemodynamics and blood parameters in the Late Treatment Study

|  | Baseline | 3.5 h Post sepsis | Posttreatment | 2 h Posttreatment |
|---|---|---|---|---|
| Treatment Group (n = 5) | | | | |
| HR | 60 ± 4 | 113 ± 9 | 96 ± 8* | 90 ± 9* |
| Pwp | 9.4 ± 1 | 9.8 ± 1 | 10.5 ± 1.4 | 10 ± 1.6 |
| SVR | 2437 ± 343 | 1200 ± 262* | 1268 ± 196* | 1280 ± 182* |
| Arterial pH | 7.34 ± .015 | 7.24 ± .05* | 7.20 ± .04* | 7.20 ± .04* |
| Hct | 34 ± 2 | 26 ± 5 | 27 ± 5 | 29 ± 6 |
| Lactate | .9 ± .2 | 1.2 ± 2.5 | 1.3 ± .2 | 1.3 ± .4 |
| Placebo Group (n = 4) | | | | |
| HR | 61 ± 8 | 99 ± 10* | 89 ± 6* | 89 ± 9* |
| Pwp | 9.6 ± 1 | 9.6 ± 1 | 9.7 ± 1 | 9.6 ± 1 |
| SVR | 1992 ± 124 | 800 ± 87* | 832 ± 128* | 1380 ± 153* |
| Arterial pH | 7.36 ± .001 | 7.23 ± .025* | 7.22 ± .03* | 7.20 ± .04* |
| Hct | 35 ± 1 | 30 ± 5 | 28 ± 5 | 28 ± 5 |
| Lactate | 1.15 ± .16 | 1.5 ± 25 | 1.7 ± .25* | 1.46 ± .2 |

Mean (±SE). Treatment and placebo treatments were administered over 0.5 h and measurements were obtained immediately after their infusion; 2 h measurements were obtained 2 h after TAC or placebo treatments (6 h post-sepsis).
HR is heart rate (beats/min);
Pwp is pulmonary capillary wedge pressure (mmHg),
SVR is systemic vascular resistance (dynes s $cm^{-5}$),
Hct is hematocrit (%), lactate is in mM.
*$P < .05$ vs. baseline by one way ANOVA and SNK.

Full Citations for References Referred to in the Specification

1. Parker J, Adams R. Development of myocardial dysfunction in endotoxin shock. Am J Physiol 1985; 248: H818-H826.
2. Parker M M, Shelhamer J H, Bacharach S L, Green M, Natanson C, Federick, T, Damske B, Parrillo J. Profound but reversible myocardial depression in patients with septic shock. Ann Intern Med 1984; 100: 483-490.
3. Lefer A, Rovetto M. Influence of a myocardial depressant factor on physiologic properties of cardiac muscle. Proc. Soc Exp Biol 1970; 134: 269-273.
4. Lefer A, Cowgill R, Marshall F, Hall L Brand E. Characterization of a myocardial depressant factor present in hemorrhagic shock. Am J Physiol 1967; 213: 492-498.
5. Parrillo J, Burch C, Shelhamer J, Parker M, Natanson C, Schuette W. A circulating myocardial depressant substance in humans with septic shock. J Clin Invest 1985; 76: 1539-1553.
6. Gomez A, Wang R, Unruh H, Light R B, Bose D, Chau T, Correa E, Mink S. 1990. Hemofiltration reverses left ventricular dysfunction during sepsis in dogs. Anesthesiology 73: 671-685.
7. Jha P, Jacobs H, Bose D, Wang R, Yang J, Light R B, Mink S. 1993. Effects of *E. coli* sepsis and myocardial depressant factor on interval-force relations in dog ventricle. Am. J. Physiol. 1993; 264 (Heart Circ Physiol 33): H1402-H1410.
8. Eng, J K, McCormick A L, Yates J R. 1994. An approach to correlated tandem mass spectral data of peptides with amino acid sequences in a protein database with amino acid sequences. J. Am Soc Mass Spectrom 1994; 5: 976-989.
9. Chittum H S, Lane W S, Carlson B A, Roller P P, Lung F T, Lee B J, Hatfield D L. Rabbit B- globin is extended beyond its UGA stop codon by multiple suppressions and translational reading gaps. Biochemistry 1998; 37: 10866-10870.
10. National Institutes of Health. 1996. Guide for the Care and Use of Laboratory Animals (NIH Publication No 85-23). Bethesda, Md., National Institutes of Health.
11. Edman, P. Sequence determination. Mol Biol Biochem Biophys 1970; 8: 211-255.
12. Rademacher T W, Parekh R B, Dwek R A. Glycobiology. Annu Rev Biochem. 1988; 57: 785-838.
13. Böyum A. Separation of white blood cells. Nature 1954; 204: 793-794.
14. Grobler J A, Rao R, Pervaiz S, Brew K. Sequences of two highly divergent canine type c lysozymes: Implications for the evolutionary origins of the lysozyme/a-lactalbumin superfamily. Archives Biochem Biophys 1994; 313: 360-366.
15. Shugar D. Measurement of lysozyme activity and the ultra violet inactivation of lysozyme. Biochim. Biophys. Acta 1952; 8: 302-309.
16. Chipman D M, Sharon N. Mechanism of lysozyme action. Science 1965; 165: 454-465.
17. Rand-Meir T, Dahlquist F W, Raftery M A. Use of synthetic substrates to study binding and catalysis by lysozyme. Biochemistry 1969; 8: 4206-4214.
18. Li X, Eschun G, Bose D, Jacobs H, Yang J J, Light R B, Mink S N. Histamine H3 activation depresses cardiac function in experimental sepsis. J Appl Physiol 1998; 85: 1693-1701.
19. Eichenholz P W, Eichacker P Q, Hoffman W D, Banks S M, Parrillo J E, Danner R L, Natanson C. Tumor necrosis factor challenges in canines: patterns of cardiovascular dysfunction. Am J Physiol 1992; 263: H668-H675.
20. Finkel M S, Oddis C V, Jacob T D, Watkins S C, Hattler B G, Simmons R L. Negative inotropic effects of cytokines on the heart mediated by nitric oxide. Science 1992; 257: 387-389.
21. Burgess P, Appel S H, Wilson C A, Polk H C. Detection of intraabdominal abscess by serum lysozyme estimation. Surgery 1994; 115: 16-21.
22. McDonald T E, Grinman M N, Carthy C M, Walley K R. Endotoxin infusion in rats induces apoptotic and survival pathways in hearts. Am J Physiol (Heart Circ Physiol) 2000; 279: H2053-H2061.
23. Gu M, Bose R, Bose D, Yang J, Li X, Light R B, Jacobs H, Mink S N. Tumour necrosis factor-a, but not septic plasma depresses cardiac myofilament contraction. Can J. Anaesth. 1998; 45: 352-359.
24. Fleming A. 1922. On a remarkable bacteriolytic element found in tissue and secretions. Proc R Soc Lond. (Biol) 1922; 93: 306-307.
25. Briggs R S, Perillie P E, Finch S C. Lysozyme in bone marrow and peripheral blood cells. J. Histochem. Cytochem 1969; 14: 167-170.
26. Hansen N E, Andersen V. Lysozyme activity in human neutrophilic granulocytes. British Journal of Haematology 1973; 24: 613-623.
27. Hansen N E, Karle H., Andersen V, Olgaard K. Lysozyme turnover in man. J Clin Invest 1972; 51: 1146-1155.
28. Henning U, Wolf W P, Holtzhauer M. Primary cultures of cardiac muscle cells as models for investigation of protein glycosylation. Mol. Cell. Biochem. 1996; 160-161: 41-46.
29. Ufret-Vincenty, C. A., Baro, D. J., Santana, L. F. Differential contribution of sialic acid to the function of repolarization K (+) currents in ventricular myocytes. Am J Physiol Cell Physiol. 2001; 281: C464-C474.
30. Bennett E R. Effects of channel cytoplasmic regions on the activation mechanisms of cardiac versus skeletal muscle Na+ channels. Biophysical Journal 1999; 77: 2999-3009.
31. Lollike K, Kjeldsen L, Sengelov H, Borregaard N. Purification of lysozyme from human neutrophils, and development of an ELISA for quantification in cells and plasma. Leukemia 1995; 9: 206-209.
32. Granton J T, Goddard C M, Allard M F, van Eeden, S, Walley K R. 1997. Leukocytes and decreased left ventricular contractility during endotoxemia in rabbits. Am J Respir Crit Care Med.1997; 155: 1977-83.
33. Flecknell, P. Laboratory Animal Anaesthesia, 2nd ed. Academic Press, San Diego, Calif., 112, 1996.
34. Chrusch C, Bands, C, Bose D, Li X, Jacobs H, Duke K, Bautista E, Eschun G, Light R B, Mink S N. Impaired Hepatic Extraction and increased splanchnic production contribute to lactic acidosis in canine sepsis. Am J Respir Crit Care Med 2000; 161: 517-526.
35. Mink S N, Li X, Bose D, Gu M, Liu G, Jacobs H, Light R B. Early but not delayed continuous arteriovenous hemofiltration improves cardiovascular function in sepsis in dogs. Intensive Care Med 1999; 25: 733-743.
36. Maley F, Trimble R B, Tarentino A L, Plummber T H. Characterization of glycoproteins and their associated oligosaccharides through the use of endoglycosidases. Anal Biochem 1989; 80: 195-204.
37. Nachbar M S, Oppenheim J D, Thomas J O. Lectins in the US Diet. Isolation and characterization of a lectin from the tomato (*Lycopersicon esculentum*). J Biol Chem 1980; 255: 2056-61.
38. Crowley J I, Goldstein I J, Arnarp J, Lonngren J. Carbohydrate binding studies on the lectin from *Datura stramonium* seeds. Arch Biochem Biophys 1984; 231: 524-33.

39. Nagata Y, Burger M M. Wheat germ agglutinin. Molecular characteristics and specificity for sugar binding. J Biol Chem 1974; 249: 3116-22.
40. Gilboa-Garber N Mizarhi L. A new mitogenic D-galactosephilic lectin isolated from seeds of the coral-tree *Erythrina corallodendron*. Comparisons with Glycine max (soybean) and *Pseudomonas aeruginosa* lectins. Can J Biochem 1981; 59: 315-20.
41. Hammarstrom S, Westoo A, Bjork I. Subunit structure of *Helix pomatia* A hemagglutinin. Scand J Immunol 1972; 1:295-309.
42. Variki A, Cummings R, Esko J, Freeze H, Hart G, Marth J (eds) Essentials of Glycobiology Cold Spring Harbor Laboratory Press, Cold Spring, N.Y., p 445-467, p 333-344.
43. Mink S N, Jacobs, H, Bose D, et al. Lysozyme: a mediator of myocardial depression and adrenergic dysfunction in septic shock in dogs. J Mol Cellular Card 2003; 35: 265-275.
44. Mink S N, Jacobs, H, Bose D, et al. N,N',N'' triacetylglucosamine, an inhibitor of lysozyme, prevents myocardial depression in *E. coli* sepsis in dogs. Critical Care Med 2004:32;
45. Fukuda M. Cell surface carbohydrates: cell type-specific expression. In:
Molecular and cellular glycobiology, ed by Fukuda M and Hindsgaul O. Oxford University Press, New York 2000, pp. 1-61.
46. Louch W E, Ferrier G R, Howlett S E. Changes in excitation-contraction coupling in an isolated ventricular myocyte model of cardiac stunning. Am J Physiol Heart Circ Physiol 2002; 283: H800-H810.
47. Kobata A. Use of endo- and exoglycosidases for structural studies of glycoconjugates. Anal Biochem 1979; 100; 1-14.
48. Waddling C A, Plummer T H, Tarentino A L, Roey P V. Structural basis for the substrate specificity of endo-β-N-acetylglucosaminidase F3. Biochemistry 2000; 39:7878-7885.
49. Mink S N, Jacobs, H, Bose D, Duke K, Cheng Z, Liu G, Light R B. Lysozyme: a mediator of myocardial depression and adrenergic dysfunction in septic shock in dogs. J Mol Cellular Card 2003; 35: 265-275.
50. Stiles G L, Benovic J L, Caron M G, Lefkowitz R J. Mammalian β-adrenergic receptors. Distinct glycoprotein populations containing high mannose or complex type carbohydrate chains. J Biol Chem 1984; 259: 8566-8663.
51. Morris A J, Malbon C C. Physiological regulation of G Protein signaling. Physiological Reviews 1999; 79: 1373-1430.
52. Prewitt R M, Wood L D H. Effect of altered resistive afterload on left ventricular systolic mechanics in dogs. Anesthesiology 1982; 56: 195-202.
53. Hansen N E, Andersen V. Lysozyme activity in human neutrophilic granulocytes. British Journal of Haematology 1973; 24: 613-623.

We claim:

1. A method of reducing myocardial dysfunction comprising administering an effective amount of an agent that can inhibit lysozyme to an animal undergoing a dysregulated systemic inflammatory response, wherein the agent that can inhibit lysozyme is selected from the group consisting of: N,N' diacetylglucosamine (chitobiose), N,N', N'' triacetylglucosamine (TAC), an anti-sense oligonucleotide to lysozyme and an antibody to lysozyme.

2. A method according to claim 1 wherein the agent is N,N' diacetylglucosamine (chitobiose) or N,N', N'' triacetylglucosamine (TAC).

3. A method according to claim 1 wherein the agent is an antisense oligonucleotide to lysozyme or antibody to lysozyme.

4. A method according to claim 1 where the animal has a condition selected from the group consisting of sepsis and systemic inflammatory response syndrome (SIRS).

5. A method of reducing the onset of myocardial dysfunction in an animal with sepsis comprising administering an effective amount of an agent that can inhibit lysozyme to the animal, wherein the agent that can inhibit lysozyme is selected from the group consisting of: : N,N' diacetylglucosamine (chitobiose), N,N', N'' triacetylglucosamine (TAC), an anti-sense oligonucleotide to lysozyme and an antibody to lysozyme.

6. A method of reversing myocardial depression in an animal with sepsis comprising administering an effective amount of an agent that can inhibit lysozyme to the animal, wherein the agent that can inhibit lysozyme is selected from the group consisting of: : N,N' diacetylglucosamine (chitobiose), N,N', N'' triacetylglucosamine (TAC), an anti-sense oligonucleotide to lysozyme and an antibody to lysozyme.

7. A method according to claim 6 wherein the agent is N,N' diacetylglucosamine (chitobiose).

8. A method of treating a condition selected from the group consisting of septic shock and systemic inflammatory response syndrome (SIRS) comprising administering an effective amount of an agent that can inhibit lysozyme to an animal undergoing a dysregulated inflammatory response, wherein the agent that can inhibit lysozyme is selected from the group consisting of: : N,N' diacetylglucosamine (chitobiose), N,N', N'' triacetylglucosamine (TAC), and an antibody to lysozyme.

9. A method according to claim 8 wherein the agent is N,N' diacetylglucosamine (chitobiose) or N,N', N'' triacetylglucosamine (TAC).

10. A method according to claim 8 wherein the agent is an antisense oligonucleotide to lysozyme or antibody to lysozyme.

* * * * *